(12) United States Patent
Petluri et al.

(10) Patent No.: US 12,123,554 B2
(45) Date of Patent: Oct. 22, 2024

(54) MULTI-CHANNEL SYSTEMS FOR PROVIDING TUNABLE LIGHT WITH HIGH COLOR RENDERING AND BIOLOGICAL EFFECTS

(71) Applicant: KORRUS, INC., Los Angeles, CA (US)

(72) Inventors: Raghuram L. V. Petluri, Los Angeles, CA (US); Paul Kenneth Pickard, Los Angeles, CA (US)

(73) Assignee: KORRUS, INC., Los Angeles, CA (US)

( * ) Notice: Subject to any disclaimer, the term of this patent is extended or adjusted under 35 U.S.C. 154(b) by 0 days.

(21) Appl. No.: 17/850,216

(22) Filed: Jun. 27, 2022

(65) Prior Publication Data

US 2023/0127451 A1     Apr. 27, 2023

Related U.S. Application Data

(63) Continuation of application No. 16/927,564, filed on Jul. 13, 2020, now Pat. No. 11,371,660, which is a
(Continued)

(51) Int. Cl.
*F21K 9/00*        (2016.01)
*F21Y 113/13*     (2016.01)
(Continued)

(52) U.S. Cl.
CPC ............ *F21K 9/00* (2013.01); *H01L 25/0753* (2013.01); *H01L 27/153* (2013.01); *H01L 33/50* (2013.01);
(Continued)

(58) Field of Classification Search
None
See application file for complete search history.

(56) References Cited

U.S. PATENT DOCUMENTS 7,250,715 B2    7/2007   Mueller
9,181,471 B2    11/2015   Kang
(Continued)

FOREIGN PATENT DOCUMENTS

CN      101617405 A    12/2009
CN      101688644 A    3/2010
(Continued)

OTHER PUBLICATIONS

"Evaluating Color Rendition Using IES TM-30-15"; Solid-State Lighting Technology Fact Sheet; U.S. Dept. of Energy, Oct. 2015; 6 pages.
(Continued)

*Primary Examiner* — Crystal L Hammond
(74) *Attorney, Agent, or Firm* — FisherBroyles LLP

(57) ABSTRACT

The present disclosure provides systems for generating tunable white light. The systems include a plurality of LED strings that generate light with color points that fall within red, blue, green, and cyan color ranges, with each LED string being driven with a separately controllable drive current in order to tune the generated light output. Methods of generating white light by combining light generated by red, blue, green, and cyan color channels. Methods of generating white light points at substantially the same 1931 CIE chromaticity diagram color coordinates having different EML.

12 Claims, 57 Drawing Sheets

Related U.S. Application Data continuation of application No. PCT/US2018/020792, filed on Mar. 2, 2018.

(60) Provisional application No. 62/634,798, filed on Feb. 23, 2018, provisional application No. 62/616,414, filed on Jan. 11, 2018, provisional application No. 62/616,423, filed on Jan. 11, 2018, provisional application No. 62/616,404, filed on Jan. 11, 2018, provisional application No. 62/616,401, filed on Jan. 11, 2018.

(51) Int. Cl.
| | |
|---|---|
| F21Y 115/10 | (2016.01) |
| H01L 25/075 | (2006.01) |
| H01L 27/15 | (2006.01) |
| H01L 33/50 | (2010.01) |
| H05B 45/20 | (2020.01) |

(52) U.S. Cl.
CPC .......... *H05B 45/20* (2020.01); *F21Y 2113/13* (2016.08); *F21Y 2115/10* (2016.08); *H01L 33/502* (2013.01)

(56) References Cited

U.S. PATENT DOCUMENTS

| | | | |
|---|---|---|---|
| 9,380,671 B1 | 6/2016 | Janos | |
| 9,526,143 B1* | 12/2016 | Petluri | H01L 33/504 |
| 9,609,715 B1* | 3/2017 | Petluri | C09K 11/0883 |
| 11,528,792 B2 | 12/2022 | Miskin | |
| 11,565,012 B2 | 1/2023 | Grenon | |
| 11,578,841 B2 | 2/2023 | Soler | |
| 11,589,433 B2 | 2/2023 | Vilgiate | |
| 11,589,436 B2 | 2/2023 | Petluri | |
| 2005/0161586 A1 | 7/2005 | Rains, Jr. | |
| 2006/0152140 A1 | 7/2006 | Brandes | |
| 2007/0053188 A1 | 3/2007 | New | |
| 2007/0096057 A1 | 5/2007 | Hampden-Smith | |
| 2007/0223219 A1 | 9/2007 | Medendorp, Jr. | |
| 2008/0224598 A1 | 9/2008 | Baretz | |
| 2009/0161356 A1* | 6/2009 | Negley | F21K 9/233 |
| | | | 362/230 |
| 2009/0184616 A1 | 7/2009 | Van De Ven | |
| 2009/0218960 A1 | 9/2009 | Lyons | |
| 2010/0174345 A1 | 7/2010 | Ashdown | |
| 2010/0315012 A1 | 12/2010 | Kim | |
| 2011/0084614 A1 | 4/2011 | Eisele | |
| 2011/0115407 A1 | 5/2011 | Wibben | |
| 2011/0216522 A1 | 9/2011 | Harbers | |
| 2011/0279015 A1 | 11/2011 | Negley | |
| 2011/0309773 A1 | 12/2011 | Beers | |
| 2012/0038280 A1 | 2/2012 | Zoorob | |
| 2012/0112661 A1 | 5/2012 | Van De Ven et al. | |
| 2012/0146519 A1 | 6/2012 | Briggs | |
| 2012/0223657 A1 | 9/2012 | Van De Ven | |
| 2012/0236553 A1 | 9/2012 | Cash | |
| 2012/0307487 A1 | 12/2012 | Eckel | |
| 2013/0002157 A1 | 1/2013 | Van De Ven | |
| 2013/0002167 A1 | 1/2013 | Van De Ven | |
| 2013/0070442 A1 | 3/2013 | Negley | |
| 2013/0140490 A1 | 6/2013 | Fujinaga | |
| 2013/0241392 A1 | 9/2013 | Pickard | |
| 2013/0249434 A1 | 9/2013 | Medendorp, Jr. | |
| 2013/0258636 A1 | 10/2013 | Rettke | |
| 2013/0327964 A1 | 12/2013 | Otsuka | |
| 2014/0048743 A1 | 2/2014 | Le-Mercier | |
| 2014/0111985 A1 | 4/2014 | Harbers | |
| 2014/0159600 A1 | 6/2014 | Sutardja | |
| 2014/0167601 A1 | 6/2014 | Harry | |
| 2014/0232288 A1 | 8/2014 | Brandes | |
| 2014/0312376 A1 | 10/2014 | Wilcox | |
| 2014/0333216 A1 | 11/2014 | Zhang | |
| 2015/0002034 A1 | 1/2015 | Van De Ven | |
| 2015/0097200 A1* | 4/2015 | Bergmann | H01L 33/50 |
| | | | 257/89 |
| 2015/0184813 A1 | 7/2015 | Harbers | |
| 2015/0295144 A1 | 10/2015 | Weiler | |
| 2016/0116141 A1 | 4/2016 | Tseng | |
| 2016/0309561 A1* | 10/2016 | Hamilton | H05B 45/46 |
| 2016/0320004 A1 | 11/2016 | Tudorica | |
| 2018/0261733 A1 | 9/2018 | Miwa | |
| 2018/0274754 A1 | 9/2018 | Kusano | |
| 2018/0323349 A1 | 11/2018 | Kim | |
| 2018/0338359 A1 | 11/2018 | Soler | |
| 2019/0103523 A1 | 4/2019 | Choi | |
| 2020/0077486 A1 | 3/2020 | Lai | |

FOREIGN PATENT DOCUMENTS

| | | |
|---|---|---|
| CN | 103650643 | 3/2014 |
| CN | 104633545 A | 5/2015 |
| JP | 2007059272 A | 3/2007 |
| WO | 2016146688 | 9/2016 |
| WO | 2017131693 A1 | 8/2017 |
| WO | 2017131703 A1 | 8/2017 |
| WO | 2017131706 | 8/2017 |
| WO | 2017131706 A1 | 8/2017 |
| WO | 2017131713 | 8/2017 |
| WO | 2017131714 | 8/2017 |
| WO | 2017131715 A1 | 8/2017 |

OTHER PUBLICATIONS

Davidson et al.; "Comparison of Munsell and MacAdam Color Spaces"; Journal of the Optical Society of America; vol. 48 No. 9; Sep. 1958; p. 606-608.

European Search Report mailed Jan. 10, 2022, in European Application No. 18900130.8 (11 pages).

Figueiro et al.; "Designing with Circadian Stimulus"; Illuminating Engineering Society; Oct. 2016; p. 31-34.

Gall et al.; "Definition and Measurement of Circadian Radiometric Quantities"; CIE Symposium on Light and Health: Non-Visual Effects; 2004; 5 pages.

Hye Oh et al., "Healthy, natural, efficient and tunable lighting: four-package white LEDs for optimizing the circadian effect, color quality and vision performance," Light: Science & Applications 3.2 (2014); 23pp.

International Patent Application No. PCT/US2016/015318; Int'l Preliminary Report on Patentability; dated Aug. 9, 2018; 15 pages.

International Patent Application No. PCT/US2016/015318; Int'l Written Opinion and the Search Report; dated Apr. 11, 2016; 16 pages.

International Patent Application No. PCT/US2016/015368; Int'l Preliminary Report on Patentability; dated Aug. 9, 2018; 8 pages.

International Patent Application No. PCT/US2016/015368; Int'l Search Report and the Written Opinion; dated Apr. 19, 2016; 9 pages.

International Patent Application No. PCT/US2016/015385; Int'l Preliminary Report on Patentability; dated Aug. 9, 2018; 11 pages.

International Patent Application No. PCT/US2016/015385; Int'l Written Opinion and the Search Report; dated Apr. 8, 2016; 12 pages.

International Patent Application No. PCT/US2016/015402; Int'l Preliminary Report on Patentability; dated Aug. 9, 2018; 13 pages.

International Patent Application No. PCT/US2016/015402; Int'l Search Report and the Written Opinion; dated Apr. 22, 2016; 15 pages.

International Patent Application No. PCT/US2016/015441; Int'l Preliminary Report on Patentability; dated Aug. 9, 2018; 8 pages.

International Patent Application No. PCT/US2016/015441; Int'l Written Opinion and the Search Report; dated Mar. 31, 2016; 8 pages.

International Patent Application No. PCT/US2018/020787; Int'l Written Opinion and the Search Report; dated May 14, 2018; 8 pages.

(56) References Cited

OTHER PUBLICATIONS

International Patent Application No. PCT/US2018/020793; Int'l Written Opinion and the Search Report; dated May 10, 2018; 9 pages.
Lucas et al., "Measuring and using light in the melanopsin age," Trends in Neurosciences, Jan. 2014, vol. 37, No. 1, 9pp.
Rea et al.; "Modelling the spectral sensitivity of the human circadian system"; Light Research & Technology; Dec. 2011; 12 pages.
Royer, Michael; "Color Rendition Metrics: An Overview of Ongoing Work"; U.S. Dept. of Energy; Lightfair; Jun. 2014; 26 pages.
Office Action mailed Oct. 14, 2022 in German Application No. 11 2018 006 827.7, including English language translation.
Office Action mailed Jul. 28, 2022 in German Application No. 11 2018 006 831.5, including English language translation.
Chinese Office Action mailed Jul. 6, 2022, in Chinese Application No. 201880091145.3, including English language translation.
Author: Davidson Nutshell, Title: Comparison Nunsell and MacAdam Space; p. 1-8, Date: 1958 Year: 1958.
Author: Michal Royer: Title: Understanding and Applying TM-30-15 and p. 1-70, Date: Sep. 15, 2015 Year: 2015.
Chinese Notice of Allowance mailed Jun. 5, 2023, in Application No. 201880091145.3, including English translation.

\* cited by examiner

FIG. 7A

| Blue Channel Relative Intensity | Red Channel Relative Intensity | Green Channel Relative Intensity | Cyan Channel Relative Intensity | ccx | ccy | CCT | duv | Ra | R9 | R13 | R15 | LER (luminous efficacy of radiation) (lm/W) | COI |
|---|---|---|---|---|---|---|---|---|---|---|---|---|---|
| 1 | 0 | 0.0565 | 0.1341 | 0.2601 | 0.2726 | 14821.69 | 5.26 | 90.17 | 91.95 | 93.92 | 85.88 | 242.94 | |
| 1 | 0.0533 | 0.1179 | 0.1115 | 0.2772 | 0.295 | 9993.43 | 5.69 | 92.38 | 94.86 | 95.65 | 88.42 | 256.01 | |
| 1 | 0.0633 | 0.1502 | 0.1598 | 0.2928 | 0.3128 | 7983.56 | 5.56 | 93.12 | 89.7 | 94.96 | 89.75 | 263.28 | |
| 0.9192 | 0.105 | 0.1664 | 0.1664 | 0.3046 | 0.3248 | 7003.54 | 5.25 | 93.49 | 85.56 | 94.4 | 90.38 | 267.26 | |
| 1 | 0.1147 | 0.2536 | 0.0856 | 0.3122 | 0.3334 | 6498.37 | 5.74 | 95.17 | 97.55 | 97.83 | 92.3 | 275.55 | |
| 0.8708 | 0.1535 | 0.2375 | 0.105 | 0.3216 | 0.3416 | 5986.03 | 5.23 | 95.61 | 93.92 | 97.16 | 92.93 | 276.3 | 4.43 |
| 0.7705 | 0.1826 | 0.2536 | 0.0824 | 0.3325 | 0.3519 | 5498.38 | 5.45 | 96.36 | 96.4 | 97.93 | 93.93 | 280.29 | 3.64 |
| 0.609 | 0.2116 | 0.2342 | 0.0792 | 0.3459 | 0.3629 | 5005.73 | 5.27 | 96.77 | 94.86 | 97.77 | 94.75 | 282.15 | 2.52 |
| 0.5444 | 0.2924 | 0.2569 | 0.1018 | 0.3627 | 0.377 | 4512.74 | 5.76 | 95.72 | 90.49 | 96.26 | 93.42 | 284.04 | 1.72 |

FIG. 7B

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) | BLH Factor (µW/cm²/lux) |
|---|---|---|---|---|---|---|---|---|---|---|---|---|---|
| 1 | 0 | 0.1376 | | 0.2797 | 0.2869 | 10188.24 | -0.11 | 92.19 | 93.52 | 97.23 | 88.77 | 255.88 | 0.0449 |
| 1 | 0 | 0.1987 | | 0.2882 | 0.307 | 8484.09 | 5.2 | 92.04 | 81.24 | 96.07 | 89.11 | 269.27 | 0.0457 |
| 1 | 0 | 0.2071 | | 0.2897 | 0.3098 | 8287.03 | 5.76 | 91.85 | 78.99 | 95.46 | 88.82 | 271.03 | 0.0458 |
| 1 | 0.0273 | 0.2327 | | 0.2975 | 0.3181 | 7548.23 | 5.67 | 92.68 | 82.52 | 95.9 | 89.88 | 274.26 | 0.0461 |
| 1 | 0.0497 | 0.2552 | | 0.3036 | 0.3247 | 7061.67 | 5.74 | 93.21 | 84.34 | 96.08 | 90.53 | 276.77 | 0.0464 |
| 1 | 0.0883 | 0.2809 | | 0.312 | 0.3321 | 6515.58 | 5.12 | 94.23 | 89.15 | 97.01 | 91.87 | 278.66 | 0.0467 |
| 0.8401 | 0.1147 | 0.2698 | | 0.3214 | 0.3414 | 5997.82 | 5.24 | 94.87 | 90.9 | 97.19 | 92.68 | 281.58 | 0.0472 |
| 0.7738 | 0.1535 | 0.2859 | | 0.332 | 0.3515 | 5518.58 | 5.47 | 95.4 | 91.77 | 97.23 | 93.36 | 284.51 | 0.0478 |
| 0.6414 | 0.1986 | 0.2859 | | 0.3469 | 0.3644 | 4977.02 | 5.63 | 95.05 | 93.68 | 96.31 | 92.04 | 287.46 | 0.0487 |
| 0.525 | 0.2504 | 0.2859 | | 0.3633 | 0.3772 | 4495.7 | 5.68 | 95.93 | 97.03 | 96.99 | 93.35 | 289.4 | 0.0499 |
| 0.5218 | 0.3764 | 0.2859 | | 0.381 | 0.3784 | 3995.75 | 0.61 | 96.73 | 88.34 | 96.84 | 94.32 | 282.01 | 0.0498 |
| 0.3409 | 0.3829 | 0.2084 | | 0.4031 | 0.3845 | 3496.27 | -2.28 | 95.52 | 83.27 | 94.27 | 92.92 | 276.67 | 0.0379 |
| 0.2149 | 0.3829 | 0.1405 | | 0.4291 | 0.3875 | 2997.45 | -5.66 | 93.9 | 82.39 | 91.79 | 91.62 | 268.06 | 0.0280 |
| 0.1761 | 0.483 | 0.1405 | | 0.4511 | 0.3941 | 2694.67 | -5.48 | 93.88 | 87.53 | 92.05 | 93.24 | 263.94 | 0.0211 |
| 0.1147 | 0.5121 | 0.1082 | | 0.4755 | 0.3971 | 2394.43 | -5.75 | 93.88 | 94.64 | 92.66 | 95.46 | 256.87 | 0.0155 |
| 0.063 | 0.5121 | 0.0695 | | 0.5028 | 0.3971 | 2105.02 | -5.78 | 93.5 | 93.46 | 94.61 | 99.06 | 247.41 | 0.0109 |
| 0.0242 | 0.5121 | 0.0307 | | 0.5363 | 0.3933 | 1806.76 | -5.13 | 92.86 | 75.5 | 99.1 | 93.61 | 234.5 | 0.0067 |

FIG. 7C

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10188.24 | 271.7767 | 117.5123 | 302.2344 | 1.175123 | 102.6789 | 1.339897 | | | 95.67311 | | 84 | 94 |
| 8484.09 | 255.2839 | 105.6171 | 285.8989 | 1.056171 | 96.55727 | 1.242974 | | | 93.13028 | | 95 | 95 |
| 8287.03 | 0.060652 | 0.024935 | 283.3167 | 1.039844 | | 1.2290 | 1910 | 0.6050 | | | 85 | 93 |
| 7548.23 | 0.063043 | 0.025418 | 271.2259 | 0.983768 | | 1.1776 | 1764 | 0.5980 | | | 86 | 95 |
| 7061.67 | 0.06512 | 0.025838 | 261.8909 | 0.941295 | | 1.1387 | 1653 | 0.5910 | | | 86 | 95 |
| 6515.58 | 0.067603 | 0.026326 | 249.8219 | 0.891874 | | 1.0917 | 1526 | 0.5830 | | | 87 | 96 |
| 5997.82 | 219.9086 | 83.55299 | 236.4818 | 0.83553 | 90.96754 | 1.039521 | | | 95.21464 | | 88 | 97 |
| 5518.58 | 210.3198 | 77.67346 | 222.115 | 0.776735 | 88.19138 | 0.984503 | | | 95.34702 | 4.34 | 89 | 97 |
| 4977.02 | 198.0732 | 70.30835 | 203.1191 | 0.703084 | 83.93456 | 0.914422 | | | 95.3394 | 3.06 | 89 | 97 |
| 4495.7 | 185.7664 | 63.08259 | 183.4506 | 0.630826 | 78.74207 | 0.844224 | | | 95.07326 | 1.91 | 88 | 97 |
| 3995.75 | 175.5091 | 58.54987 | 165.8751 | 0.585499 | 78.37629 | 0.78765 | | | 102.2301 | 0.8 | 90 | 97 |
| 3496.27 | 162.1604 | 51.98178 | 144.4398 | 0.519818 | 73.78714 | 0.713161 | | | 108.6856 | 2.73 | 91 | 101 |
| 2997.45 | 147.4127 | 45.2754 | 121.8447 | 0.452754 | 68.38171 | 0.631587 | | | 121.0082 | 5.38 | 93 | 103 |
| 2694.67 | 134.8267 | 38.9983 | 103.3136 | 0.389983 | 60.02355 | 0.561254 | | | 125.9038 | 7.19 | 93 | 103 |
| 2394.43 | 121.4557 | 32.90427 | 84.80933 | 0.329043 | 51.51462 | 0.487289 | | | 135.8321 | 9.51 | 93 | 105 |
| 2105.02 | 106.6825 | 26.62673 | 66.07927 | 0.266267 | 42.12676 | 0.406168 | | | 151.9294 | 12.45 | 91 | 106 |
| 1806.76 | 88.16478 | 19.28298 | 45.30811 | 0.19283 | 30.55817 | 0.305184 | | | 181.2621 | 16.55 | 85 | 108 |

FIG. 7D

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) | BLH Factor (μW/cm²/lux) |
|---|---|---|---|---|---|---|---|---|---|---|---|---|---|
| 1 | 0 | | 0.2472 | 0.2555 | 0.2677 | 17012.72 | 5.86 | 86.89 | 69.63 | 87.8 | 82.35 | 234.19 | |
| 0.9289 | 0.0824 | | 0.3409 | 0.2772 | 0.294 | 10063.4 | 5.26 | 83.86 | 44.13 | 82.19 | 79.08 | 241.92 | 0.047685 |
| 0.7705 | 0.1341 | | 0.4055 | 0.2927 | 0.3131 | 7983.54 | 5.81 | 81.29 | 33.87 | 79.14 | 77.2 | 246.64 | 0.049277 |
| 0.5897 | 0.1858 | | 0.4152 | 0.3127 | 0.3331 | 6475.3 | 5.32 | 78.38 | 29.33 | 75.9 | 74.87 | 250.47 | 0.051291 |
| 0.3667 | 0.2504 | | 0.412 | 0.3456 | 0.3631 | 5018.75 | 5.48 | 75.33 | 24.2 | 73.22 | 74.19 | 254.96 | 0.045436 |
| 0.2472 | 0.3118 | | 0.3538 | 0.3799 | 0.3774 | 4019.24 | 0.49 | 72.41 | 21 | 69.8 | 71.49 | 252.88 | 0.039939 |
| 0.2149 | 0.412 | | 0.3409 | 0.4054 | 0.3852 | 3452.3 | -2.44 | 70.06 | 3.79 | 65.78 | 64.43 | 225.25 | 0.031299 |
| 0.1502 | 0.412 | | 0.2601 | 0.4292 | 0.3883 | 3001.85 | -5.35 | 68.96 | 9.53 | 63.87 | 64.24 | 217.71 | 0.024187 |
| 0.1018 | 0.4152 | | 0.2213 | 0.4491 | 0.3944 | 2726.54 | -5.21 | 68.55 | 16.3 | 63.31 | 65.74 | 212.93 | 0.018917 |
| 0.0695 | 0.4992 | | 0.1955 | 0.4768 | 0.3978 | 2383.41 | -5.54 | 69.79 | 30.44 | 64.27 | 69.66 | 205.31 | 0.013527 |

FIG. 7E

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 17012.72 | 310.7942 | 143.0871 | 336.43 | 1.430871 | 106.6436 | 1.657282 | 2888 | 0.637 | 95.77167 | | 80 | 94 |
| 10063.4 | 279.8046 | 123.5606 | 299.9875 | 1.235606 | 107.5335 | 1.499154 | 2358 | 0.623 | 98.15453 | | 79 | 96 |
| 7983.54 | 260.7096 | 111.5733 | 276.0982 | 1.115733 | 105.0787 | 1.403607 | 2032 | 0.611 | 98.32741 | | 78 | 98 |
| 6475.3 | 240.366 | 99.19 | 249.1967 | 0.9919 | 100.7139 | 1.295979 | 1793 | 0.594 | 98.2316 | | 76 | 99 |
| 5018.75 | 212.077 | 82.22599 | 210.2105 | 0.82226 | 89.03901 | 1.143503 | 1259 | 0.561 | 95.50878 | 3.74 | 73 | 98 |
| 4019.24 | 188.275 | 69.44227 | 176.0453 | 0.694423 | 80.25483 | 0.998802 | 952 | 0.523 | 99.06391 | 5.2 | 72 | 97 |
| 3452.3 | 171.8018 | 59.41785 | 134.7861 | 0.594179 | 77.42833 | 0.864708 | 1580 | 0.587 | 109.0913 | 8.35 | 74 | 103 |
| 3001.85 | 157.5945 | 52.59413 | 115.2891 | 0.525941 | 71.00732 | 0.778647 | 1418 | 0.575 | 118.5254 | 9.91 | 74 | 104 |
| 2726.54 | 146.1505 | 46.84274 | 100.4049 | 0.468427 | 62.11947 | 0.714799 | 1293 | 0.564 | 120.3094 | 11.22 | 74 | 103 |
| 2383.41 | 130.1891 | 39.19278 | 80.98893 | 0.391928 | 51.32713 | 0.617772 | 1111 | 0.545 | 128.7498 | 13.2 | 74 | 103 |

FIG. 7F

| Approximate CCT | Blue, Red, & Green | | Blue, Red, & Cyan | | | Blue, Red, Green, Cyan | | |
|---|---|---|---|---|---|---|---|---|
| | Ra | EML | Ra | EML | increase of EML vs. Blue/Red/Green | Ra | Increase in Ra vs. Blue/Red/Cyan | Increase in Ra vs. Blue/Red/Green |
| 10000 | 92.2 | 1.339897 | 83.86 | 1.499154 | 12% | 92.38 | 8.52 | 0.18 |
| 8000 | 91.85 | 1.215116 | 81.29 | 1.403607 | 16% | 93.12 | 11.83 | 1.27 |
| 6500 | 94.23 | 1.0917 | 78.38 | 1.295979 | 19% | 95.17 | 16.79 | 0.94 |
| 5000 | 95.05 | 0.914422 | 75.33 | 1.143503 | 25% | 96.77 | 21.44 | 1.72 |
| 4000 | 96.73 | 0.78765 | 72.41 | 0.998802 | 27% | | | |
| 3500 | 95.52 | 0.713161 | 70.06 | 0.864708 | 21% | | | |
| 3000 | 93.9 | 0.631587 | 68.96 | 0.778647 | 23% | | | |
| 2700 | 93.88 | 0.561254 | 68.55 | 0.714799 | 27% | | | |
| 2400 | 93.88 | 0.487289 | 69.79 | 0.617772 | 27% | | | |

FIG. 8A

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | 0.1376 | | 0.2797 | 0.2869 | 10188.24 | -0.11 | 92.19 | 93.52 | 97.23 | 88.77 | 255.88 |
| 1 | 0 | 0.1987 | | 0.2882 | 0.3070 | 8484.09 | 5.20 | 92.04 | 81.24 | 96.07 | 89.11 | 269.27 |
| 1 | 0 | 0.2071 | | 0.2897 | 0.3098 | 8287.03 | 5.76 | 91.85 | 78.99 | 95.46 | 88.82 | 271.03 |
| 1 | 0.0273 | 0.2327 | | 0.2975 | 0.3181 | 7548.23 | 5.67 | 92.68 | 82.52 | 95.90 | 89.88 | 274.26 |
| 1 | 0.0497 | 0.2552 | | 0.3036 | 0.3247 | 7061.67 | 5.74 | 93.21 | 84.34 | 96.08 | 90.53 | 276.77 |
| 1 | 0.0883 | 0.2809 | | 0.3120 | 0.3321 | 6515.58 | 5.12 | 94.23 | 89.15 | 97.01 | 91.87 | 278.66 |
| 0.8401 | 0.1147 | 0.2698 | | 0.3214 | 0.3414 | 5997.82 | 5.24 | 94.87 | 90.90 | 97.19 | 92.68 | 281.58 |
| 0.7738 | 0.1535 | 0.2859 | | 0.3320 | 0.3515 | 5518.58 | 5.47 | 95.40 | 91.77 | 97.23 | 93.36 | 284.51 |
| 0.6414 | 0.1986 | 0.2859 | | 0.3469 | 0.3644 | 4977.02 | 5.63 | 95.05 | 93.68 | 96.31 | 92.04 | 287.46 |
| 0.5250 | 0.2504 | 0.2859 | | 0.3633 | 0.3772 | 4495.7 | 5.68 | 95.93 | 97.03 | 96.99 | 93.35 | 289.40 |
| 0.5218 | 0.3764 | 0.2859 | | 0.3810 | 0.3784 | 3995.75 | 0.61 | 96.73 | 88.34 | 96.84 | 94.32 | 282.01 |
| 0.3409 | 0.3829 | 0.2084 | | 0.4031 | 0.3845 | 3496.27 | -2.28 | 95.52 | 83.27 | 94.27 | 92.92 | 276.67 |
| 0.2149 | 0.3829 | 0.1405 | | 0.4291 | 0.3875 | 2997.45 | -5.66 | 93.90 | 82.39 | 91.79 | 91.62 | 268.06 |
| 0.1761 | 0.4830 | 0.1405 | | 0.4511 | 0.3941 | 2694.67 | -5.48 | 93.88 | 87.53 | 92.05 | 93.24 | 263.94 |
| 0.1147 | 0.5121 | 0.1082 | | 0.4755 | 0.3971 | 2394.43 | -5.75 | 93.88 | 94.64 | 92.66 | 95.46 | 256.87 |
| 0.063 | 0.5121 | 0.0695 | | 0.5028 | 0.3971 | 2105.02 | -5.78 | 93.50 | 93.46 | 94.61 | 99.06 | 247.41 |
| 0.0242 | 0.5121 | 0.0307 | | 0.5363 | 0.3933 | 1806.76 | -5.13 | 92.86 | 75.50 | 99.10 | 93.61 | 234.50 |

FIG. 8B

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10188.24 | 271.7767 | 117.5123 | 302.2344 | 1.175123 | 102.6789 | 1.339897 | | | 95.67311 | 9.95 | 84 | 94 |
| 8484.09 | 255.2839 | 105.6171 | 285.8989 | 1.056171 | 96.55727 | 1.242974 | | | 93.13028 | 9.4 | 95 | 95 |
| 8287.03 | 0.060652 | 0.024935 | 283.3167 | 1.039844 | | 1.2290 | 1910 | 0.6050 | | 9.3 | 85 | 93 |
| 7548.23 | 0.063043 | 0.025418 | 271.2259 | 0.983768 | | 1.1776 | 1764 | 0.5980 | | 8.24 | 86 | 95 |
| 7061.67 | 0.06512 | 0.025838 | 261.8909 | 0.941295 | | 1.1387 | 1653 | 0.5910 | | 7.48 | 86 | 95 |
| 6515.58 | 0.067603 | 0.026326 | 249.8219 | 0.891874 | | 1.0917 | 1526 | 0.5830 | | 6.39 | 87 | 96 |
| 5997.82 | 219.9086 | 83.55299 | 236.4818 | 0.83553 | 90.96754 | 1.039521 | | | 95.21464 | 5.37 | 88 | 97 |
| 5518.58 | 210.3198 | 77.67346 | 222.115 | 0.776735 | 88.19138 | 0.984503 | | | 95.34702 | 4.34 | 89 | 97 |
| 4977.02 | 198.0732 | 70.30835 | 203.1191 | 0.703084 | 83.93456 | 0.914422 | | | 95.3394 | 3.06 | 89 | 97 |
| 4495.7 | 185.7664 | 63.08259 | 183.4506 | 0.630826 | 78.74207 | 0.844224 | | | 95.07326 | 1.91 | 88 | 97 |
| 3995.75 | 175.5091 | 58.54987 | 165.8751 | 0.585499 | 78.37629 | 0.78765 | | | 102.2301 | 0.8 | 90 | 97 |
| 3496.27 | 162.1604 | 51.98178 | 144.4398 | 0.519818 | 73.78714 | 0.713161 | | | 108.6856 | 2.73 | 91 | 101 |
| 2997.45 | 147.4127 | 45.2754 | 121.8447 | 0.452754 | 68.38171 | 0.631587 | | | 121.0082 | 5.38 | 93 | 103 |
| 2694.67 | 134.8267 | 38.9983 | 103.3136 | 0.389983 | 60.02355 | 0.561254 | | | 125.9038 | 7.19 | 93 | 103 |
| 2394.43 | 121.4557 | 32.90427 | 84.80933 | 0.329043 | 51.51462 | 0.487289 | | | 135.8321 | 9.51 | 93 | 105 |
| 2105.02 | 106.6825 | 26.62673 | 66.07927 | 0.266267 | 42.12676 | 0.406168 | | | 151.9294 | 12.45 | 91 | 106 |
| 1806.76 | 88.16478 | 19.28298 | 45.30811 | 0.19283 | 30.55817 | 0.305184 | | | 181.2621 | 16.55 | 85 | 108 |

FIG. 8C

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | | 0.3071 | 0.2903 | 0.3105 | 8224.47 | 5.79 | 90.35 | 57.22 | 90.44 | 87.28 | 277.21 |
| 1 | 0.01 | | 0.3215 | 0.2928 | 0.3136 | 7967.52 | 5.97 | 90.98 | 60.32 | | | 274.07 |
| 1 | 0.0275 | | 0.3538 | 0.2986 | 0.3194 | 7453.83 | 5.74 | 92.91 | 70.6 | | | 273.28 |
| 1 | 0.0533 | | 0.3861 | 0.3049 | 0.3248 | 6983.39 | 5.05 | 95.01 | 82.22 | | | 271.67 |
| 0.8805 | 0.0717 | | 0.3925 | 0.3122 | 0.3335 | 6494.67 | 5.73 | 96.75 | 89.91 | 97.18 | 95.32 | 271.6 |
| 0.8123 | 0.1024 | | 0.4232 | 0.3218 | 0.3432 | 5978.12 | 5.98 | 98.25 | 99.68 | 98.48 | 96.99 | 270.53 |
| 0.727 | 0.1297 | | 0.43 | 0.3306 | 0.3507 | 5578.02 | 5.71 | 97.28 | 91.08 | 97.12 | 96.53 | 271.06 |
| 0.6621 | 0.1843 | | 0.4744 | 0.3442 | 0.3616 | 5066.08 | 5.32 | 94.62 | 5.32 | 94.01 | 93.67 | 265.53 |
| 0.5222 | 0.2457 | | 0.4949 | 0.3628 | 0.3759 | 4505.6 | 5.24 | 90.63 | 65.66 | 89.55 | 89.2 | 261.28 |
| 0.4471 | 0.3242 | | 0.4505 | 0.3796 | 0.3747 | 4007 | -0.7 | 85.32 | 46.65 | 82.83 | 81.04 | 249.61 |
| 0.3413 | 0.3958 | | 0.4369 | 0.3999 | 0.3857 | 3548.13 | -2.79 | 81.22 | 38.19 | 77.94 | 76.68 | 241.49 |
| 0.3441 | 0.6543 | | 0.5574 | 0.422 | 0.3845 | 3102.19 | -5.88 | 77.21 | 33.63 | 72.94 | 72.99 | 230.93 |
| 0.3174 | 0.7679 | | 0.6246 | 0.4307 | 0.389 | 2981.04 | -5.26 | 76.22 | 34.12 | 71.98 | 72.95 | 228.86 |
| 0.1877 | 0.8294 | | 0.5734 | 0.451 | 0.3937 | 2692.45 | -5.62 | 74.07 | 36.14 | 69.35 | 72.57 | 221.42 |
| 0.0614 | 0.8771 | | 0.4983 | 0.4758 | 0.3973 | 2391.54 | -5.71 | 72.13 | 42.05 | 67.11 | 73.59 | 212.1 |
| 0 | 1 | | 0.4949 | 0.4915 | 0.3972 | 2216 | -5.91 | 71.37 | 47.84 | 66.27 | 75.05 | 205.59 |

FIG. 8D

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 8224.47 | 0.058417 | 0.023419 | 278.5391 | 1.004786 | | 1.149604 | 1803 | 0.6 | | 10.72 | 87 | 97 |
| 7967.52 | 0.059399 | 0.023676 | 274.119 | 0.987907 | | 1.138074 | 1757 | 0.597 | | 10.88 | 88 | 98 |
| 7453.83 | 0.061447 | 0.024229 | 263.9205 | 0.954472 | | 1.114765 | 1668 | 0.592 | | 10.19 | 90 | 99 |
| 6983.39 | 0.063467 | 0.024772 | 253.3743 | 0.922285 | | 1.090885 | 1582 | 0.587 | | 8.85 | 91 | 100 |
| 6494.67 | 0.067137 | 0.025778 | 241.5354 | 0.880088 | | 1.063796 | 1467 | 0.579 | | 6.09 | 93 | 100 |
| 5978.12 | 0.071757 | 0.027027 | 227.2382 | 0.831947 | | 1.030246 | 1338 | 0.568 | | 4.5 | 94 | 101 |
| 5578.02 | 0.075976 | 0.028163 | 214.889 | 0.79276 | | 1.001183 | 1235 | 0.558 | | 3.19 | 94 | 102 |
| 5066.08 | 0.083234 | 0.030114 | 197.3913 | 0.737489 | | 0.959247 | 1089 | 0.542 | | 1.77 | 92 | 102 |
| 4505.6 | 0.095966 | 0.033534 | 175.6366 | 0.667676 | | 0.905536 | 907 | 0.516 | | 2.33 | 88 | 102 |
| 4007 | 0.089832 | 0.031188 | 158.7117 | 0.631889 | | 0.85948 | 829 | 0.502 | | 3.66 | 87 | 104 |
| 3548.13 | 0.074092 | 0.025052 | 139.7787 | 0.575704 | | 0.805538 | 691 | 0.473 | | 5.68 | 84 | 105 |
| 3102.19 | 0.060123 | 0.01988 | 121.3502 | 0.523025 | | 0.747048 | 1369 | 0.571 | | 7.92 | 82 | 106 |
| 2981.04 | 0.056228 | 0.018266 | 114.4815 | 0.498074 | | 0.725669 | 1325 | 0.567 | | 8.61 | 81 | 106 |
| 2692.45 | 0.047488 | 0.014951 | 99.71628 | 0.448681 | | 0.674698 | 1224 | 0.557 | | 10.42 | 79 | 106 |
| 2391.54 | 0.038656 | 0.011693 | 83.40824 | 0.392048 | | 0.61246 | 1103 | 0.544 | | 12.67 | 76 | 104 |
| 2216 | 0.033746 | 0.009967 | 73.9607 | 0.358749 | | 0.571807 | 1026 | 0.534 | | 14.27 | 75 | 104 |

FIG. 8E

| Approximate CCT | Blue, Red, & Green | | Blue, Red, & Cyan | | increase of EML |
|---|---|---|---|---|---|
| | Ra | EML | Ra | EML | |
| 10000 | 92.2 | 1.339897 | | | |
| 8000 | 91.85 | 1.215116 | 90.98 | 1.138074 | -6% |
| 6500 | 94.23 | 1.0917 | 96.75 | 1.063796 | -3% |
| 5000 | 95.05 | 0.914422 | 94.62 | 0.959247 | 5% |
| 4000 | 96.73 | 0.78765 | 85.32 | 0.85948 | 9% |
| 3500 | 95.52 | 0.713161 | 81.22 | 0.805538 | 13% |
| 3000 | 93.9 | 0.631587 | 76.22 | 0.725669 | 15% |
| 2700 | 93.88 | 0.561254 | 74.07 | 0.674698 | 20% |
| 2400 | 93.88 | 0.487289 | 72.13 | 0.61246 | 26% |
| 2100 | 93.5 | 0.406168 | 71.37 | 0.571807 | 41% |
| 1800 | 92.86 | 0.305184 | | | |

FIG. 9A

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | 0.1376 | | 0.2797 | 0.2869 | 10188.24 | -0.11 | 92.19 | 93.52 | 97.23 | 88.77 | 255.88 |
| 1 | 0 | 0.1987 | | 0.2882 | 0.307 | 8484.09 | 5.2 | 92.04 | 81.24 | 96.07 | 89.11 | 269.27 |
| 1 | 0 | 0.2071 | | 0.2897 | 0.3098 | 8287.03 | 5.76 | 91.85 | 78.99 | 95.46 | 88.82 | 271.03 |
| 1 | 0.0273 | 0.2327 | | 0.2975 | 0.3181 | 7548.23 | 5.67 | 92.68 | 82.52 | 95.9 | 89.88 | 274.26 |
| 1 | 0.0497 | 0.2552 | | 0.3036 | 0.3247 | 7061.67 | 5.74 | 93.21 | 84.34 | 96.08 | 90.53 | 276.77 |
| 1 | 0.0883 | 0.2809 | | 0.312 | 0.3321 | 6515.58 | 5.12 | 94.23 | 89.15 | 97.01 | 91.87 | 278.66 |
| 0.8401 | 0.1147 | 0.2698 | | 0.3214 | 0.3414 | 5997.82 | 5.24 | 94.87 | 90.9 | 97.19 | 92.68 | 281.58 |
| 0.7738 | 0.1535 | 0.2859 | | 0.332 | 0.3515 | 5518.58 | 5.47 | 95.4 | 91.77 | 97.23 | 93.36 | 284.51 |
| 0.6414 | 0.1986 | 0.2859 | | 0.3469 | 0.3644 | 4977.02 | 5.63 | 95.05 | 93.68 | 96.31 | 92.04 | 287.46 |
| 0.525 | 0.2504 | 0.2859 | | 0.3633 | 0.3772 | 4495.7 | 5.68 | 95.93 | 97.03 | 96.99 | 93.35 | 289.4 |
| 0.5218 | 0.3764 | 0.2859 | | 0.381 | 0.3784 | 3995.75 | 0.61 | 96.73 | 88.34 | 96.84 | 94.32 | 282.01 |
| 0.3409 | 0.3829 | 0.2084 | | 0.4031 | 0.3845 | 3496.27 | -2.28 | 95.52 | 83.27 | 94.27 | 92.92 | 276.67 |
| 0.2149 | 0.3829 | 0.1405 | | 0.4291 | 0.3875 | 2997.45 | -5.66 | 93.9 | 82.39 | 91.79 | 91.62 | 268.06 |
| 0.1761 | 0.483 | 0.1405 | | 0.4511 | 0.3941 | 2694.67 | -5.48 | 93.88 | 87.53 | 92.05 | 93.24 | 263.94 |
| 0.1147 | 0.5121 | 0.1082 | | 0.4755 | 0.3971 | 2394.43 | -5.75 | 93.88 | 94.64 | 92.66 | 95.46 | 256.87 |
| 0.063 | 0.5121 | 0.0695 | | 0.5028 | 0.3971 | 2105.02 | -5.78 | 93.5 | 93.46 | 94.61 | 99.06 | 247.41 |
| 0.0242 | 0.5121 | 0.0307 | | 0.5363 | 0.3933 | 1806.76 | -5.13 | 92.86 | 75.5 | 99.1 | 93.61 | 234.5 |

FIG. 9B

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10188.24 | 271.7767 | 117.5123 | 302.2344 | 1.175123 | 102.6789 | 1.339897 | | | 95.67311 | 9.95 | 84 | 94 |
| 8484.09 | 255.2839 | 105.6171 | 285.8989 | 1.056171 | 96.55727 | 1.242974 | | | 93.13028 | 9.4 | 95 | 95 |
| 8287.03 | 0.060652 | 0.024935 | 283.3167 | 1.039844 | | 1.2290 | 1910 | 0.6050 | | 9.3 | 85 | 93 |
| 7548.23 | 0.063043 | 0.025418 | 271.2259 | 0.983768 | | 1.1776 | 1764 | 0.5980 | | 8.24 | 86 | 95 |
| 7061.67 | 0.06512 | 0.025838 | 261.8909 | 0.941295 | | 1.1387 | 1653 | 0.5910 | | 7.48 | 86 | 95 |
| 6515.58 | 0.067603 | 0.026326 | 249.8219 | 0.891874 | | 1.0917 | 1526 | 0.5830 | | 6.39 | 87 | 96 |
| 5997.82 | 219.9086 | 83.55299 | 236.4818 | 0.83553 | 90.96754 | 1.039521 | | | 95.21464 | 5.37 | 88 | 97 |
| 5518.58 | 210.3198 | 77.67346 | 222.115 | 0.776735 | 88.19138 | 0.984503 | | | 95.34702 | 4.34 | 89 | 97 |
| 4977.02 | 198.0732 | 70.30835 | 203.1191 | 0.703084 | 83.93456 | 0.914422 | | | 95.3394 | 3.06 | 89 | 97 |
| 4495.7 | 185.7664 | 63.08259 | 183.4506 | 0.630826 | 78.74207 | 0.844224 | | | 95.07326 | 1.91 | 88 | 97 |
| 3995.75 | 175.5091 | 58.54987 | 165.8751 | 0.585499 | 78.37629 | 0.78765 | | | 102.2301 | 0.8 | 90 | 97 |
| 3496.27 | 162.1604 | 51.98178 | 144.4398 | 0.519818 | 73.78714 | 0.713161 | | | 108.6856 | 2.73 | 91 | 101 |
| 2997.45 | 147.4127 | 45.2754 | 121.8447 | 0.452754 | 68.38171 | 0.631587 | | | 121.0082 | 5.38 | 93 | 103 |
| 2694.67 | 134.8267 | 38.9983 | 103.3136 | 0.389983 | 60.02355 | 0.561254 | | | 125.9038 | 7.19 | 93 | 103 |
| 2394.43 | 121.4557 | 32.90427 | 84.80933 | 0.329043 | 51.51462 | 0.487289 | | | 135.8321 | 9.51 | 93 | 105 |
| 2105.02 | 106.6825 | 26.62673 | 66.07927 | 0.266267 | 42.12676 | 0.406168 | | | 151.9294 | 12.45 | 91 | 106 |
| 1806.76 | 88.16478 | 19.28298 | 45.30811 | 0.19283 | 30.55817 | 0.305184 | | | 181.2621 | 16.55 | 85 | 108 |

FIG. 9C

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) | BLH Factor (µW/cm²/lux) |
|---|---|---|---|---|---|---|---|---|---|---|---|---|---|
| 1 | 0 | | 0.2924 | 0.2817 | 0.2889 | 9843.24 | -0.36 | 86.86 | 87.86 | 90.44 | 85.49 | 254.21 | 0.052088 |
| | | | | 0.2952 | 0.3042 | 8010.92 | -0.33 | 90.12 | 85.79 | | | | 0.055994 |
| 1 | 0.1341 | | 0.5477 | 0.3136 | 0.3239 | 6493.96 | 0.15 | 86.97 | 85.84 | 89.13 | 87.28 | 267.81 | 0.056311 |
| 1 | 0.399 | | 0.8901 | 0.3438 | 0.3504 | 5047.01 | -0.07 | 86.94 | 86.28 | 88.57 | 88.84 | 274.26 | |
| 0.79 | 0.5185 | | 0.9418 | 0.3603 | 0.3638 | 4516.9 | 0.3 | 86.18 | 85.36 | 88.43 | 88.43 | 276.75 | 0.051667 |
| 0.4701 | 0.5574 | | 0.7932 | 0.3806 | 0.377 | 3996.92 | 0.07 | 86 | 84.21 | 87.75 | 88.92 | 277.37 | 0.046979 |
| 0.2633 | 0.7189 | | 0.7964 | 0.4059 | 0.3919 | 3495.92 | 0.4 | 85.85 | 85.27 | 87.52 | 89.93 | 277.08 | 0.037031 |
| 0.0856 | 1 | | 0.7964 | 0.4372 | 0.404 | 2995.9 | -0.04 | 85.94 | 87.62 | 87.41 | 91.29 | 272.77 | 0.024352 |
| 0 | 1 | | 0.6252 | 0.4575 | 0.4081 | 2713.28 | -0.71 | 86.35 | 90.64 | 87.73 | 92.57 | 267.79 | 0.018491 |

FIG. 9D

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 9843.24 | 273.8848 | 120.5199 | 307.4525 | 1.205199 | 101.8374 | 1.412682 | | | 93.38442 | 9.68 | 80 | 93 |
| 8010.92 | 256.8894 | 109.8358 | 287.1222 | 1.098358 | 99.80332 | 1.321093 | | | 94.03642 | | 81 | 93 |
| 6493.96 | 237.1996 | 97.28068 | 262.8702 | 0.972807 | 94.32945 | 1.215925 | | | 93.16633 | 5.63 | 81 | 93 |
| 5047.01 | 209.6124 | 80.98468 | 222.6859 | 0.809847 | 87.18169 | 1.061687 | | | 95.02306 | 2.53 | 80 | 93 |
| 4516.9 | 196.5953 | 73.27483 | 203.2717 | 0.732748 | 81.265 | 0.989019 | | | 94.56398 | 1.15 | 78 | 92 |
| 3996.92 | 182.254 | 65.10408 | 180.9841 | 0.651041 | 74.21753 | 0.907241 | | | 94.62149 | 1.18 | 78 | 91 |
| 3495.92 | 165.8056 | 55.88497 | 155.1683 | 0.55885 | 64.09982 | 0.812643 | | | 93.27773 | 2.62 | 77 | 90 |
| 2995.9 | 147.3242 | 46.14079 | 126.1025 | 0.461408 | 52.41774 | 0.70309 | | | 93.14132 | 4.83 | 75 | 89 |
| 2713.28 | 135.8219 | 40.45424 | 108.5424 | 0.404542 | 45.58219 | 0.632904 | | | 95.03926 | 6.47 | 75 | 88 |

FIG. 9E

| Approximate CCT | Blue, Red, & Green | | Blue, Red, & Cyan | | |
|---|---|---|---|---|---|
| | Ra | EML | Ra | EML | increase of EML |
| 10000 | 92.2 | 1.339897 | 86.86 | 1.412682 | 5% |
| 8000 | 91.85 | 1.215116 | 90.12 | 1.321093 | 9% |
| 6500 | 94.23 | 1.0917 | 86.97 | 1.215925 | 11% |
| 5000 | 95.05 | 0.914422 | 86.94 | 1.061687 | 16% |
| 4000 | 96.73 | 0.78765 | 86 | 0.907241 | 15% |
| 3500 | 95.52 | 0.713161 | 85.85 | 0.812643 | 14% |
| 3000 | 93.9 | 0.631587 | 85.94 | 0.70309 | 11% |
| 2700 | 93.88 | 0.561254 | 86.35 | 0.632904 | 13% |

FIG. 10A

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | 0.1376 | | 0.2797 | 0.2869 | 10188.24 | -0.11 | 92.19 | 93.52 | 97.23 | 88.77 | 255.88 |
| 1 | 0 | 0.1987 | | 0.2882 | 0.307 | 8484.09 | 5.2 | 92.04 | 81.24 | 96.07 | 89.11 | 269.27 |
| 1 | 0 | 0.2071 | | 0.2897 | 0.3098 | 8287.03 | 5.76 | 91.85 | 78.99 | 95.46 | 88.82 | 271.03 |
| 1 | 0.0273 | 0.2327 | | 0.2975 | 0.3181 | 7548.23 | 5.67 | 92.68 | 82.52 | 95.9 | 89.88 | 274.26 |
| 1 | 0.0497 | 0.2552 | | 0.3036 | 0.3247 | 7061.67 | 5.74 | 93.21 | 84.34 | 96.08 | 90.53 | 276.77 |
| 1 | 0.0883 | 0.2809 | | 0.312 | 0.3321 | 6515.58 | 5.12 | 94.23 | 89.15 | 97.01 | 91.87 | 278.66 |
| 0.8401 | 0.1147 | 0.2698 | | 0.3214 | 0.3414 | 5997.82 | 5.24 | 94.87 | 90.9 | 97.19 | 92.68 | 281.58 |
| 0.7738 | 0.1535 | 0.2859 | | 0.332 | 0.3515 | 5518.58 | 5.47 | 95.4 | 91.77 | 97.23 | 93.36 | 284.51 |
| 0.6414 | 0.1986 | 0.2859 | | 0.3469 | 0.3644 | 4977.02 | 5.63 | 95.05 | 93.68 | 96.31 | 92.04 | 287.46 |
| 0.525 | 0.2504 | 0.2859 | | 0.3633 | 0.3772 | 4495.7 | 5.68 | 95.93 | 97.03 | 96.99 | 93.35 | 289.4 |
| 0.5218 | 0.3764 | 0.2859 | | 0.381 | 0.3784 | 3995.75 | 0.61 | 96.73 | 88.34 | 96.84 | 94.32 | 282.01 |
| 0.3409 | 0.3829 | 0.2084 | | 0.4031 | 0.3845 | 3496.27 | -2.28 | 95.52 | 83.27 | 94.27 | 92.92 | 276.67 |
| 0.2149 | 0.3829 | 0.1405 | | 0.4291 | 0.3875 | 2997.45 | -5.66 | 93.9 | 82.39 | 91.79 | 91.62 | 268.06 |
| 0.1761 | 0.483 | 0.1405 | | 0.4511 | 0.3941 | 2694.67 | -5.48 | 93.88 | 87.53 | 92.05 | 93.24 | 263.94 |
| 0.1147 | 0.5121 | 0.1082 | | 0.4755 | 0.3971 | 2394.43 | -5.75 | 93.88 | 94.64 | 92.66 | 95.46 | 256.87 |
| 0.063 | 0.5121 | 0.0695 | | 0.5028 | 0.3971 | 2105.02 | -5.78 | 93.5 | 93.46 | 94.61 | 99.06 | 247.41 |
| 0.0242 | 0.5121 | 0.0307 | | 0.5363 | 0.3933 | 1806.76 | -5.13 | 92.86 | 75.5 | 99.1 | 93.61 | 234.5 |

FIG. 10B

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10188.24 | 271.7767 | 117.5123 | 302.2344 | 1.175123 | 102.6789 | 1.339897 | | | 95.67311 | 9.95 | 84 | 94 |
| 8484.09 | 255.2839 | 105.6171 | 285.8989 | 1.056171 | 96.55727 | 1.242974 | | | 93.13028 | 9.4 | 95 | 95 |
| 8287.03 | 0.060652 | 0.024935 | 283.3167 | 1.039844 | | 1.2290 | 1910 | 0.6050 | | 9.3 | 85 | 93 |
| 7548.23 | 0.063043 | 0.025418 | 271.2259 | 0.983768 | | 1.1776 | 1764 | 0.5980 | | 8.24 | 86 | 95 |
| 7061.67 | 0.06512 | 0.025838 | 261.8909 | 0.941295 | | 1.1387 | 1653 | 0.5910 | | 7.48 | 86 | 95 |
| 6515.58 | 0.067603 | 0.026326 | 249.8219 | 0.891874 | | 1.0917 | 1526 | 0.5830 | | 6.39 | 87 | 96 |
| 5997.82 | 219.9086 | 83.55299 | 236.4818 | 0.83553 | 90.96754 | 1.039521 | | | 95.21464 | 5.37 | 88 | 97 |
| 5518.58 | 210.3198 | 77.67346 | 222.115 | 0.776735 | 88.19138 | 0.984503 | | | 95.34702 | 4.34 | 89 | 97 |
| 4977.02 | 198.0732 | 70.30835 | 203.1191 | 0.703084 | 83.93456 | 0.914422 | | | 95.3394 | 3.06 | 89 | 97 |
| 4495.7 | 185.7664 | 63.08259 | 183.4506 | 0.630826 | 78.74207 | 0.844224 | | | 95.07326 | 1.91 | 88 | 97 |
| 3995.75 | 175.5091 | 58.54987 | 165.8751 | 0.585499 | 78.37629 | 0.78765 | | | 102.2301 | 0.8 | 90 | 97 |
| 3496.27 | 162.1604 | 51.98178 | 144.4398 | 0.519818 | 73.78714 | 0.713161 | | | 108.6856 | 2.73 | 91 | 101 |
| 2997.45 | 147.4127 | 45.2754 | 121.8447 | 0.452754 | 68.38171 | 0.631587 | | | 121.0082 | 5.38 | 93 | 103 |
| 2694.67 | 134.8267 | 38.9983 | 103.3136 | 0.389983 | 60.02355 | 0.561254 | | | 125.9038 | 7.19 | 93 | 103 |
| 2394.43 | 121.4557 | 32.90427 | 84.80933 | 0.329043 | 51.51462 | 0.487289 | | | 135.8321 | 9.51 | 93 | 105 |
| 2105.02 | 106.6825 | 26.62673 | 66.07927 | 0.266267 | 42.12676 | 0.406168 | | | 151.9294 | 12.45 | 91 | 106 |
| 1806.76 | 88.16478 | 19.28298 | 45.30811 | 0.19283 | 30.55817 | 0.305184 | | | 181.2621 | 16.55 | 85 | 108 |

FIG. 10C

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) | BLH Factor (μW/cm2/lux) |
|---|---|---|---|---|---|---|---|---|---|---|---|---|---|
| 1 | 0 | | 0.2472 | 0.2627 | 0.2767 | 13638.77 | 5.57 | 87.17 | 86.18 | 95.62 | 84.95 | 248.97 | 0.048976 |
| 1 | 0.0598 | | 0.3473 | 0.2772 | 0.2951 | 9983.34 | 5.71 | 87.93 | 94.1 | 94.44 | 86.35 | 256.84 | 0.051156 |
| 1 | 0.1147 | | 0.4281 | 0.2878 | 0.3073 | 8507.88 | 5.59 | 88.18 | 93.51 | 93.48 | 87.05 | 261.32 | 0.052995 |
| 1 | 0.1438 | | 0.4669 | 0.2927 | 0.3125 | 7999.42 | 5.47 | 88.22 | 91.59 | 93.02 | 87.27 | 263.02 | 0.053829 |
| 1 | 0.2956 | | 0.6704 | 0.312 | 0.3333 | 6506.07 | 5.72 | 88.18 | 86.74 | 91.88 | 88.14 | 269.57 | 0.058038 |
| 0.7512 | 0.6026 | | 0.9192 | 0.3462 | 0.3638 | 4999.91 | 5.59 | 86.9 | 81.7 | 90.29 | 87.69 | 276.06 | 0.051359 |
| 0.609 | 0.7705 | | 1 | 0.3629 | 0.3755 | 4500.91 | 5.03 | 86.5 | 77.91 | 89.22 | 87.76 | 276.99 | 0.047384 |
| 0.5864 | 1 | | 0.9871 | 0.3805 | 0.3772 | 4001.05 | 0.21 | 85.71 | 68.19 | 86.04 | 85.6 | 271.44 | 0.047443 |
| 0.3731 | 1 | | 0.7674 | 0.4026 | 0.3834 | 3500.62 | -2.61 | 85.17 | 66.41 | 84.3 | 84.83 | 267.29 | 0.03654 |
| 0.2149 | 1 | | 0.5638 | 0.4297 | 0.3887 | 2996.86 | -5.24 | 85.15 | 70.17 | 83.51 | 85.54 | 261.18 | 0.026668 |
| 0.1179 | 1 | | 0.4604 | 0.4504 | 0.394 | 2703.37 | -5.47 | 85.75 | 76.62 | 84.31 | 87.69 | 257.49 | 0.020671 |
| 0.0436 | 1 | | 0.3473 | 0.4758 | 0.398 | 2396.58 | -5.46 | 87.04 | 86.63 | 86.24 | 91.25 | 251.88 | 0.014994 |
| 0 | 1 | | 0.2342 | 0.5039 | 0.3989 | 2107.46 | -5.17 | 88.75 | 97.28 | 89.9 | 96.43 | 244.28 | 0.010341 |

FIG. 10D

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 13638.77 | 295.8507 | 132.9488 | 332.3753 | 1.329488 | 98.58338 | 1.535881 | | | 89.88071 | 12.11 | 79 | 89 |
| 9983.34 | 275.0712 | 119.737 | 308.3927 | 1.19737 | 97.98664 | 1.424326 | | | 90.94726 | 9.61 | 80 | 90 |
| 8507.88 | 261.5876 | 111.2415 | 291.7853 | 1.112415 | 96.66513 | 1.351548 | | | 91.34485 | 8.01 | 80 | 92 |
| 7999.42 | 256.0337 | 107.8003 | 284.5824 | 1.078003 | 96.03455 | 1.321278 | | | 91.56889 | 7.33 | 80 | 92 |
| 6506.07 | 235.4548 | 95.04056 | 257.0871 | 0.950406 | 91.7132 | 1.209162 | | | 91.44454 | 5.04 | 81 | 92 |
| 4999.91 | 205.9337 | 77.32286 | 214.1188 | 0.773229 | 81.68467 | 1.045374 | | | 90.21303 | 2.32 | 79 | 91 |
| 4500.91 | 193.6754 | 70.2778 | 195.2314 | 0.702778 | 76.35476 | 0.975792 | | | 89.68438 | 1.86 | 77 | 90 |
| 4001.05 | 182.6935 | 65.05826 | 177.0969 | 0.650583 | 75.44147 | 0.907956 | | | 95.92608 | 1.99 | 78 | 92 |
| 3500.62 | 168.8287 | 58.0046 | 155.4623 | 0.580046 | 70.49221 | 0.824653 | | | 101.3537 | 3.54 | 79 | 93 |
| 2996.86 | 152.4366 | 49.92099 | 130.7237 | 0.49921 | 63.65425 | 0.724883 | | | 110.6337 | 5.79 | 80 | 95 |
| 2703.37 | 140.1962 | 43.74883 | 112.9342 | 0.437488 | 56.31054 | 0.65107 | | | 115.3608 | 7.42 | 81 | 95 |
| 2396.58 | 125.5357 | 36.62741 | 92.4789 | 0.366274 | 47.35883 | 0.561303 | | | 122.9009 | 9.57 | 82 | 96 |
| 2107.46 | 109.4474 | 29.17893 | 71.44486 | 0.291789 | 37.94625 | 0.460956 | | | 135.3045 | 12.3 | 84 | 97 |

FIG. 10E

| Approximate CCT | Blue, Red, & Green | | Blue, Red, & Cyan | | increase of EML | increase of Ra |
|---|---|---|---|---|---|---|
| | Ra | EML | Ra | EML | | |
| 10000 | 92.2 | 1.339897 | 87.93 | 1.424326 | 6% | 4.27 |
| 8000 | 91.85 | 1.215116 | 88.22 | 1.321278 | 9% | 3.63 |
| 6500 | 94.23 | 1.0917 | 88.18 | 1.209162 | 11% | 6.05 |
| 5000 | 95.05 | 0.914422 | 86.9 | 1.045374 | 14% | 8.15 |
| 4000 | 96.73 | 0.78765 | 85.71 | 0.907956 | 15% | 11.02 |
| 3500 | 95.52 | 0.713161 | 85.17 | 0.824653 | 16% | 10.35 |
| 3000 | 93.9 | 0.631587 | 85.15 | 0.724883 | 15% | 8.75 |
| 2700 | 93.88 | 0.561254 | 85.75 | 0.65107 | 16% | 8.13 |
| 2400 | 93.88 | 0.487289 | 87.04 | 0.561303 | 15% | 6.84 |
| 2100 | 93.5 | 0.406168 | 88.75 | 0.460956 | 13% | 4.75 |

FIG. 11A

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | 0.1376 | | 0.2797 | 0.2869 | 10188.24 | -0.11 | 92.19 | 93.52 | 97.23 | 88.77 | 255.88 |
| 1 | 0 | 0.1987 | | 0.2882 | 0.307 | 8484.09 | 5.2 | 92.04 | 81.24 | 96.07 | 89.11 | 269.27 |
| 1 | 0 | 0.2071 | | 0.2897 | 0.3098 | 8287.03 | 5.76 | 91.85 | 78.99 | 95.46 | 88.82 | 271.03 |
| 1 | 0.0273 | 0.2327 | | 0.2975 | 0.3181 | 7548.23 | 5.67 | 92.68 | 82.52 | 95.9 | 89.88 | 274.26 |
| 1 | 0.0497 | 0.2552 | | 0.3036 | 0.3247 | 7061.67 | 5.74 | 93.21 | 84.34 | 96.08 | 90.53 | 276.77 |
| 1 | 0.0883 | 0.2809 | | 0.312 | 0.3321 | 6515.58 | 5.12 | 94.23 | 89.15 | 97.01 | 91.87 | 278.66 |
| 0.8401 | 0.1147 | 0.2698 | | 0.3214 | 0.3414 | 5997.82 | 5.24 | 94.87 | 90.9 | 97.19 | 92.68 | 281.58 |
| 0.7738 | 0.1535 | 0.2859 | | 0.332 | 0.3515 | 5518.58 | 5.47 | 95.4 | 91.77 | 97.23 | 93.36 | 284.51 |
| 0.6414 | 0.1986 | 0.2859 | | 0.3469 | 0.3644 | 4977.02 | 5.63 | 95.05 | 93.68 | 96.31 | 92.04 | 287.46 |
| 0.525 | 0.2504 | 0.2859 | | 0.3633 | 0.3772 | 4495.7 | 5.68 | 95.93 | 97.03 | 96.99 | 93.35 | 289.4 |
| 0.5218 | 0.3764 | 0.2859 | | 0.381 | 0.3784 | 3995.75 | 0.61 | 96.73 | 88.34 | 96.84 | 94.32 | 282.01 |
| 0.3409 | 0.3829 | 0.2084 | | 0.4031 | 0.3845 | 3496.27 | -2.28 | 95.52 | 83.27 | 94.27 | 92.92 | 276.67 |
| 0.2149 | 0.3829 | 0.1405 | | 0.4291 | 0.3875 | 2997.45 | -5.66 | 93.9 | 82.39 | 91.79 | 91.62 | 268.06 |
| 0.1761 | 0.483 | 0.1405 | | 0.4511 | 0.3941 | 2694.67 | -5.48 | 93.88 | 87.53 | 92.05 | 93.24 | 263.94 |
| 0.1147 | 0.5121 | 0.1082 | | 0.4755 | 0.3971 | 2394.43 | -5.75 | 93.88 | 94.64 | 92.66 | 95.46 | 256.87 |
| 0.063 | 0.5121 | 0.0695 | | 0.5028 | 0.3971 | 2105.02 | -5.78 | 93.5 | 93.46 | 94.61 | 99.06 | 247.41 |
| 0.0242 | 0.5121 | 0.0307 | | 0.5363 | 0.3933 | 1806.76 | -5.13 | 92.86 | 75.5 | 99.1 | 93.61 | 234.5 |

FIG. 11B

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10188.24 | 271.7767 | 117.5123 | 302.2344 | 1.175123 | 102.6789 | 1.339897 | | | 95.67311 | 9.95 | 84 | 94 |
| 8484.09 | 255.2839 | 105.6171 | 285.8989 | 1.056171 | 96.55727 | 1.242974 | | | 93.13028 | 9.4 | 95 | 95 |
| 8287.03 | 0.060652 | 0.024935 | 283.3167 | 1.039844 | | 1.2290 | 1910 | 0.6050 | | 9.3 | 85 | 93 |
| 7548.23 | 0.063043 | 0.025418 | 271.2259 | 0.983768 | | 1.1776 | 1764 | 0.5980 | | 8.24 | 86 | 95 |
| 7061.67 | 0.06512 | 0.025838 | 261.8909 | 0.941295 | | 1.1387 | 1653 | 0.5910 | | 7.48 | 86 | 95 |
| 6515.58 | 0.067603 | 0.026326 | 249.8219 | 0.891874 | | 1.0917 | 1526 | 0.5830 | | 6.39 | 87 | 96 |
| 5997.82 | 219.9086 | 83.55299 | 236.4818 | 0.83553 | 90.96754 | 1.039521 | | | 95.21464 | 5.37 | 88 | 97 |
| 5518.58 | 210.3198 | 77.67346 | 222.115 | 0.776735 | 88.19138 | 0.984503 | | | 95.34702 | 4.34 | 89 | 97 |
| 4977.02 | 198.0732 | 70.30835 | 203.1191 | 0.703084 | 83.93456 | 0.914422 | | | 95.3394 | 3.06 | 89 | 97 |
| 4495.7 | 185.7664 | 63.08259 | 183.4506 | 0.630826 | 78.74207 | 0.844224 | | | 95.07326 | 1.91 | 88 | 97 |
| 3995.75 | 175.5091 | 58.54987 | 165.8751 | 0.585499 | 78.37629 | 0.78765 | | | 102.2301 | 0.8 | 90 | 97 |
| 3496.27 | 162.1604 | 51.98178 | 144.4398 | 0.519818 | 73.78714 | 0.713161 | | | 108.6856 | 2.73 | 91 | 101 |
| 2997.45 | 147.4127 | 45.2754 | 121.8447 | 0.452754 | 68.38171 | 0.631587 | | | 121.0082 | 5.38 | 93 | 103 |
| 2694.67 | 134.8267 | 38.9983 | 103.3136 | 0.389983 | 60.02355 | 0.561254 | | | 125.9038 | 7.19 | 93 | 103 |
| 2394.43 | 121.4557 | 32.90427 | 84.80933 | 0.329043 | 51.51462 | 0.487289 | | | 135.8321 | 9.51 | 93 | 105 |
| 2105.02 | 106.6825 | 26.62673 | 66.07927 | 0.266267 | 42.12676 | 0.406168 | | | 151.9294 | 12.45 | 91 | 106 |
| 1806.76 | 88.16478 | 19.28298 | 45.30811 | 0.19283 | 30.55817 | 0.305184 | | | 181.2621 | 16.55 | 85 | 108 |

FIG. 11C

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) | BLH Factor (µW/cm2/lux) |
|---|---|---|---|---|---|---|---|---|---|---|---|---|---|
| 1 | 0 | | 0.1826 | 0.2613 | 0.2751 | 14152.11 | 5.75 | 89 | 92.23 | 94.77 | 85.87 | 246.29 | 0.046403 |
| 1 | 0.063 | | 0.2504 | 0.2775 | 0.2942 | 9999.81 | 5.06 | 89.64 | 87.36 | 92.5 | 86.82 | 253.5 | 0.047627 |
| 1 | 0.1115 | | 0.3053 | 0.2881 | 0.3069 | 8495.97 | 5.2 | 89.66 | 82.13 | 91.46 | 87.18 | 258.06 | 0.048592 |
| 1 | 0.1341 | | 0.3279 | 0.2925 | 0.3117 | 8029.15 | 5.15 | 89.58 | 79.9 | 90.99 | 87.21 | 259.58 | 0.048988 |
| 1 | 0.2601 | | 0.4507 | 0.3125 | 0.3331 | 6484 | 5.42 | 89.09 | 74.19 | 89.55 | 87.55 | 265.92 | 0.051107 |
| 1 | 0.5929 | | 0.706 | 0.3456 | 0.3624 | 5008.17 | 5.08 | 87.99 | 70.3 | 87.88 | 87.9 | 271.63 | 0.055353 |
| 1 | 0.8572 | | 0.8901 | 0.3625 | 0.3756 | 4513.24 | 5.23 | 86.7 | 67.64 | 86.98 | 87.06 | 273.39 | 0.056892 |
| 1 | 1 | | 0.7771 | 0.3795 | 0.3749 | 4012.97 | -0.58 | 84.88 | 57.82 | 83.32 | 83.39 | 267.11 | 0.047068 |
| 0.5994 | 1 | | 0.6155 | 0.4027 | 0.3835 | 3498.76 | -2.59 | 84.05 | 58.6 | 82.04 | 83.08 | 264.28 | 0.035657 |
| 0.3861 | 1 | | 0.4572 | 0.4294 | 0.3889 | 3003.59 | -5.14 | 83.8 | 63.82 | 81.46 | 83.92 | 258.79 | 0.026288 |
| 0.2601 | 1 | | 0.3731 | 0.4501 | 0.3939 | 2707.9 | -5.47 | 84.39 | 71.14 | 82.35 | 86.2 | 255.29 | 0.020476 |
| 0.1535 | 1 | | 0.2795 | 0.4756 | 0.3975 | 2395.2 | -5.63 | 85.83 | 82.45 | 84.5 | 90.05 | 249.81 | 0.014939 |
| 0.0759 | 1 | | 0.1858 | 0.5044 | 0.3983 | 2098.44 | -5.38 | 88 | 96.9 | 88.69 | 95.8 | 242.46 | 0.010280 |
| 0.0404 | 1 | | 0.0759 | 0.5365 | 0.3909 | 1790.15 | -5.8 | 90.7 | 77.96 | 96.87 | 94.93 | 230.8 | 0.006862 |

FIG. 11D

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 14152.11 | 298.1271 | 134.1939 | 331.8349 | 1.341939 | 101.0002 | 1.54678 | 2678 | 632 | 92.00345 | 11.63 | 80 | 92 |
| 9999.81 | 275.2332 | 119.7487 | 304.6959 | 1.197487 | 101.3572 | 1.422978 | 2292 | 0.620 | 93.9308 | 8.67 | 82 | 93 |
| 8495.97 | 261.752 | 111.2193 | 288.0305 | 1.112193 | 100.1121 | 1.350186 | 2064 | 0.612 | 94.44609 | 7.06 | 83 | 95 |
| 8029.15 | 256.6708 | 108.0529 | 281.4646 | 1.080529 | 99.52996 | 1.322519 | 1981 | 0.608 | 94.66807 | 6.45 | 83 | 95 |
| 6484 | 235.4517 | 94.87325 | 253.1023 | 0.948733 | 95.21015 | 1.206774 | 1633 | 0.590 | 94.77579 | 4.11 | 83 | 96 |
| 5008.17 | 206.6647 | 77.62409 | 211.4532 | 0.776241 | 85.60732 | 1.046733 | 1188 | 0.554 | 94.04487 | 1.85 | 82 | 96 |
| 4513.24 | 194.1684 | 70.28299 | 192.666 | 0.70283 | 79.40875 | 0.976559 | 1001 | 0.530 | 92.69437 | 2.05 | 80 | 95 |
| 4012.97 | 183.8676 | 65.69069 | 175.9327 | 0.656907 | 79.5934 | 0.911741 | 902 | 0.515 | 100.3882 | 2.49 | 81 | 97 |
| 3498.76 | 168.9748 | 57.88474 | 153.3697 | 0.578847 | 72.89898 | 0.823606 | 716 | 0.479 | 104.3856 | 4.15 | 81 | 97 |
| 3003.59 | 152.8215 | 49.9285 | 129.5274 | 0.499285 | 65.69998 | 0.725577 | 1331 | 0.568 | 113.2411 | 6.28 | 83 | 98 |
| 2707.9 | 140.5859 | 43.79486 | 112.0669 | 0.437949 | 58.20584 | 0.651837 | 1190 | 0.554 | 118.101 | 7.87 | 83 | 99 |
| 2395.2 | 125.8012 | 36.68471 | 91.8508 | 0.366847 | 49.10712 | 0.561298 | 1019 | 0.533 | 126.4318 | 10.02 | 85 | 99 |
| 2098.44 | 109.2473 | 29.07006 | 70.64123 | 0.290701 | 39.11959 | 0.458277 | 827 | 0.502 | 139.6268 | 12.77 | 87 | 101 |
| 1790.15 | 89.72556 | 20.9938 | 48.56164 | 0.209938 | 30.97561 | 0.33248 | 601 | 0.448 | 185.2501 | 16.97 | 85 | 107 |

FIG. 11E

| Approximate CCT | Blue, Red, & Green | | Blue, Red, & Cyan | | increase of EML | increase of Ra |
|---|---|---|---|---|---|---|
| | Ra | EML | Ra | EML | | |
| 10000 | 92.2 | 1.339897 | 89.64 | 1.422978 | 6% | 2.56 |
| 8000 | 91.85 | 1.215116 | 89.58 | 1.322519 | 9% | 2.27 |
| 6500 | 94.23 | 1.0917 | 89.09 | 1.206774 | 11% | 5.14 |
| 5000 | 95.05 | 0.914422 | 87.99 | 1.046733 | 14% | 7.06 |
| 4000 | 96.73 | 0.78765 | 84.88 | 0.911741 | 16% | 11.85 |
| 3500 | 95.52 | 0.713161 | 84.05 | 0.823606 | 15% | 11.47 |
| 3000 | 93.9 | 0.631587 | 83.8 | 0.725577 | 15% | 10.1 |
| 2700 | 93.88 | 0.561254 | 84.39 | 0.651837 | 16% | 9.49 |
| 2400 | 93.88 | 0.487289 | 85.83 | 0.561298 | 15% | 8.05 |
| 2100 | 93.5 | 0.406168 | 88 | 0.458277 | 13% | 5.5 |
| 1800 | 92.86 | 0.305184 | 90.7 | 0.33248 | 9% | 2.16 |

FIG. 12A

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | 0.1376 | | 0.2797 | 0.2869 | 10188.24 | -0.11 | 92.19 | 93.52 | 97.23 | 88.77 | 255.88 |
| 1 | 0 | 0.1987 | | 0.2882 | 0.307 | 8484.09 | 5.2 | 92.04 | 81.24 | 96.07 | 89.11 | 269.27 |
| 1 | 0 | 0.2071 | | 0.2897 | 0.3098 | 8287.03 | 5.76 | 91.85 | 78.99 | 95.46 | 88.82 | 271.03 |
| 1 | 0.0273 | 0.2327 | | 0.2975 | 0.3181 | 7548.23 | 5.67 | 92.68 | 82.52 | 95.9 | 89.88 | 274.26 |
| 1 | 0.0497 | 0.2552 | | 0.3036 | 0.3247 | 7061.67 | 5.74 | 93.21 | 84.34 | 96.08 | 90.53 | 276.77 |
| 1 | 0.0883 | 0.2809 | | 0.312 | 0.3321 | 6515.58 | 5.12 | 94.23 | 89.15 | 97.01 | 91.87 | 278.66 |
| 0.8401 | 0.1147 | 0.2698 | | 0.3214 | 0.3414 | 5997.82 | 5.24 | 94.87 | 90.9 | 97.19 | 92.68 | 281.58 |
| 0.7738 | 0.1535 | 0.2859 | | 0.332 | 0.3515 | 5518.58 | 5.47 | 95.4 | 91.77 | 97.23 | 93.36 | 284.51 |
| 0.6414 | 0.1986 | 0.2859 | | 0.3469 | 0.3644 | 4977.02 | 5.63 | 95.05 | 93.68 | 96.31 | 92.04 | 287.46 |
| 0.525 | 0.2504 | 0.2859 | | 0.3633 | 0.3772 | 4495.7 | 5.68 | 95.93 | 97.03 | 96.99 | 93.35 | 289.4 |
| 0.5218 | 0.3764 | 0.2859 | | 0.381 | 0.3784 | 3995.75 | 0.61 | 96.73 | 88.34 | 96.84 | 94.32 | 282.01 |
| 0.3409 | 0.3829 | 0.2084 | | 0.4031 | 0.3845 | 3496.27 | -2.28 | 95.52 | 83.27 | 94.27 | 92.92 | 276.67 |
| 0.2149 | 0.3829 | 0.1405 | | 0.4291 | 0.3875 | 2997.45 | -5.66 | 93.9 | 82.39 | 91.79 | 91.62 | 268.06 |
| 0.1761 | 0.483 | 0.1405 | | 0.4511 | 0.3941 | 2694.67 | -5.48 | 93.88 | 87.53 | 92.05 | 93.24 | 263.94 |
| 0.1147 | 0.5121 | 0.1082 | | 0.4755 | 0.3971 | 2394.43 | -5.75 | 93.88 | 94.64 | 92.66 | 95.46 | 256.87 |
| 0.063 | 0.5121 | 0.0695 | | 0.5028 | 0.3971 | 2105.02 | -5.78 | 93.5 | 93.46 | 94.61 | 99.06 | 247.41 |
| 0.0242 | 0.5121 | 0.0307 | | 0.5363 | 0.3933 | 1806.76 | -5.13 | 92.86 | 75.5 | 99.1 | 93.61 | 234.5 |

FIG. 12B

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10188.24 | 271.7767 | 117.5123 | 302.2344 | 1.175123 | 102.6789 | 1.339897 | | | 95.67311 | 9.95 | 84 | 94 |
| 8484.09 | 255.2839 | 105.6171 | 285.8989 | 1.056171 | 96.55727 | 1.242974 | | | 93.13028 | 9.4 | 95 | 95 |
| 8287.03 | 0.060652 | 0.024935 | 283.3167 | 1.039844 | | 1.2290 | 1910 | 0.6050 | | 9.3 | 85 | 93 |
| 7548.23 | 0.063043 | 0.025418 | 271.2259 | 0.983768 | | 1.1776 | 1764 | 0.5980 | | 8.24 | 86 | 95 |
| 7061.67 | 0.06512 | 0.025838 | 261.8909 | 0.941295 | | 1.1387 | 1653 | 0.5910 | | 7.48 | 86 | 95 |
| 6515.58 | 0.067603 | 0.026326 | 249.8219 | 0.891874 | | 1.0917 | 1526 | 0.5830 | | 6.39 | 87 | 96 |
| 5997.82 | 219.9086 | 83.55299 | 236.4818 | 0.83553 | 90.96754 | 1.039521 | | | 95.21464 | 5.37 | 88 | 97 |
| 5518.58 | 210.3198 | 77.67346 | 222.115 | 0.776735 | 88.19138 | 0.984503 | | | 95.34702 | 4.34 | 89 | 97 |
| 4977.02 | 198.0732 | 70.30835 | 203.1191 | 0.703084 | 83.93456 | 0.914422 | | | 95.3394 | 3.06 | 89 | 97 |
| 4495.7 | 185.7664 | 63.08259 | 183.4506 | 0.630826 | 78.74207 | 0.844224 | | | 95.07326 | 1.91 | 88 | 97 |
| 3995.75 | 175.5091 | 58.54987 | 165.8751 | 0.585499 | 78.37629 | 0.78765 | | | 102.2301 | 0.8 | 90 | 97 |
| 3496.27 | 162.1604 | 51.98178 | 144.4398 | 0.519818 | 73.78714 | 0.713161 | | | 108.6856 | 2.73 | 91 | 101 |
| 2997.45 | 147.4127 | 45.2754 | 121.8447 | 0.452754 | 68.38171 | 0.631587 | | | 121.0082 | 5.38 | 93 | 103 |
| 2694.67 | 134.8267 | 38.9983 | 103.3136 | 0.389983 | 60.02355 | 0.561254 | | | 125.9038 | 7.19 | 93 | 103 |
| 2394.43 | 121.4557 | 32.90427 | 84.80933 | 0.329043 | 51.51462 | 0.487289 | | | 135.8321 | 9.51 | 93 | 105 |
| 2105.02 | 106.6825 | 26.62673 | 66.07927 | 0.266267 | 42.12676 | 0.406168 | | | 151.9294 | 12.45 | 91 | 106 |
| 1806.76 | 88.16478 | 19.28298 | 45.30811 | 0.19283 | 30.55817 | 0.305184 | | | 181.2621 | 16.55 | 85 | 108 |

FIG. 12C

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) | BLH Factor (µW/cm2/lux) |
|---|---|---|---|---|---|---|---|---|---|---|---|---|---|
| 1 | 0 | | 0.3118 | 0.2763 | 0.2939 | 10146.09 | 5.64 | 78.81 | 64 | 83.25 | 78.2 | 243.18 | 0.04005 |
| 1 | 0.021 | | 0.3409 | 0.2837 | 0.3021 | 9032.55 | 5.31 | 79.31 | 58.51 | 84.12 | 78.14 | 244.85 | 0.040373 |
| 1 | 0.0468 | | 0.3829 | 0.2929 | 0.3125 | 7982.52 | 5.33 | 79.94 | 54.59 | 82.04 | 78.39 | 247.1 | 0.040835 |
| 1 | 0.0662 | | 0.4055 | 0.2984 | 0.3178 | 7492.58 | 5.01 | 80.09 | 51.12 | 81.48 | 78.13 | 247.71 | 0.041088 |
| 1 | 0.1179 | | 0.4863 | 0.3125 | 0.3336 | 6481.37 | 5.67 | 80.98 | 49.53 | 81.52 | 79.05 | 250.74 | 0.041965 |
| 0.6995 | 0.1115 | | 0.3667 | 0.3207 | 0.3404 | 6038.54 | 5.12 | 80.95 | 45.98 | 80.78 | 78.55 | 250.7 | 0.042388 |
| 0.5669 | 0.1147 | | 0.3312 | 0.3289 | 0.3493 | 5648.96 | 5.73 | 81.41 | 46.81 | 81.1 | 79.34 | 252.06 | 0.043029 |
| 0.8417 | 0.2536 | | 0.5669 | 0.3433 | 0.3609 | 5096.58 | 5.35 | 81.46 | 44.72 | 80.44 | 79.09 | 251.74 | 0.043964 |
| 0.399 | 0.1922 | | 0.3279 | 0.3625 | 0.3755 | 4510.53 | 5.13 | 80.6 | 40.6 | 79.66 | 78.37 | 250.65 | 0.045581 |
| 0.5153 | 0.3764 | | 0.4378 | 0.3815 | 0.3784 | 3983.38 | 0.49 | 78.34 | 29.86 | 75.6 | 73.98 | 242.52 | 0.042962 |
| 0.8708 | 0.9095 | | 0.7738 | 0.4004 | 0.3816 | 3535.52 | -2.95 | 76.69 | 25.97 | 72.78 | 71.38 | 235.2 | 0.034629 |
| 0.3861 | 0.6995 | | 0.399 | 0.4309 | 0.389 | 2977.8 | -5.3 | 75.79 | 30.03 | 71.02 | 71.26 | 225.77 | 0.024321 |
| 0.1638 | 0.3893 | | 0.1826 | 0.4461 | 0.3918 | 2749.64 | -5.95 | 75.82 | 34.36 | 70.77 | 72.14 | 220.95 | 0.020361 |
| 0.0856 | 0.3538 | | 0.1212 | 0.4729 | 0.3977 | 2429.68 | -5.48 | 76.83 | 44.58 | 71.67 | 75.25 | 213.64 | 0.014547 |
| 0.1341 | 1 | | 0.2246 | 0.4998 | 0.3981 | 2140.81 | -5.52 | 78.74 | 57.6 | 73.35 | 79.32 | 204.22 | 0.010356 |
| 0.0436 | 1 | | 0.0727 | 0.5416 | 0.3914 | 1757.84 | -5.23 | 84.59 | 84.72 | 79.64 | 89.01 | 187.68 | 0.005978 |

FIG. 12D

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10146.09 | 280.4096 | 125.3847 | 305.5131 | 1.253847 | 99.30193 | 1.547 | 2442 | 0.625 | 90.46827 | 7.29 | 71 | 88 |
| 9032.55 | 270.7351 | 119.1283 | 292.3118 | 1.191283 | 99.0909 | 1.486 | 2275 | 0.620 | 91.37234 | 6.13 | 72 | 90 |
| 7982.52 | 259.3614 | 111.7299 | 276.7259 | 1.117299 | 98.03254 | 1.415 | 2078 | 0.613 | 92.10569 | 4.9 | 73 | 91 |
| 7492.58 | 253.233 | 107.8496 | 267.7989 | 1.078496 | 97.53102 | 1.377 | 1976 | 0.608 | 92.68106 | 4.2 | 73 | 92 |
| 6481.37 | | | | | 94.22 | 1.280 | 1709 | 0.595 | 92.91 | | 75 | 93 |
| 6038.54 | | | | | 92.89 | 1.233 | 1587 | 0.587 | 93.59 | | 75 | 93 |
| 5648.96 | 0.072 | 0.029 | 222.423 | 0.880 | 90.12 | 1.183 | 1452 | 0.578 | 93.20 | 2.45 | 76 | 93 |
| 5096.58 | 0.078 | 0.030 | 203.799 | 0.808 | 86.53 | 1.108 | 1266 | 0.562 | 93.68 | 2.73 | 75 | 94 |
| 4510.53 | 0.089 | 0.033 | 180.402 | 0.717 | 80.18 | 1.015 | 1035 | 0.535 | 93.27 | 3.81 | 74 | 93 |
| 3983.38 | 0.086 | 0.031 | 160.371 | 0.659 | 78.61 | 0.940 | 899 | 0.515 | 99.56 | 4.85 | 75 | 95 |
| 3535.52 | 0.072 | 0.025 | 141.931 | 0.601 | 75.66 | 0.867 | 766 | 0.490 | 106.67 | 6.21 | 76 | 97 |
| 2977.8 | 0.056 | 0.018 | 114.726 | 0.506 | 67.19 | 0.749 | 1368 | 0.571 | 116.88 | 8.49 | 77 | 99 |
| 2749.64 | 0.049 | 0.016 | 102.345 | 0.461 | 62.43 | 0.693 | 1260 | 0.561 | 122.88 | 9.69 | 78 | 100 |
| 2429.68 | 0.039 | 0.012 | 82.142 | 0.382 | 51.99 | 0.595 | 1075 | 0.540 | 129.57 | 11.72 | 79 | 102 |
| 2140.81 | 0.031 | 0.008 | 63.997 | 0.312 | 42.91 | 0.498 | 895 | 0.514 | 144.47 | 14.21 | 82 | 104 |
| 1757.84 | 0.020 | 0.005 | 39.320 | 0.208 | 30.41 | 0.344 | 613 | 0.452 | 194.89 | 19.57 | 84 | 111 |

FIG. 12E

| Approximate CCT | Blue, Red, & Green | | Blue, Red, & Cyan | | increase of EML | increase of Ra |
| --- | --- | --- | --- | --- | --- | --- |
| | Ra | EML | Ra | EML | | |
| 10000 | 92.2 | 1.339897 | 78.81 | 1.547 | 15% | 13.39 |
| 8000 | 91.85 | 1.215116 | 79.94 | 1.415 | 16% | 11.91 |
| 6500 | 94.23 | 1.0917 | 80.98 | 1.280 | 17% | 13.25 |
| 5000 | 95.05 | 0.914422 | 81.46 | 1.108 | 21% | 13.59 |
| 4000 | 96.73 | 0.78765 | 78.34 | 0.940 | 19% | 18.39 |
| 3500 | 95.52 | 0.713161 | 76.69 | 0.867 | 22% | 18.83 |
| 3000 | 93.9 | 0.631587 | 75.79 | 0.749 | 19% | 18.11 |
| 2700 | 93.88 | 0.561254 | 75.82 | 0.693 | 23% | 18.06 |
| 2400 | 93.88 | 0.487289 | 76.83 | 0.595 | 22% | 17.05 |
| 2100 | 93.5 | 0.406168 | 78.74 | 0.498 | 23% | 14.76 |
| 1800 | 92.86 | 0.305184 | 84.59 | 0.344 | 13% | 8.27 |

FIG. 13A

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | 0.1376 | | 0.2797 | 0.2869 | 10188.24 | -0.11 | 92.19 | 93.52 | 97.23 | 88.77 | 255.88 |
| 1 | 0 | 0.1987 | | 0.2882 | 0.307 | 8484.09 | 5.2 | 92.04 | 81.24 | 96.07 | 89.11 | 269.27 |
| 1 | 0 | 0.2071 | | 0.2897 | 0.3098 | 8287.03 | 5.76 | 91.85 | 78.99 | 95.46 | 88.82 | 271.03 |
| 1 | 0.0273 | 0.2327 | | 0.2975 | 0.3181 | 7548.23 | 5.67 | 92.68 | 82.52 | 95.9 | 89.88 | 274.26 |
| 1 | 0.0497 | 0.2552 | | 0.3036 | 0.3247 | 7061.67 | 5.74 | 93.21 | 84.34 | 96.08 | 90.53 | 276.77 |
| 1 | 0.0883 | 0.2809 | | 0.312 | 0.3321 | 6515.58 | 5.12 | 94.23 | 89.15 | 97.01 | 91.87 | 278.66 |
| 0.8401 | 0.1147 | 0.2698 | | 0.3214 | 0.3414 | 5997.82 | 5.24 | 94.87 | 90.9 | 97.19 | 92.68 | 281.58 |
| 0.7738 | 0.1535 | 0.2859 | | 0.332 | 0.3515 | 5518.58 | 5.47 | 95.4 | 91.77 | 97.23 | 93.36 | 284.51 |
| 0.6414 | 0.1986 | 0.2859 | | 0.3469 | 0.3644 | 4977.02 | 5.63 | 95.05 | 93.68 | 96.31 | 92.04 | 287.46 |
| 0.525 | 0.2504 | 0.2859 | | 0.3633 | 0.3772 | 4495.7 | 5.68 | 95.93 | 97.03 | 96.99 | 93.35 | 289.4 |
| 0.5218 | 0.3764 | 0.2859 | | 0.381 | 0.3784 | 3995.75 | 0.61 | 96.73 | 88.34 | 96.84 | 94.32 | 282.01 |
| 0.3409 | 0.3829 | 0.2084 | | 0.4031 | 0.3845 | 3496.27 | -2.28 | 95.52 | 83.27 | 94.27 | 92.92 | 276.67 |
| 0.2149 | 0.3829 | 0.1405 | | 0.4291 | 0.3875 | 2997.45 | -5.66 | 93.9 | 82.39 | 91.79 | 91.62 | 268.06 |
| 0.1761 | 0.483 | 0.1405 | | 0.4511 | 0.3941 | 2694.67 | -5.48 | 93.88 | 87.53 | 92.05 | 93.24 | 263.94 |
| 0.1147 | 0.5121 | 0.1082 | | 0.4755 | 0.3971 | 2394.43 | -5.75 | 93.88 | 94.64 | 92.66 | 95.46 | 256.87 |
| 0.063 | 0.5121 | 0.0695 | | 0.5028 | 0.3971 | 2105.02 | -5.78 | 93.5 | 93.46 | 94.61 | 99.06 | 247.41 |
| 0.0242 | 0.5121 | 0.0307 | | 0.5363 | 0.3933 | 1806.76 | -5.13 | 92.86 | 75.5 | 99.1 | 93.61 | 234.5 |

FIG. 13B

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 10188.24 | 271.7767 | 117.5123 | 302.2344 | 1.175123 | 102.6789 | 1.339897 | | | 95.67311 | 9.95 | 84 | 94 |
| 8484.09 | 255.2839 | 105.6171 | 285.8989 | 1.056171 | 96.55727 | 1.242974 | | | 93.13028 | 9.4 | 95 | 95 |
| 8287.03 | 0.060652 | 0.024935 | 283.3167 | 1.039844 | | 1.2290 | 1910 | 0.6050 | | 9.3 | 85 | 93 |
| 7548.23 | 0.063043 | 0.025418 | 271.2259 | 0.983768 | | 1.1776 | 1764 | 0.5980 | | 8.24 | 86 | 95 |
| 7061.67 | 0.06512 | 0.025838 | 261.8909 | 0.941295 | | 1.1387 | 1653 | 0.5910 | | 7.48 | 86 | 95 |
| 6515.58 | 0.067603 | 0.026326 | 249.8219 | 0.891874 | | 1.0917 | 1526 | 0.5830 | | 6.39 | 87 | 96 |
| 5997.82 | 219.9086 | 83.55299 | 236.4818 | 0.83553 | 90.96754 | 1.039521 | | | 95.21464 | 5.37 | 88 | 97 |
| 5518.58 | 210.3198 | 77.67346 | 222.115 | 0.776735 | 88.19138 | 0.984503 | | | 95.34702 | 4.34 | 89 | 97 |
| 4977.02 | 198.0732 | 70.30835 | 203.1191 | 0.703084 | 83.93456 | 0.914422 | | | 95.3394 | 3.06 | 89 | 97 |
| 4495.7 | 185.7664 | 63.08259 | 183.4506 | 0.630826 | 78.74207 | 0.844224 | | | 95.07326 | 1.91 | 88 | 97 |
| 3995.75 | 175.5091 | 58.54987 | 165.8751 | 0.585499 | 78.37629 | 0.78765 | | | 102.2301 | 0.8 | 90 | 97 |
| 3496.27 | 162.1604 | 51.98178 | 144.4398 | 0.519818 | 73.78714 | 0.713161 | | | 108.6856 | 2.73 | 91 | 101 |
| 2997.45 | 147.4127 | 45.2754 | 121.8447 | 0.452754 | 68.38171 | 0.631587 | | | 121.0082 | 5.38 | 93 | 103 |
| 2694.67 | 134.8267 | 38.9983 | 103.3136 | 0.389983 | 60.02355 | 0.561254 | | | 125.9038 | 7.19 | 93 | 103 |
| 2394.43 | 121.4557 | 32.90427 | 84.80933 | 0.329043 | 51.51462 | 0.487289 | | | 135.8321 | 9.51 | 93 | 105 |
| 2105.02 | 106.6825 | 26.62673 | 66.07927 | 0.266267 | 42.12676 | 0.406168 | | | 151.9294 | 12.45 | 91 | 106 |
| 1806.76 | 88.16478 | 19.28298 | 45.30811 | 0.19283 | 30.55817 | 0.305184 | | | 181.2621 | 16.55 | 85 | 108 |

FIG. 13C

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) | BLH Factor (μW/cm2/lux) |
|---|---|---|---|---|---|---|---|---|---|---|---|---|---|
| 1 | 0.05 | | 0.2569 | 0.2783 | 0.2965 | 9804.25 | 5.73 | 87.11 | 34.54 | | | 281.95 | |
| 1 | 0.1147 | | 0.3053 | 0.2874 | 0.3066 | 8561.51 | 5.44 | 90.77 | 53.75 | | | 286.89 | |
| 1 | 0.1502 | | 0.3376 | 0.2922 | 0.3126 | 8027.91 | 5.79 | 92.34 | 60.8 | 93.25 | 90.17 | 289.87 | 0.045776 |
| 0.8966 | 0.2246 | | 0.3764 | 0.3037 | 0.3261 | 7038.68 | 6.38 | 95.82 | 76.07 | 96.7 | 94.12 | 296.2 | 0.046717 |
| 0.8449 | 0.2924 | | 0.399 | 0.3124 | 0.3334 | 6484.24 | 5.59 | 97.78 | 89.05 | 98.23 | 96.86 | 299.15 | 0.047299 |
| 0.6898 | 0.3118 | | 0.3764 | 0.3211 | 0.3423 | 6012.52 | 5.89 | 97.29 | 96.23 | 96.42 | 96.44 | 302.96 | 0.04811 |
| 0.9128 | 0.5315 | | 0.5703 | 0.33 | 0.3505 | 5602.88 | 5.84 | 95.39 | 93.79 | 93.95 | 94.42 | 306.19 | 0.048961 |
| 0.7027 | 0.6349 | | 0.5703 | 0.3471 | 0.3653 | 4970.86 | 5.95 | 91.55 | 82.17 | 89.41 | 90.22 | 311.76 | 0.043687 |
| 0.2536 | 0.3376 | | 0.2601 | 0.3634 | 0.3769 | 4491.61 | 5.49 | 87.44 | 70.9 | 84.81 | 85.86 | 315.53 | 0.033693 |
| 0.5089 | 0.9354 | | 0.5638 | 0.3797 | 0.3774 | 4026.34 | 0.57 | 82.24 | 55.79 | 77.9 | 78.25 | 313.55 | 0.027014 |
| 0.2052 | 0.5994 | | 0.2892 | 0.4024 | 0.3839 | 3508.05 | -2.38 | 76.95 | 47.71 | 71.04 | 72.63 | 313.7 | 0.019943 |
| 0.1567 | 0.8352 | | 0.3118 | 0.431 | 0.389 | 2975.14 | -5.32 | 71.62 | 46.67 | 63.86 | 68.79 | 312.4 | 0.01391 |

FIG. 13D

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 9804.25 | | | | | | | | | | | | |
| 8561.51 | | | | | | | | | | | | |
| 8027.91 | 0.060 | 0.024 | 292.808 | 0.998 | 98.43 | 1.153 | 1780.000 | 0.599 | 95.90 | 10.42 | 88 | 98 |
| 7038.68 | 0.065 | 0.025 | 277.915 | 0.928 | 97.74 | 1.108 | 1590.000 | 0.587 | 97.11 | 8 | 91 | 100 |
| 6484.24 | 0.068 | 0.026 | 267.870 | 0.887 | 97.77 | 1.078 | 1479.000 | 0.580 | 98.59 | 6.31 | 92 | 101 |
| 6012.52 | 0.072 | 0.027 | 257.960 | 0.844 | 96.08 | 1.049 | 1363.000 | 0.570 | 98.71 | 4.89 | 92 | 102 |
| 5602.88 | 0.077 | 0.029 | 248.012 | 0.803 | 94.34 | 1.020 | 1255.000 | 0.560 | 99.01 | 3.49 | 91 | 102 |
| 4970.86 | 0.075 | 0.027 | 229.882 | 0.732 | 89.61 | 0.969 | 1067.000 | 0.539 | 98.59 | 1.23 | 88 | 102 |
| 4491.61 | 0.062 | 0.022 | 213.984 | 0.674 | 84.62 | 0.924 | 915.000 | 0.517 | 98.13 | 1.05 | 85 | 101 |
| 4026.34 | 0.051 | 0.018 | 200.851 | 0.637 | 84.48 | 0.881 | 831.000 | 0.503 | 104.97 | 3.03 | 83 | 103 |
| 3508.05 | 0.041 | 0.014 | 181.853 | 0.577 | 78.93 | 0.822 | 686.000 | 0.471 | 110.51 | 5.56 | 79 | 104 |
| 2975.14 | 0.031 | 0.010 | 159.291 | 0.508 | 70.69 | 0.749 | 1363.000 | 0.570 | 120.33 | 8.66 | 76 | 105 |

FIG. 13E

| Approximate CCT | Blue, Red, & Green | | Blue, Red, & Cyan | | | |
|---|---|---|---|---|---|---|
| | Ra | EML | Ra | EML | increase of EML | increase of Ra |
| 10000 | 92.2 | 1.339897 | 87.11 | | | 5.09 |
| 8000 | 91.85 | 1.215116 | 92.34 | 1.153 | -5% | -0.49 |
| 6500 | 94.23 | 1.0917 | 97.78 | 1.078 | -1% | -3.55 |
| 5000 | 95.05 | 0.914422 | 91.55 | 0.969 | 6% | 3.5 |
| 4000 | 96.73 | 0.78765 | 82.24 | 0.881 | 12% | 14.49 |
| 3500 | 95.52 | 0.713161 | 76.95 | 0.822 | 15% | 18.57 |
| 3000 | 93.9 | 0.631587 | 71.62 | 0.749 | 19% | 22.28 |

FIG. 14A

| Blue Channel Relative Intensity | Red Channel Relative Intensity | Green Channel Relative Intensity | Cyan Channel Relative Intensity | ccx | ccy | CCT | duv | Ra | R9 | R13 | R15 | LER (luminous efficacy of radiation) (lm/W) | COI | CLA | CS |
|---|---|---|---|---|---|---|---|---|---|---|---|---|---|---|---|
| 1 | 0.0339 | 0 | 0.4023 | 0.2933 | 0.3135 | 7931.21 | 5.68 | 91.61 | 70.84 | 91.84 | 90.51 | 275.05 | 9.38 | 1746 | 0.597 |
| 0.8449 | 0.1018 | 0.0242 | 0.4055 | 0.3129 | 0.3333 | 6463.2 | 5.35 | 94.45 | 90.6 | 96.3 | 96.55 | 275.19 | 5.81 | 1430 | 0.576 |
| 0.6543 | 0.0792 | 0 | 0.2955 | 0.3209 | 0.3407 | 6024.95 | 5.13 | 93.01 | 84.77 | 94.07 | 93.93 | 279.56 | 5.66 | 1311 | 0.566 |
| 0.8384 | 0.0985 | 0.1341 | 0.3506 | 0.3312 | 0.3518 | 5552.28 | 5.97 | 90.58 | 73.58 | 90.82 | 90.25 | 286.63 | 5.32 | 1131 | 0.547 |
| 0.4863 | 0.0889 | 0.1115 | 0.2052 | 0.3462 | 0.363 | 4997.1 | 5.2 | 91.16 | 78.81 | 91.53 | 91.47 | 286.58 | 3.63 | 956 | 0.524 |
| 0.6026 | 0.2504 | 0.1373 | 0.3667 | 0.3634 | 0.3759 | 4485.68 | 5.02 | 95.06 | 96.27 | 97.7 | 98.53 | 277.13 | 1.32 | 810 | 0.499 |
| 1 | 0.3473 | 0.4152 | 0.3118 | 0.3772 | 0.3745 | 4073.17 | -0.08 | 90.93 | 91.26 | 94.12 | 96.66 | 280.4 | 0.87 | 684 | 0.471 |
| 0.8578 | 0.6349 | 0.454 | 0.3247 | 0.404 | 0.3834 | 3467.6 | -2.94 | 92.63 | 90.11 | 98.85 | 95.45 | 266.14 | 3.00 | 508 | 0.418 |
| 0.5444 | 0.6349 | 0.3764 | 0.1826 | 0.427 | 0.3863 | 3023.73 | -5.88 | 92.19 | 85.42 | 95.93 | 92.44 | 254.8 | 5.57 | 1024 | 0.534 |
| 0.4766 | 0.7415 | 0.5121 | 0.0404 | 0.4498 | 0.3933 | 2706.32 | -5.69 | 91.9 | 96.92 | 98.64 | 95.79 | 252.44 | 7.17 | 833 | 0.503 |
| 0.2666 | 0.8869 | 0.4249 | 0.0468 | 0.4763 | 0.3973 | 2386.25 | -5.7 | 92.72 | 92.51 | 94.89 | 93.66 | 237.16 | 10.36 | 728 | 0.481 |
| 0.1341 | 0.9095 | 0.3635 | 0 | 0.5003 | 0.3972 | 2129.89 | -5.81 | 93.17 | 96.64 | 93.96 | 94.55 | 225.01 | 13.06 | 616 | 0.453 |
| 0 | 1 | 0.273 | 0 | 0.5311 | 0.3941 | 1848.99 | -5.3 | 92.71 | 95.71 | 91.55 | 96.05 | 206.77 | 17.36 | 505 | 0.417 |

FIG. 14B

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | 0.6414 | | 0.3732 | 0.3838 | 4246.95 | 5.48 | 76.14 | 28.02 | 75.81 | 75.57 | 316.1 |
| 0.8126 | 0.0953 | 0.4992 | | 0.3807 | 0.3771 | 3994.63 | 0.1 | 80.19 | 52.15 | 81.6 | 83.92 | 300.14 |
| 0.6931 | 0.2407 | 0.4895 | | 0.4012 | 0.3826 | 3525.22 | -2.68 | 84.42 | 73.43 | 87.76 | 91.48 | 285.51 |
| 0.4701 | 0.4507 | 0.4152 | | 0.4339 | 0.3863 | 2901.59 | -6.82 | 90.06 | 95.9 | 96.37 | 97.2 | 260.74 |
| 0.4346 | 0.5961 | 0.4669 | | 0.448 | 0.3926 | 2728.12 | -5.81 | 91.08 | 97.82 | 97.79 | 96.9 | 255.42 |
| 0.1986 | 0.525 | 0.3053 | | 0.4721 | 0.398 | 2442 | -5.34 | 92.4 | 97.64 | 97.76 | 95.61 | 242.94 |
| 0.1309 | 0.9031 | 0.3635 | | 0.5006 | 0.3977 | 2129.96 | -5.64 | 93.21 | 96.86 | 94.12 | 94.69 | 225.25 |
| 0.0112 | 1 | 0.273 | | 0.5298 | 0.3926 | 1849.65 | -5.83 | 92.67 | 95.73 | 91.57 | 95.89 | 206.51 |

FIG. 14C

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 4246.95 | | | | | | 0.592 | 556 | 0.435 | | 4.92 | 74 | 99 |
| 3994.63 | | | | | | 0.585 | 568 | 0.438 | | 3.2 | 75 | 102 |
| 3525.22 | | | | | | 0.540 | 451 | 0.396 | | 1.83 | 78 | 105 |
| 2901.59 | | | | | | 0.472 | 884 | 0.512 | | 5.57 | 80 | 110 |
| 2728.12 | | | | | | 0.440 | 818 | 0.500 | | 6.81 | 80 | 111 |
| 2442 | | | | | | 0.391 | 718 | 0.479 | | 9.46 | 81 | 113 |
| 2129.96 | | | | | | 0.337 | 613 | 0.452 | | 13.04 | 80 | 116 |
| 1849.65 | | | | | | 0.283 | 511 | 0.419 | | 17.27 | 77 | 120 |

FIG. 14D

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | | 0.3731 | 0.2853 | 0.3058 | 8762.13 | 6.31 | 89.58 | 57.08 | | | 275.74 |
| 0.706 | 0 | | 0.2924 | 0.2927 | 0.3146 | 7950.44 | 6.54 | 91.55 | 68.82 | | | 275.65 |
| 0.6995 | 0.0404 | | 0.3021 | 0.2972 | 0.318 | 7570.67 | 5.79 | 92.93 | 78.35 | | | 274.18 |
| 0.7771 | 0.11 | | 0.412 | 0.3114 | 0.3346 | 6531.49 | 6.72 | 95.51 | 93.73 | 96.95 | 96.96 | 273.86 |
| 0.8611 | 0.1729 | | 0.5024 | 0.32 | 0.3418 | 6065.84 | 6.12 | 96.08 | 95.17 | 98.43 | 98.83 | 271.73 |
| 0.5638 | 0.1826 | | 0.3893 | 0.3341 | 0.3536 | 5435.84 | 5.61 | 95 | 81.84 | 96.3 | 95.49 | 268.52 |
| 0.4313 | 0.1922 | | 0.3441 | 0.3451 | 0.363 | 5036.18 | 5.64 | 93.47 | 74.75 | 94.12 | 93.14 | 266.32 |
| 0.7674 | 0.4637 | | 0.6801 | 0.3571 | 0.3682 | 4644.53 | 3.58 | 90.71 | 61.3 | 90.18 | 88.49 | 260.96 |
| 0.7221 | 0.7383 | | 0.8028 | 0.38 | 0.3775 | 4018.09 | 0.49 | 85.45 | 44.69 | 83.75 | 81.35 | 251.4 |
| 0.5574 | 0.832 | | 0.7027 | 0.3991 | 0.3786 | 3540.03 | -3.99 | 81.03 | 33.98 | 77.85 | 75.3 | 240.55 |
| 0.2181 | 0.6606 | | 0.4184 | 0.4298 | 0.3867 | 2976.19 | -6.11 | 76.72 | 31.56 | 72.27 | 72.08 | 228.3 |
| 0.3312 | 0.6737 | | 0.496 | 0.4566 | 0.395 | 2721.45 | -5.58 | 74.39 | 35.59 | 70.28 | 72.24 | 219.59 |

FIG. 14E

| CCT | Circadian Power (mW) | Circadian Flux | CER (Circadian power per flux) (blm/W) | CAF (circadian action factor) (blm/lm) | GAI | EML | CLA | CS | GAIBB | COI | Rf | Rg |
|---|---|---|---|---|---|---|---|---|---|---|---|---|
| 8762.13 | | | | | | | | | | | | |
| 7950.44 | | | | | | | | | | | | |
| 7570.67 | | | | | | | | | | | | |
| 6531.49 | | | | | | 1.055 | 1445 | 0.577 | | 5.57 | 94 | 102 |
| 6065.84 | | | | | | 1.026 | 1342 | 0.569 | | 4.25 | 94 | 103 |
| 5435.84 | | | | | | 0.979 | 1179 | 0.553 | | 2.39 | 94 | 104 |
| 5036.18 | | | | | | 0.943 | 1058 | 0.538 | | 1.79 | 92 | 104 |
| 4644.53 | | | | | | 0.908 | 964 | 0.525 | | 2.09 | 90 | 104 |
| 4018.09 | | | | | | 0.844 | 795 | 0.496 | | 3.2 | 87 | 105 |
| 3540.03 | | | | | | 0.792 | 694 | 0.473 | | 5.98 | 85 | 107 |
| 2976.19 | | | | | | 0.712 | 1302 | 0.565 | | 8.84 | 82 | 108 |
| 2721.45 | | | | | | 0.663 | 1204 | 0.555 | | 10.37 | 80 | 107 |

FIG. 14F

| Approximate CCT | Blue, Red, & Green | | Blue, Red, & Cyan | | increase of EML w/ Cyan Channel Replacing Green Channel | Blue, Red, Green, & Cyan | | increase of Ra w/ 4 channels vs. Blue, Red, & Green |
|---|---|---|---|---|---|---|---|---|
| | Ra | EML | Ra | EML | | Ra | EML | |
| 4000 | 80.19 | 0.585 | 85.45 | 0.844 | 44% | 90.93 | 0.692 | 5.48 |
| 3500 | 84.42 | 0.540 | 81.03 | 0.792 | 47% | 92.63 | 0.623 | 11.6 |
| 3000 | 90.06 | 0.472 | 76.72 | 0.712 | 51% | 92.19 | 0.551 | 15.47 |
| 2700 | 91.08 | 0.440 | 74.39 | 0.663 | 51% | 91.9 | 0.450 | 17.51 |

FIG. 15A

| Blue Channel Relative Intensity | Red Channel Relative Intensity | Green Channel Relative Intensity | Cyan Channel Relative Intensity | ccx | ccy | CCT | duv | Ra | R9 | R13 | R15 | LER (luminous efficacy of radiation) (lm/W) | COI | CLA | CS | EML |
|---|---|---|---|---|---|---|---|---|---|---|---|---|---|---|---|---|
| 1 | 0 | 0 | 0.3667 | 0.2855 | 0.3047 | 8784.32 | 5.62 | 89.79 | 59.41 | 89.72 | 87.8 | 274.9 | 11.06 | 1876 | 0.604 | 1.167 |
| 1 | 0.0339 | 0 | 0.399 | 0.2926 | 0.3118 | 8024.27 | 5.16 | 91.9 | 73 | 92.41 | 91.4 | 273.82 | 9.35 | 1762 | 0.598 | 1.136 |
| 1 | 0.0598 | 0 | 0.4313 | 0.2979 | 0.3182 | 7520.91 | 5.48 | 93.11 | 79.95 | 93.8 | 93.1 | 273.85 | 8.21 | 1668 | 0.592 | 1.112 |
| 1 | 0.2052 | 0 | 0.4087 | 0.3118 | 0.3342 | 6513.44 | 6.33 | 95.31 | 88.73 | 95.59 | 94.52 | 272.78 | 6.09 | 1449 | 0.577 | 1.048 |
| 1 | 0.2246 | 0.0404 | 0.4346 | 0.3219 | 0.3429 | 5971.36 | 5.77 | 95.96 | 92.96 | 96.66 | 95.96 | 274.14 | 4.91 | 1310 | 0.566 | 0.998 |
| 0.7124 | 0.1179 | 0.0856 | 0.2859 | 0.3284 | 0.3485 | 5674.55 | 5.63 | 93.91 | 82.72 | 94.36 | 93.7 | 280.07 | 4.99 | 1208 | 0.556 | 0.947 |
| 0.8708 | 0.1308 | 0.2116 | 0.3603 | 0.3452 | 0.3628 | 5030.37 | 5.47 | 93.03 | 79.08 | 93.42 | 92.84 | 284.84 | 3.70 | 993 | 0.529 | 0.861 |
| 0.7318 | 0.0889 | 0.2955 | 0.3021 | 0.3623 | 0.3761 | 4520.68 | 5.49 | 92.25 | 77.15 | 92.18 | 91.26 | 289.35 | 2.57 | 791 | 0.495 | 0.775 |
| 0.7964 | 0.0985 | 0.4475 | 0.2472 | 0.3809 | 0.3774 | 3991.84 | 0.18 | 92.31 | 84.12 | 94.05 | 95.3 | 284.32 | 1.06 | 668 | 0.467 | 0.693 |
| 0.8772 | 0.2439 | 0.6187 | 0.2795 | 0.4017 | 0.3829 | 3516.21 | -2.65 | 94.22 | 95.17 | 97.69 | 99.86 | 274.81 | 1.95 | 530 | 0.426 | 0.629 |
| 0.4443 | 0.1729 | 0.4733 | 0.0792 | 0.4311 | 0.3882 | 2966.56 | -5.66 | 92.96 | 91.07 | 97.09 | 98.94 | 267.1 | 4.75 | 957 | 0.524 | 0.513 |
| 0.2827 | 0.3247 | 0.3376 | 0.1341 | 0.4481 | 0.3938 | 2736.08 | -5.34 | 94.29 | 90.95 | 94.73 | 93.54 | 251.43 | 7.08 | 939 | 0.521 | 0.510 |
| 0.2633 | 0.3796 | 0.538 | 0.0436 | 0.4777 | 0.3989 | 2381.85 | -5.17 | 94.46 | 91.3 | 98.93 | 98.4 | 247.42 | 9.41 | 711 | 0.478 | 0.388 |
| 0.0372 | 0.1082 | 0.1179 | 0 | 0.5028 | 0.3991 | 2118.82 | -5.14 | 94.41 | 86.77 | 98.89 | 98.25 | 234.77 | 12.37 | 582 | 0.443 | 0.319 |
| 0 | 0.1082 | 0.0565 | 0 | 0.5426 | 0.3917 | 1752.2 | -5.08 | 94.58 | 81.56 | 96.45 | 97.46 | 206.71 | 18.44 | 443 | 0.392 | 0.245 |

FIG. 15B

| Blue Channel Relative Intensity | Red Channel Relative Intensity | Green Channel Relative Intensity | Cyan Channel OFF | ccx | ccy | CCT | duv | Ra | R9 | R13 | R15 | LER (luminous efficacy of radiation) (lm/W) | EML | CLA | CS | COI | Rf | Rg |
|---|---|---|---|---|---|---|---|---|---|---|---|---|---|---|---|---|---|---|
| 0.9192 | 0 | 1 | | 0.4226 | 0.3859 | 3102.17 | -5.38 | 86.41 | 69.93 | 89.41 | 92.34 | 282.19 | 0.490 | 923 | 0.519 | 3.5 | 79 | 105 |
| 0.5153 | 0.2213 | 0.7544 | | 0.4531 | 0.3928 | 2654.03 | -6.16 | 90.05 | 81.52 | 94.16 | 96.34 | 263.95 | 0.422 | 786 | 0.494 | 6.6 | 80 | 108 |
| 0.3183 | 0.3021 | 0.6026 | | 0.4734 | 0.3967 | 2415.98 | -5.83 | 91.87 | 84.42 | 96.48 | 97.48 | 252.67 | 0.377 | 696 | 0.474 | 8.82 | 80 | 111 |
| 0.189 | 0.4927 | 0.5477 | | 0.5009 | 0.397 | 2121.68 | -5.88 | 94.2 | 86.38 | 98.84 | 98.2 | 234.68 | 0.321 | 587 | 0.444 | 12.37 | 79 | 114 |
| 0 | 0.1082 | 0.0565 | | 0.5426 | 0.3917 | 1752.2 | -5.08 | 94.58 | 81.56 | 96.45 | 97.46 | 206.71 | 0.230 | 414 | 0.379 | 19.26 | 73 | 120 |

FIG. 15C

| Blue Channel Relative Intensity | Red Channel Relative Intensity | Green Channel OFF | Cyan Channel Relative Intensity | ccx | ccy | CCT | duv | Ra | R9 | R13 | R15 | LER (luminous efficacy of radiation) (lm/W) |
|---|---|---|---|---|---|---|---|---|---|---|---|---|
| 1 | 0 | | 0.3667 | 0.2855 | 0.3047 | 8784.32 | 5.62 | 89.79 | 59.41 | 89.72 | 87.8 | 274.9 |
| 1 | 0.0339 | | 0.399 | 0.2926 | 0.3118 | 8024.27 | 5.16 | 91.9 | 73 | 92.41 | 91.4 | 273.82 |
| 1 | 0.0598 | | 0.4313 | 0.2979 | 0.3182 | 7520.91 | 5.48 | 93.11 | 79.95 | 93.8 | 93.1 | 273.85 |
| 0.7771 | 0.11 | | 0.412 | 0.3114 | 0.3346 | 6531.49 | 6.72 | 95.51 | 93.73 | 96.95 | 96.96 | 273.86 |
| 0.8611 | 0.1729 | | 0.5024 | 0.32 | 0.3418 | 6065.84 | 6.12 | 96.08 | 95.17 | 98.43 | 98.83 | 271.73 |
| 0.5638 | 0.1826 | | 0.3893 | 0.3341 | 0.3536 | 5435.84 | 5.61 | 95 | 81.84 | 96.3 | 95.49 | 268.52 |
| 0.4313 | 0.1922 | | 0.3441 | 0.3451 | 0.363 | 5036.18 | 5.64 | 93.47 | 74.75 | 94.12 | 93.14 | 266.32 |
| 0.7674 | 0.4637 | | 0.6801 | 0.3571 | 0.3682 | 4644.53 | 3.58 | 90.71 | 61.3 | 90.18 | 88.49 | 260.96 |
| 0.7221 | 0.7383 | | 0.8028 | 0.38 | 0.3775 | 4018.09 | 0.49 | 85.45 | 44.69 | 83.75 | 81.35 | 251.4 |
| 0.5574 | 0.832 | | 0.7027 | 0.3991 | 0.3786 | 3540.03 | -3.99 | 81.03 | 33.98 | 77.85 | 75.3 | 240.55 |
| 0.2181 | 0.6606 | | 0.4184 | 0.4298 | 0.3867 | 2976.19 | -6.11 | 76.72 | 31.56 | 72.27 | 72.08 | 228.3 |
| 0.147 | 0.8384 | | 0.4637 | 0.4491 | 0.3939 | 2721.65 | -5.39 | 75.03 | 34.12 | 70.28 | 72.24 | 222.55 |

FIG. 15D

| CCT | Circadian Power (mW) | Circadian Flux | CER (Circadian power per flux) (blm/W) | CAF (circadian action factor) (blm/lm) | GAI | EML | CLA | CS | GAI BB | COI | Rf | Rg |
|---|---|---|---|---|---|---|---|---|---|---|---|---|
| 8784.32 | | | | | | 1.167 | 1876 | 0.604 | | 11.06 | 88 | 99 |
| 8024.27 | | | | | | 1.136 | 1762 | 0.598 | | 9.35 | 90 | 100 |
| 7520.91 | | | | | | 1.112 | 1668 | 0.592 | | 8.21 | 91 | 101 |
| 6531.49 | | | | | | 1.055 | 1445 | 0.577 | | 5.57 | 94 | 102 |
| 6065.84 | | | | | | 1.026 | 1342 | 0.569 | | 4.25 | 94 | 103 |
| 5435.84 | | | | | | 0.979 | 1179 | 0.553 | | 2.39 | 94 | 104 |
| 5036.18 | | | | | | 0.943 | 1058 | 0.538 | | 1.79 | 92 | 104 |
| 4644.53 | | | | | | 0.908 | 964 | 0.525 | | 2.09 | 90 | 104 |
| 4018.09 | | | | | | 0.844 | 795 | 0.496 | | 4.07 | 87 | 105 |
| 3540.03 | | | | | | 0.792 | 694 | 0.473 | | 5.98 | 85 | 107 |
| 2976.19 | | | | | | 0.712 | 1302 | 0.565 | | 8.84 | 82 | 108 |
| 2721.65 | | | | | | 0.663 | 1204 | 0.555 | | 10.37 | 80 | 107 |

FIG. 15E

| Approximate CCT | Blue, Red, & Green | | Blue, Red, & Cyan | | increase of EML w/ Cyan Channel Replacing Green Channel | Blue, Red, Green, & Cyan | | increase of Ra w/ 4 channels vs. Blue, Red, & Green |
|---|---|---|---|---|---|---|---|---|
| | Ra | EML | Ra | EML | | Ra | EML | |
| 3000 | 86.41 | 0.490 | 76.72 | 0.712 | 45% | 92.96 | 0.513 | 6.55 |
| 2700 | 90.05 | 0.422 | 75.03 | 0.663 | 57% | 94.29 | 0.510 | 4.24 |

MULTI-CHANNEL SYSTEMS FOR PROVIDING TUNABLE LIGHT WITH HIGH COLOR RENDERING AND BIOLOGICAL EFFECTS

CROSS-REFERENCE TO RELATED APPLICATIONS

This application is a continuation of U.S. application Ser. No. 16/927,564, filed Jul. 13, 2020, now U.S. Pat. No. 11,371,660, issued Jun. 28, 2022, which is a continuation of International Application No, PCT/US18/20792, filed Mar. 2, 2018, which claims the benefit of U.S. Provisional Patent Application No. 62/616,401 filed Jan. 11, 2018; U.S. Provisional Patent Application No. 62/616,404 filed Jan. 11, 2018; U.S. Provisional Patent Application No. 62/616,414 filed Jan. 11, 2018; U.S. Provisional Patent Application No. 62/616,423 filed Jan. 11, 2018; and U.S. Provisional Patent Application No. 62/634,798 filed Feb. 23, 2018, the contents of which are incorporated by reference herein in their entirety as if fully set forth herein.

FIELD OF THE DISCLOSURE

This disclosure is in the field of solid-state lighting. In particular, the disclosure relates to devices for use in, and methods of, providing tunable white light with high color rendering performance.

BACKGROUND

A wide variety of light emitting devices are known in the art including, for example, incandescent light bulbs, fluorescent lights, and semiconductor light emitting devices such as light emitting diodes ("LEDs").

There are a variety of resources utilized to describe the light produced from a light emitting device, one commonly used resource is 1931 CIE (Commission Internationale de l'Éclairage) Chromaticity Diagram. The 1931 CIE Chromaticity Diagram maps out the human color perception in terms of two CIE parameters x and y. The spectral colors are distributed around the edge of the outlined space, which includes all of the hues perceived by the human eye. The boundary line represents maximum saturation for the spectral colors, and the interior portion represents less saturated colors including white light. The diagram also depicts the Planckian locus, also referred to as the black body locus (BBL), with correlated color temperatures, which represents the chromaticity coordinates (i.e., color points) that correspond to radiation from a black-body at different temperatures. Illuminants that produce light on or near the BBL can thus be described in terms of their correlated color temperatures (CCT). These illuminants yield pleasing "white light" to human observers, with general illumination typically utilizing CCT values between 1,800K and 10,000K.

Color rendering index (CRI) is described as an indication of the vibrancy of the color of light being produced by a light source. In practical terms, the CRI is a relative measure of the shift in surface color of an object when lit by a particular lamp as compared to a reference light source, typically either a black-body radiator or the daylight spectrum. The higher the CRI value for a particular light source, the better that the light source renders the colors of various objects it is used to illuminate.

Color rendering performance may be characterized via standard metrics known in the art. Fidelity Index (Rf) and the Gamut Index (Rg) can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. In practical terms, the Rf is a relative measure of the shift in surface color of an object when lit by a particular lamp as compared to a reference light source, typically either a black-body radiator or the daylight spectrum. The higher the Rf value for a particular light source, the better that the light source renders the colors of various objects it is used to illuminate. The Gamut Index Rg evaluates how well a light source saturates or desaturates the 99 CES compared to the reference source.

LEDs have the potential to exhibit very high power efficiencies relative to conventional incandescent or fluorescent lights. Most LEDs are substantially monochromatic light sources that appear to emit light having a single color. Thus, the spectral power distribution of the light emitted by most LEDs is tightly centered about a "peak" wavelength, which is the single wavelength where the spectral power distribution or "emission spectrum" of the LED reaches its maximum as detected by a photo-detector. LEDs typically have a full-width half-maximum wavelength range of about 10 nm to 30 nm, comparatively narrow with respect to the broad range of visible light to the human eye, which ranges from approximately from 380 nm to 800 nm.

In order to use LEDs to generate white light, LED lamps have been provided that include two or more LEDs that each emit a light of a different color. The different colors combine to produce a desired intensity and/or color of white light. For example, by simultaneously energizing red, green and blue LEDs, the resulting combined light may appear white, or nearly white, depending on, for example, the relative intensities, peak wavelengths and spectral power distributions of the source red, green and blue LEDs. The aggregate emissions from red, green, and blue LEDs typically provide poor color rendering for general illumination applications due to the gaps in the spectral power distribution in regions remote from the peak wavelengths of the LEDs.

White light may also be produced by utilizing one or more luminescent materials such as phosphors to convert some of the light emitted by one or more LEDs to light of one or more other colors. The combination of the light emitted by the LEDs that is not converted by the luminescent material (s) and the light of other colors that are emitted by the luminescent material(s) may produce a white or near-white light.

LED lamps have been provided that can emit white light with different CCT values within a range. Such lamps utilize two or more LEDs, with or without luminescent materials, with respective drive currents that are increased or decreased to increase or decrease the amount of light emitted by each LED. By controllably altering the power to the various LEDs in the lamp, the overall light emitted can be tuned to different CCT values. The range of CCT values that can be provided with adequate color rendering values and efficiency is limited by the selection of LEDs.

The spectral profiles of light emitted by white artificial lighting can impact circadian physiology, alertness, and cognitive performance levels. Bright artificial light can be used in a number of therapeutic applications, such as in the treatment of seasonal affective disorder (SAD), certain sleep problems, depression, jet lag, sleep disturbances in those with Parkinson's disease, the health consequences associated with shift work, and the resetting of the human circadian clock. Artificial lighting may change natural processes, interfere with melatonin production, or disrupt the circadian rhythm. Blue light may have a greater tendency than other colored light to affect living organisms through the disruption of their biological processes which can rely upon natural cycles of daylight and darkness. Exposure to blue light late in the evening and at night may be detrimental to one's health. Some blue or royal blue light within lower wavelengths can have hazardous effects to human eyes and skin, such as causing damage to the retina.

Significant challenges remain in providing LED lamps that can provide white light across a range of CCT values while simultaneously achieving high efficiencies, high luminous flux, good color rendering, and acceptable color stability. It is also a challenge to provide lighting apparatuses that can provide desirable lighting performance while allowing for the control of circadian energy performance.

DISCLOSURE

The present disclosure provides aspects of semiconductor light emitting devices comprising first, second, third, and fourth LED strings, with each LED string comprising one or more LEDs having an associated luminophoric medium, wherein the first, second, third, and fourth LED strings together with their associated luminophoric mediums can comprise red, blue, green, and cyan channels respectively, producing first, second, third, and fourth unsaturated color points within red, blue, green, and cyan regions on the 1931 CIE Chromaticity diagram, respectively. The devices can further include a control circuit can be configured to adjust a fifth color point of a fifth unsaturated light that results from a combination of the first, second, third, and fourth unsaturated light, with the fifth color point falls within a 7-step MacAdam ellipse around any point on the black body locus having a correlated color temperature between 1800K and 10000K. The devices can be configured to generate the fifth unsaturated light corresponding to a plurality of points along a predefined path with the light generated at each point having light with Rf greater than or equal to about 85, Rg greater than or equal to about 90 and less than or equal to about 110, or both. The devices can be configured to generate the fifth unsaturated light corresponding to a plurality of points along a predefined path with the light generated at each point having light with Ra greater than or equal to about 90 along points with correlated color temperature between about 1800K and 10000K, R9 greater than or equal to 70 along points with correlated color temperature between about 2000K and about 10000K, or both. The devices can be configured to generate the fifth unsaturated light corresponding to a plurality of points along a predefined path with the light generated at each point having light with R9 greater than or equal to 80 along greater than or equal to 90% of the points with correlated color temperature between about 2000K and about 10000K. The devices can be configured to generate the fifth unsaturated light corresponding to a plurality of points along a predefined path with the light generated at each point having one or more of EML greater than or equal to about 0.5 along points with correlated color temperature above about 2100K, EML greater than or equal to about 0.6 along points with correlated color temperature above about 2400K, EML greater than or equal to about 0.75 along points with correlated color temperature above about 3000K EML greater than or equal to about 1.0 along points with correlated color temperature above about 4000K, and EML greater than or equal to about 1.2 along points with correlated color temperature above about 6000K. The devices can be configured to generate the fifth unsaturated light corresponding to a plurality of points along a predefined path with the light generated at each point having light with R13 greater than or equal to about 94, R15 greater than or equal to about 88, or both. The blue color region can comprise a region on the 1931 CIE Chromaticity Diagram defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus. The red color region can comprise a region on the 1931 CIE Chromaticity Diagram defined by the spectral locus between the constant CCT line of 1600K and the line of purples, the line of purples, a line connecting the ccx, ccy color coordinates (0.61, 0.21) and (0.47, 0.28), and the constant CCT line of 1600K. The green color region can comprise a region on the 1931 CIE Chromaticity Diagram defined by the constant CCT line of 6700K, the Planckian locus, and the spectral locus. The green color region can comprise a region on the 1931 CIE Chromaticity Diagram defined by a 60-step MacAdam ellipse centered approximately 65 points above the Planckian locus at 4500K, the Planckian locus, and the constant CCT line of 6700K. The cyan color region can comprise a region on the 1931 CIE Chromaticity Diagram defined by a line connecting the Planckian locus, the constant CCT line of 3200K, the spectral locus, and the constant CCT line of 20000K. The cyan color region can comprise a region on the 1931 CIE Chromaticity Diagram defined by a 41-step MacAdam ellipse centered approximately 46 points above the Planckian locus at a CCT of 5600K, and the Planckian locus. The spectral power distributions for one or more of the red channel, blue channel, green channel, and cyan channel can fall within the minimum and maximum ranges shown in Tables 1 and 2. The red channel can have a spectral power distribution with spectral power in one or more of the wavelength ranges other than the reference wavelength range increased or decreased within 30% greater or less, within 20% greater or less, within 10% greater or less, or within 5% greater or less than the values of a red channel shown in Tables 3 and 4. The blue channel can have a spectral power distribution with spectral power in one or more of the wavelength ranges other than the reference wavelength range increased or decreased within 30% greater or less, within 20% greater or less, within 10% greater or less, or within 5% greater or less than the values of a blue channel shown in Tables 3 and 4. The green channel can have a spectral power distribution with spectral power in one or more of the wavelength ranges other than the reference wavelength range increased or decreased within 30% greater or less, within 20% greater or less, within 10% greater or less, or within 5% greater or less than the values of a green channel shown in Table 3. The cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a cyan channel shown in Table 3. One or more of the LEDs in the fourth LED string can have a peak wavelength of between about 480 nm and about 505 nm. One or more of the LEDs in the first, second, and third LED strings can have a peak wavelength of between about 430 nm and about 460 nm.

In some aspects, the present disclosure provides methods of generating white light, the methods comprising providing first, second, third, and fourth LED strings, with each LED string comprising one or more LEDs having an associated luminophoric medium, wherein the first, second, third, and fourth LED strings together with their associated luminophoric mediums comprise red, blue, green, and cyan channels respectively, producing first, second, third, and fourth unsaturated light with color points within red, blue, green, and cyan regions on the 1931 CIE Chromaticity diagram, respectively, the methods further comprising providing a control circuit configured to adjust a fifth color point of a fifth unsaturated light that results from a combination of the first, second, third, and fourth unsaturated light, with the fifth color point falls within a 7-step MacAdam ellipse around any point on the black body locus having a correlated color temperature between 1800K and 10000K, generating two or more of the first, second, third, and fourth unsaturated light, and combining the two or more generated unsaturated lights to create the fifth unsaturated light.

In some aspects, the present disclosure provides methods of generating white light with the semiconductor light emitting devices described herein. In some implementations, different operating modes can be used to generate the white light. In certain implementations, substantially the same white light points, with similar CCT values, can be generated in different operating modes that each utilize different combinations of the blue, red, green, and cyan channels of the disclosure. In some implementations, two operating modes can be used that comprise a first operating mode that uses the blue, red, and green channels and a second operating mode that uses the blue, red, and cyan channels of a device. In certain implementations, switching between the first operating mode and the second operating mode can increase the EML by about 5%, about 10%, about 15%, about 20%, about 25%, about 30%, about 35%, about 40%, about 45%, about 50%, about 55%, or about 60% while providing a Ra value within about 1, about 2, about 3, about 4, about 5, about 6, about 7, about 8, about 9, or about 10 while generating white light at substantially the same color point on the 1931 Chromaticity Diagram. In some implementations, the light generated with the first operating mode and the light generated in the second operating mode can be within about 1.0 standard deviations of color matching (SDCM). In some implementations, the light generated with the first operating mode and the light generated in the second operating mode can be within about 0.5 standard deviations of color matching (SDCM).

The general disclosure and the following further disclosure are exemplary and explanatory only and are not restrictive of the disclosure, as defined in the appended claims. Other aspects of the present disclosure will be apparent to those skilled in the art in view of the details as provided herein. In the figures, like reference numerals designate corresponding parts throughout the different views. All callouts and annotations are hereby incorporated by this reference as if fully set forth herein.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale. In the drawings:

FIGS. 7A-7F show tables of data of light rendering performance characteristics and metrics of an implementation of the present disclosure:

FIGS. 8A-8E show tables of data of light rendering performance characteristics and metrics of an implementation of the present disclosure;

FIGS. 9A-9E show tables of data of light rendering performance characteristics and metrics of an implementation of the present disclosure;

FIGS. 10A-10E show tables of data of light rendering performance characteristics and metrics of an implementation of the present disclosure:

FIGS. 11A-11E show tables of data of light rendering performance characteristics and metrics of an implementation of the present disclosure;

FIGS. 12A-12E show tables of data of light rendering performance characteristics and metrics of an implementation of the present disclosure;

FIGS. 13A-13E show tables of data of light rendering performance characteristics and metrics of an implementation of the present disclosure:

FIGS. 14A-14F show tables of data of light rendering performance characteristics and metrics of an implementation of the present disclosure; and FIGS. 15A-15E show tables of data of light rendering performance characteristics and metrics of an implementation of the present disclosure.

All descriptions and callouts in the Figures are hereby incorporated by this reference as if fully set forth herein.

FURTHER DISCLOSURE

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular exemplars by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another exemplar includes from the one particular value and/or to the other particular value. Similarly, when values are expressed as approximations, by use of the antecedent "about," it will be understood that the particular value forms another exemplar. All ranges are inclusive and combinable.

It is to be appreciated that certain features of the disclosure which are, for clarity, described herein in the context of separate exemplar, may also be provided in combination in a single exemplary implementation. Conversely, various features of the disclosure that are, for brevity, described in the context of a single exemplary implementation, may also be provided separately or in any subcombination. Further, reference to values stated in ranges include each and every value within that range.

Figure 1:
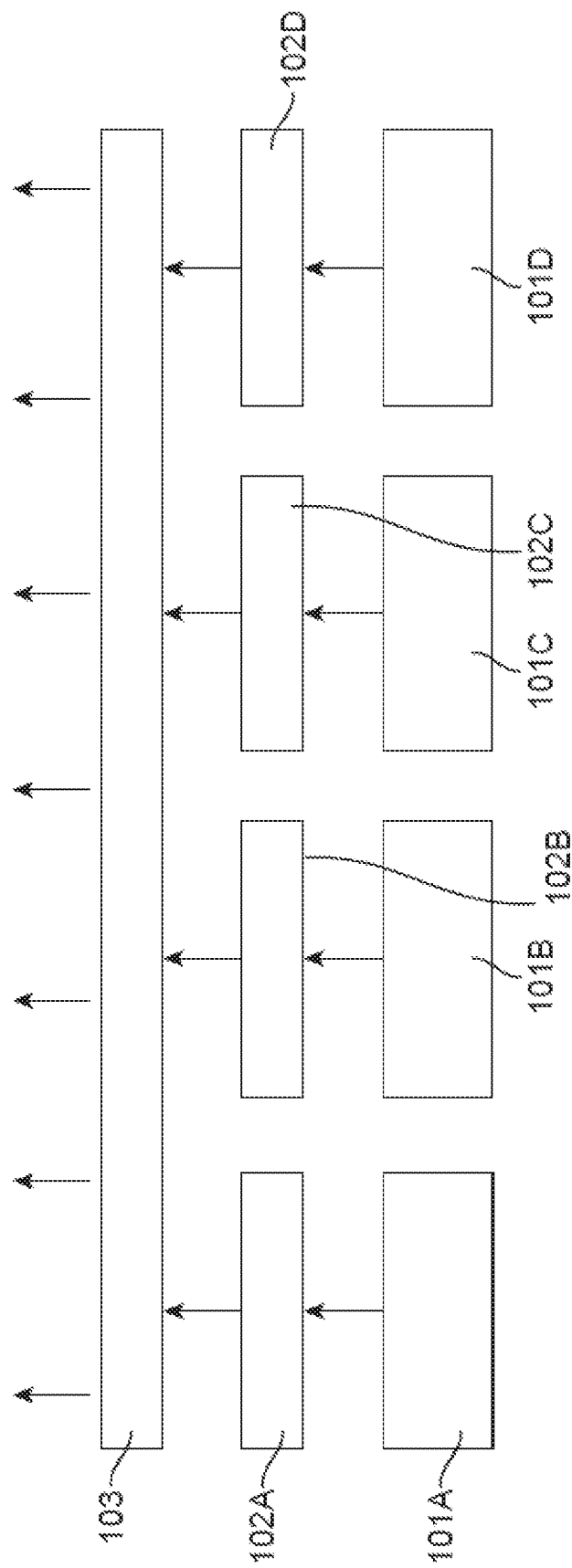
FIG. 1 illustrates aspects of light emitting devices according to the present disclosure.

In one aspect, the present disclosure provides semiconductor light emitting devices 100 that can have a plurality of light emitting diode (LED) strings. Each LED string can have one, or more than one, LED. As depicted schematically in FIG. 1, the device 100 may comprise one or more LED strings (101A/101B/101C/101D) that emit light (schematically shown with arrows). In some instances, the LED strings can have recipient luminophoric mediums (102A/102B/102C/102D) associated therewith. The light emitted from the LED strings, combined with light emitted from the recipient luminophoric mediums, can be passed through one or more optical elements 103. Optical elements 103 may be one or more diffusers, lenses, light guides, reflective elements, or combinations thereof. In some implementations, one or more of the LED strings 101A/101B/101C/101D may be provided without an associated luminophoric medium. In further implementations, three of the LED strings 101A/101B/101C can be provided with an associated luminophoric medium for each, and the fourth LED string 101D can be provided without an associated luminophoric medium.

A recipient luminophoric medium 102A, 102B, 102C, or 102D includes one or more luminescent materials and is positioned to receive light that is emitted by an LED or other semiconductor light emitting device. In some implementations, recipient luminophoric mediums include layers having luminescent materials that are coated or sprayed directly onto a semiconductor light emitting device or on surfaces of the packaging thereof, and clear encapsulants that include luminescent materials that are arranged to partially or fully cover a semiconductor light emitting device. A recipient luminophoric medium may include one medium layer or the like in which one or more luminescent materials are mixed, multiple stacked layers or mediums, each of which may include one or more of the same or different luminescent materials, and/or multiple spaced apart layers or mediums, each of which may include the same or different luminescent materials. Suitable encapsulants are known by those skilled in the art and have suitable optical, mechanical, chemical, and thermal characteristics. In some implementations, encapsulants can include dimethyl silicone, phenyl silicone, epoxies, acrylics, and polycarbonates. In some implementations, a recipient luminophoric medium can be spatially separated (i.e., remotely located) from an LED or surfaces of the packaging thereof. In some implementations, such spatial segregation may involve separation of a distance of at least about 1 mm, at least about 2 mm, at least about 5 mm, or at least about 10 mm. In certain embodiments, conductive thermal communication between a spatially segregated luminophoric medium and one or more electrically activated emitters is not substantial. Luminescent materials can include phosphors, scintillators, day glow tapes, nanophosphors, inks that glow in visible spectrum upon illumination with light, semiconductor quantum dots, or combinations thereof. In some implementations, the luminescent materials may comprise phosphors comprising one or more of the following materials: $BaMg_2Al_{16}O_{27}:Eu^{2+}$, $BaMg_2Al_{16}O_{27}Eu^{2+}$, $Mn^{2+}$, $CaSiO_3:Pb$, Mn, $CaWO_4:Pb$, $MgWO_4$, $Sr_5Cl(PO_4)_3:Eu^{2+}$, $Sr_2P_2O_7:Sn^{2+}$, $Sr_6P_5BO_{20}:Eu$, $Ca_5F(PO_4)_3:Sb$, $(Ba,Ti)_2P_2O_7:Ti$, $Sr_5F(PO_4)_3:Sb,Mn$, $(La,Ce,Tb)PO_4:Ce,Tb$, $(Ca,Zn,Mg)_3(PO_4)_2:Sn$, $(Sr,Mg)_3(PO_4)_2:Sn$, $Y_2O_3:Eu^{3+}$, $Mg_4(F)GeO_6:Mn$, $LaMgAl_{11}O_{19}:Ce$, $LaPO_4:Ce$, $SrAl_{12}O_{19}:Ce$, $BaSi_2O_5:Pb$, $SrB_4O_7:Eu$, $Sr_2MgSi_2O_7:Pb$, $Gd_2O_2S:Tb$, $Gd_2O_2S:Eu$, $Gd_2O_2S:Pr$, $Gd_2O_2S:Pr,Ce,F$, $Y_2O_2S:Tb$, $Y_2O_2S:Eu$, $Y_2O_2S:Pr$, $Zn(0.5)Cd(0.4)S:Ag$, $Zn(0.4)Cd(0.6)S:Ag$, $Y_2SiO_5:Ce$, $YAlO_3:Ce$, $Y_3(Al,Ga)_5O_{12}:Ce$, $CdS:In$, $ZnO:Ga$, $ZnO:Zn$, $(Zn,Cd)S:Cu,Al$, $ZnCdS:Ag,Cu$, $ZnS:Ag$, $ZnS:Cu$, $NaI:Tl$, $CsI:Tl$, $^6LiF/ZnS:Ag$, $^6LiF/ZnS:Cu,Al,Au$, $ZnS:Cu,Al$, $ZnS:Cu,Au,Al$, $CaAlSiN_3:Eu$, $(Sr,Ca)AlSiN_3:Eu$, $(Ba,Ca,Sr,Mg)_2SiO_4:Eu$, $Lu_3Al_5O_{12}:Ce$, $Eu^{3+}(Gd_{0.9}Y_{0.1})_3Al_5O_{12}:Bi^{3+}$, $Tb^{3+}$, $Y_3Al_5O_{12}:Ce$, $(La,Y)_3Si_6N_{11}:Ce$, $Ca_2AlSi_3O_2N_5:Ce^{3+}$, $Ca_2AlSi_3O_2N_5:Eu^{2+}$, $BaMgAl_{10}O_{17}:Eu$, $Sr_5(PO_4)_3Cl:Eu$, $(Ba,Ca,Sr,Mg)_2SiO_4:Eu$, $Si_{6-z}Al_zN_{8-z}O_z:Eu$ (wherein $0\le z\le 4.2$); $M_3Si_6O_{12}N_2:Eu$ (wherein M=alkaline earth metal element), $(Mg,Ca,Sr,Ba)Si_2O_2N_2:Eu$, $Sr_4Al_{14}O_{25}:Eu$, $(Ba,Sr,Ca)Al_2O_4:Eu$, $(Sr,Ba)Al_2Si_2O_8:Eu$, $(Ba,Mg)_2SiO_4:Eu$, $(Ba,Sr,Ca)_2(Mg, Zn)Si_2O_7:Eu$, $(Ba,Ca,Sr,Mg)_9(Sc,Y,Lu,Gd)_2(Si,Ge)_6O_{24}:Eu$, $Y_2SiO_5:CeTb$, $Sr_2P_2O_7—Sr_2B_2O_5:Eu$, $Sr_2Si_3O_8\cdot 2SrCl_2:Eu$, $Zn_2SiO_4:Mn$, $CeMgAl_{11}O_{19}:Tb$, $Y_3Al_5O_{12}:Tb$, $Ca_2Y_8(SiO_4)_6O_2:Th$. $La_3Ga_5SiO_{14}:Tb$, $(Sr,Ba,Ca)Ga_2S_4:Eu,Tb,Sm$, $Y_3(Al,Ga)_5O_{12}:Ce$, $(Y,Ga,Tb,La,Sm,Pr,Lu)_3(Al,Ga)_5O_{12}:Ce$, $Ca_3Sc_2Si_3O_{12}:Ce$, $Ca_3(Sc,Mg,Na,Li)_2Si_3O_{12}:Ce$, $CaSc_2O_4:Ce$, Eu-activated β-Sialon, $SrAl_2O_4:Eu$, $(La,Gd,Y)_2O_2S:Tb$, $CeLaPO_4:Tb$, $ZnS:Cu,Al$, $ZnS:Cu,Au,Al$, $(Y,Ga,Lu,Sc,La)BO_3:Ce,Tb$, $Na_2Gd_2B_2O_7:Ce,Tb$, $(Ba,Sr)_2(Ca,Mg,Zn)B_2O_6:K,Ce,Tb$, $Ca_8Mg(SiO_4)_4Cl_2:Eu,Mn$, $(Sr,Ca,Ba)(Al,Ga,In)_2S_4:Eu$, $(Ca,Sr)_8(Mg,Zn)(SiO_4)_4Cl_2:Eu,Mn$, $M_3Si_6O_9N_4:Eu$, $Sr_5Al_5Si_{21}O_2N_{35}:Eu$, $Sr_3Si_{13}Al_3N_{21}O_2:Eu$, $(Mg,Ca,Sr,Ba)_2Si_5N_8:Eu$, $(La,Y)_2O_2S:Eu$, $(Y,La,Gd,Lu)_2O_2S:Eu$, $Y(V,P)O_4:Eu$, $(Ba,Mg)_2SiO_4:Eu,Mn$, $(Ba,Sr, Ca,Mg)_2SiO_4:Eu,Mn$, $LiW_2O_8:Eu$, $LiW_2O_8:Eu,Sm$, $Eu_2W_2O_9$, $Eu_2W_2O_9:Nb$ and $Eu_2W_2O_9:Sm$, $(Ca,Sr)S:Eu$, $YAlO_3:Eu$, $Ca_2Y_8(SiO_4)_6O_2:Eu$, $LiY_9(SiO_4)_6O_2:Eu$, $(Y,Gd)_3Al_5O_{12}:Ce$, $(Tb,Gd)_3Al_5O_{12}:Ce$, $(Mg,Ca,Sr,Ba)_2Si_5(N,O)_8:Eu$, $(Mg,Ca,Sr,Ba)Si(N,O)_2:Eu$, $(Mg,Ca,Sr,Ba)AlSi(N,O)_3:Eu$, $(Sr,Ca,Ba,Mg)_{10}(PO_4)_6Cl_2:Eu$, Mn, $Eu,Ba_3MgSi_2O_8:Eu,Mn$, $(Ba,Sr,Ca,Mg)_3(Zn,Mg)Si_2O_8:Eu,Mn$, $(k-x)MgO\cdot xAF_2\cdot GeO_2:yMn^{4+}$ (wherein k=2.8 to 5, x=0.1 to 0.7, y=0.005 to 0.015, A=Ca, Sr, Ba, Zn or a mixture thereof), Eu-activated α-Sialon, $(Gd,Y,Lu,La)_2O_3:Eu,Bi$, $(Gd,Y,Lu,La)_2O_2S:Eu,Bi$, $(Gd,Y,Lu,La)VO_4:Eu,Bi$, $SrY_2S_4:Eu,Ce$, $CaLa_2S_4:Ce,Eu$, $(Ba,Sr,Ca)MgP_2O_7:Eu,Mn$, $(Sr,Ca,Ba,Mg,Zn)_2P_2O_7:Eu,Mn$, $(Y,Lu)_2WO_6:Eu,Ma$, $(Ba,Sr,Ca)_xSi_yN_z:Eu,Ce$ (wherein x, y and z are integers equal to or greater than 1), $(Ca,Sr,Ba,Mg)_{10}(PO_4)_6(F,Cl,Br,OH):Eu,Mn$, $((Y,Lu,Gd,Tb)_{1-x-y}Sc_xCe_y)_2(Ca,Mg)(Mg,Zn)_{2+r}Si_{z-q}Ge_qO_{12+\delta}$, $SrAlSi_4N_7$, $Sr_2Al_2Si_9O_2N_{14}:Eu$, $M^1_aM^1_bM^3_cO_d$ (wherein $M^1$=activator element including at least Ce, $M^2$=bivalent metal element, $M^3$=trivalent metal element, $0.0001\le a\le 0.2$, $0.8\le b\le 1.2$, $1.6\le c\le 2.4$ and $3.2\le d\le 4.8$), $A_{2+x}M_yMn_zF_n$ (wherein A=Na and/or K; M=Si and Al, and $-1\le x\le 1$, $0.9\le y+z\le 1.1$, $0.001\le z\le 0.4$ and $5\le n\le 7$), KSF/KSNAF, or $(La_{1-x-y}, Eu_x, Ln_y)_2O_2S$ (wherein $0.02\le x\le 0.50$ and $0\le y\le 0.50$, $Ln=Y^{3+}$, $Gd^{3+}$, $Lu^{3+}$, $Sc^{3+}$, $Sm^{3+}$ or $Er^{3+}$). In some preferred implementations, the luminescent materials may comprise phosphors comprising one or more of the following materials: $CaAlSiN_3:Eu$, $(Sr,Ca)AlSiN_3:Eu$, $BaMgAl_{10}O_{17}:Eu$, $(Ba,Ca,Sr,Mg)_2SiO_4:Eu$, β-SiAlON, $Lu_3Al_5O_{12}:Ce$, $Eu^{3+}(Cd_{0.9}Y_{0.1})_3Al_5O_{12}:Bi^{3+},Tb^{3+}$, $Y_3Al_5O_{12}:Ce$, $La_3Si_6N_{11}:Ce$, $(La,Y)_3Si_6N_{11}:Ce$, $Ca_2AlSi_3O_2N_5:Ce^{3+}$, $Ca_2AlSi_3O_2N_5:Ce^{3+},Eu^{2+}$, $Ca_2AlSi_3O_2N_5$:$Eu^{2+}$, $BaMgAl_{10}O_{17}$:$Eu^{2+}$, $Sr_{4.5}Eu_{0.5}(PO_4)_3Cl$, or $M^1{}_aM^2{}_cM^3{}_cO_d$ (wherein $M^1$=activator element comprising Ce, $M^2$=bivalent metal element, $M^3$=trivalent metal element, $0.001 \leq a \leq 0.2$, $0.8 \leq b \leq 1.2$, $1.6 \leq c \leq 2.4$ and $3.2 \leq d \leq 4.8$). In further preferred implementations, the luminescent materials may comprise phosphors comprising one or more of the following materials: $CaAlSiN_3$:Eu, $BaMgAl_{10}O_{17}$:Eu, $Lu_3Al_5O_{12}$:Ce, or $Y_3Al_5O_{12}$:Ce.

Figure 2:
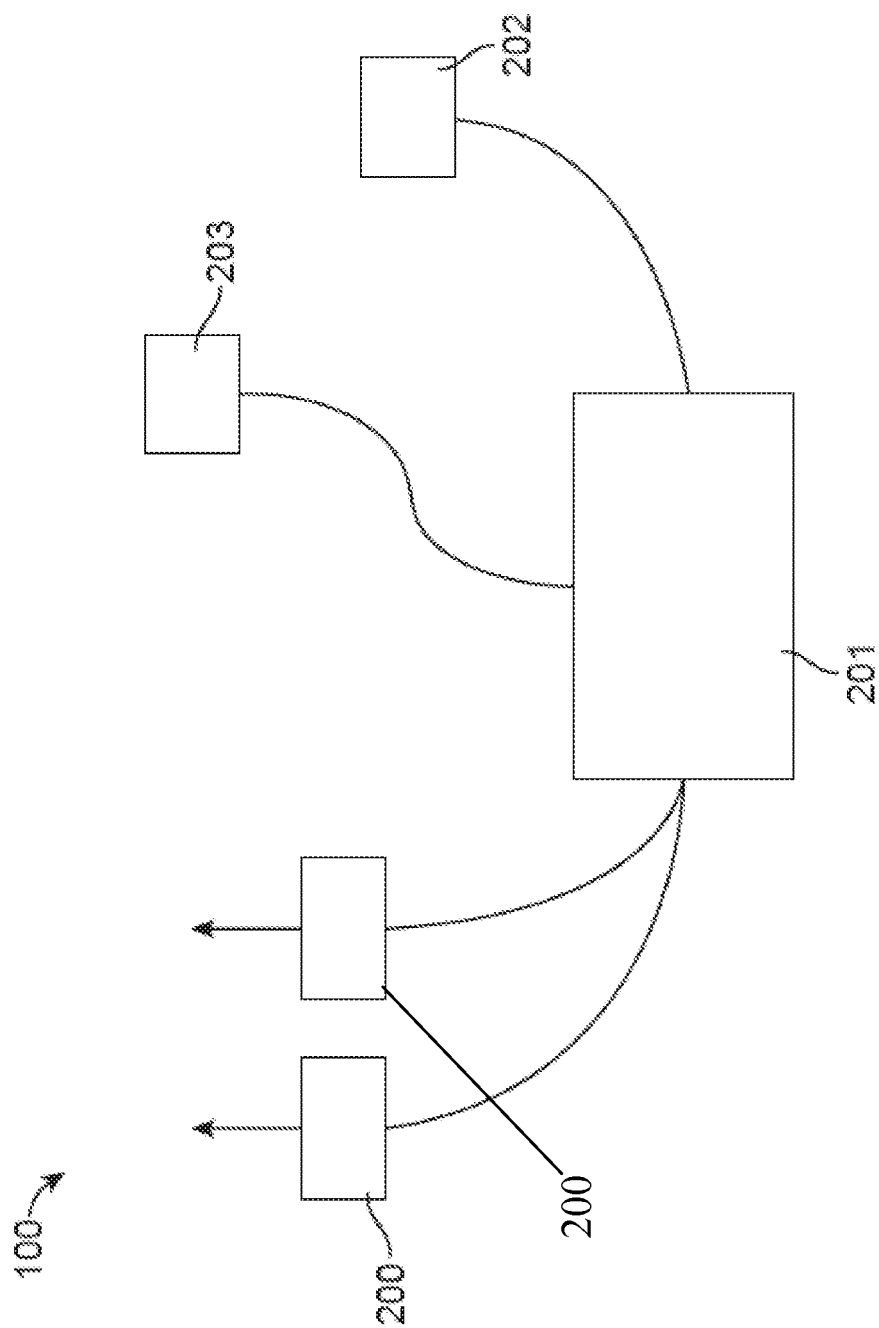
FIG. 2 illustrates aspects of light emitting devices according to the present disclosure.

Some implementations of the present invention relate to use of solid state emitter packages. A solid state emitter package typically includes at least one solid state emitter chip that is enclosed with packaging elements to provide environmental and/or mechanical protection, color selection, and light focusing, as well as electrical leads, contacts or traces enabling electrical connection to an external circuit. Encapsulant material, optionally including luminophoric material, may be disposed over solid state emitters in a solid state emitter package. Multiple solid state emitters may be provided in a single package. A package including multiple solid state emitters may include at least one of the following: a single leadframe arranged to conduct power to the solid state emitters, a single reflector arranged to reflect at least a portion of light emanating from each solid state emitter, a single submount supporting each solid state emitter, and a single lens arranged to transmit at least a portion of light emanating from each solid state emitter. Individual LEDs or groups of LEDs in a solid state package (e.g., wired in series) may be separately controlled. As depicted schematically in FIG. 2, multiple solid state packages 200 may be arranged in a single semiconductor light emitting device 100. Individual solid state emitter packages or groups of solid state emitter packages (e.g., wired in series) may be separately controlled. Separate control of individual emitters, groups of emitters, individual packages, or groups of packages, may be provided by independently applying drive currents to the relevant components with control elements known to those skilled in the art. In one embodiment, at least one control circuit 201a may include a current supply circuit configured to independently apply an on-state drive current to each individual solid state emitter, group of solid state emitters, individual solid state emitter package, or group of solid state emitter packages. Such control may be responsive to a control signal (optionally including at least one sensor 202 arranged to sense electrical, optical, and/or thermal properties and/or environmental conditions), and a control system 203 may be configured to selectively provide one or more control signals to the at least one current supply circuit. In various embodiments, current to different circuits or circuit portions may be pre-set, user-defined, or responsive to one or more inputs or other control parameters. The design and fabrication of semiconductor light emitting devices are well known to those skilled in the art, and hence further description thereof will be omitted.

Figure 3:
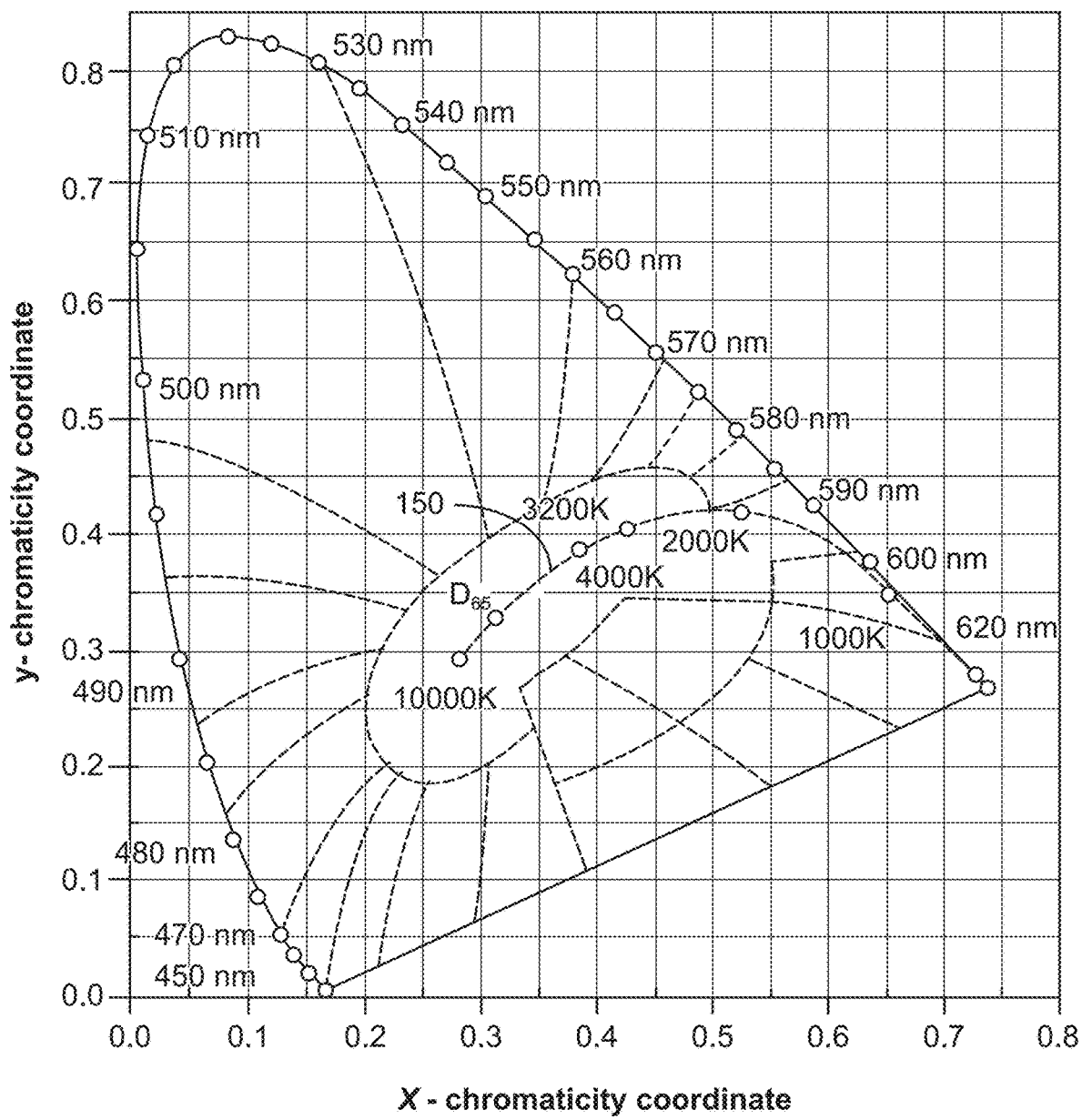
FIG. 3 depicts a graph of a 1931 CIE Chromaticity Diagram illustrating the location of the Planckian locus.
Figures 4A, 4B:
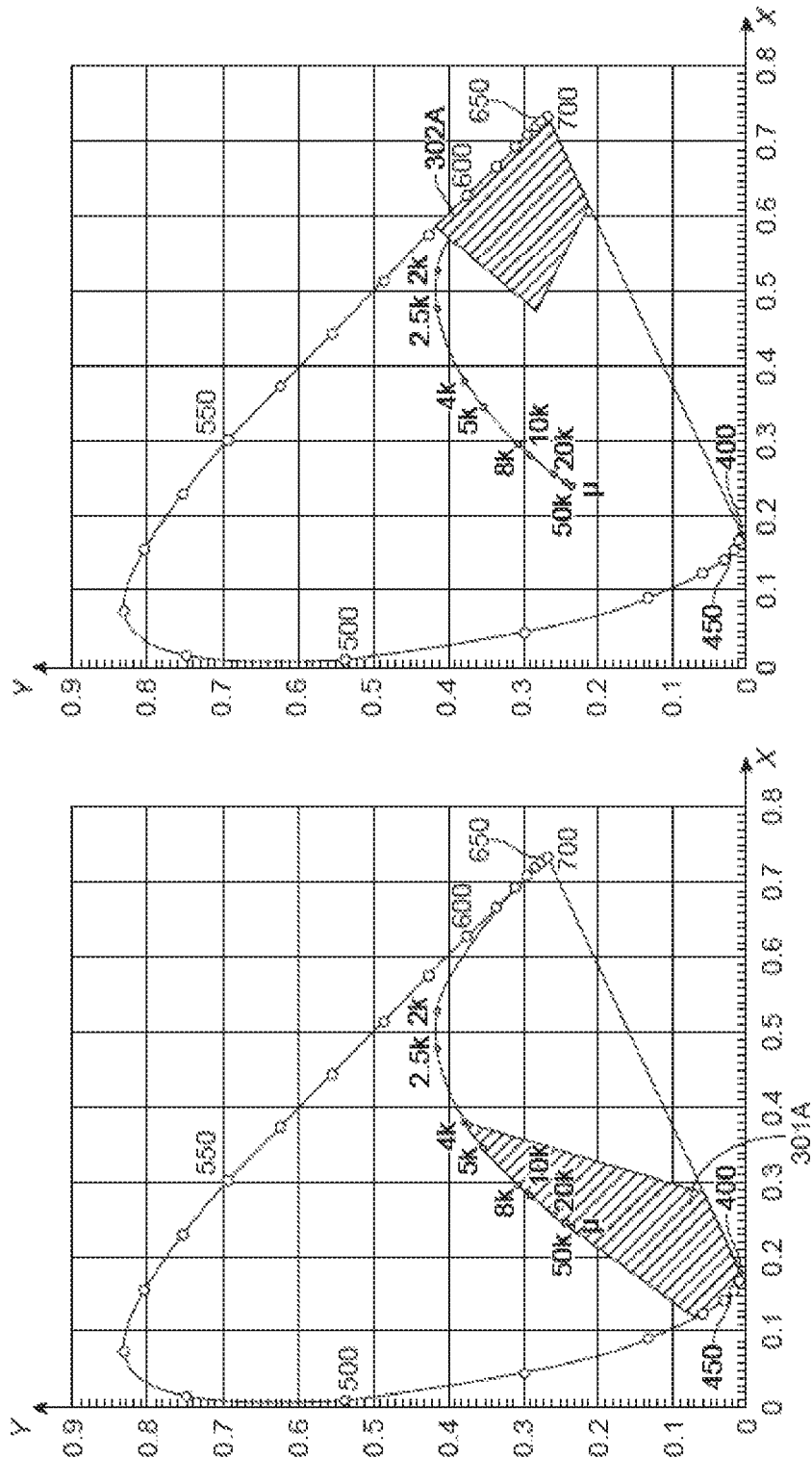
FIGS. 4A-4F illustrate some aspects of light emitting devices according to the present disclosure, including some suitable color ranges for light generated by components of the devices.
Figure 4C:
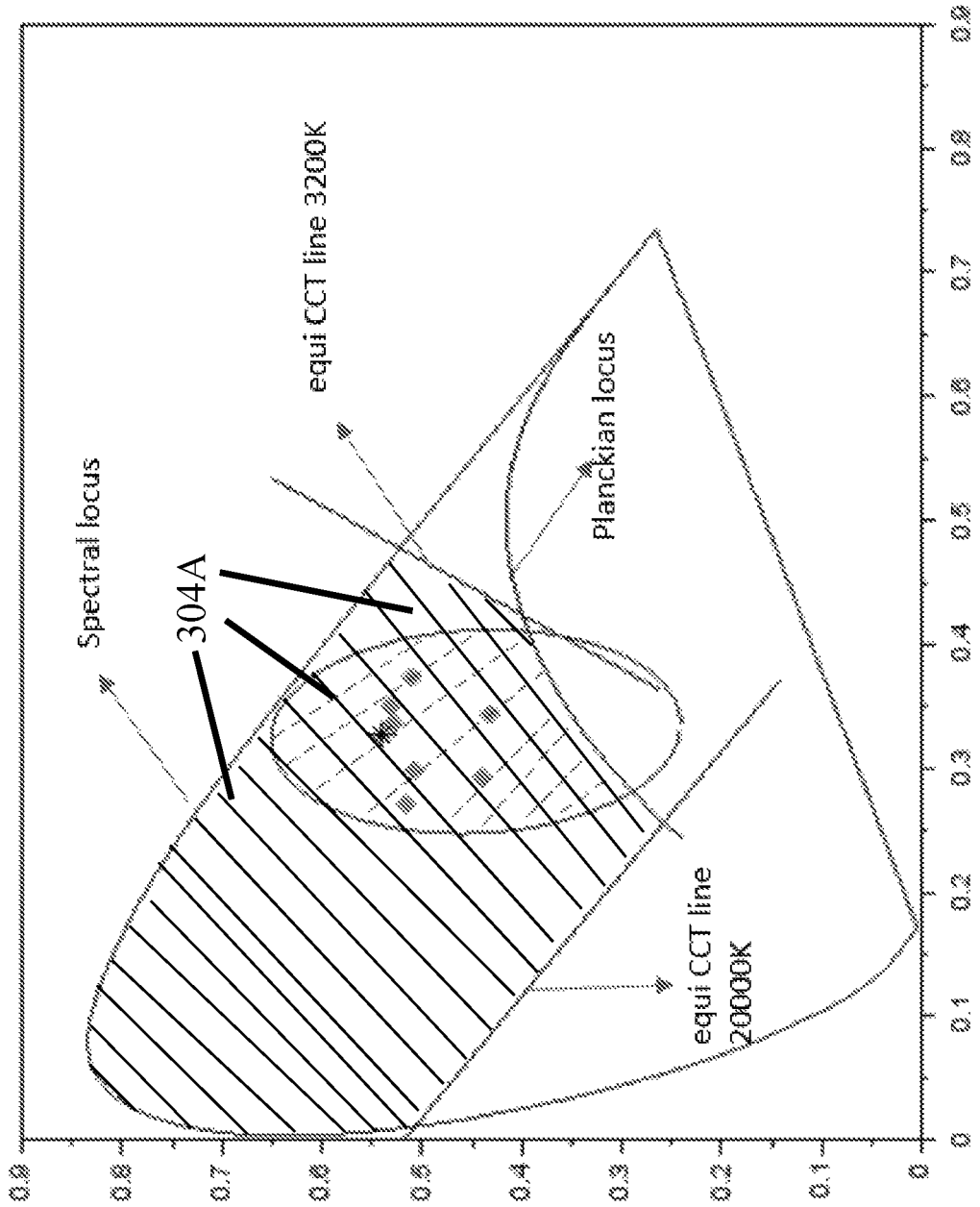
Figure 4D:
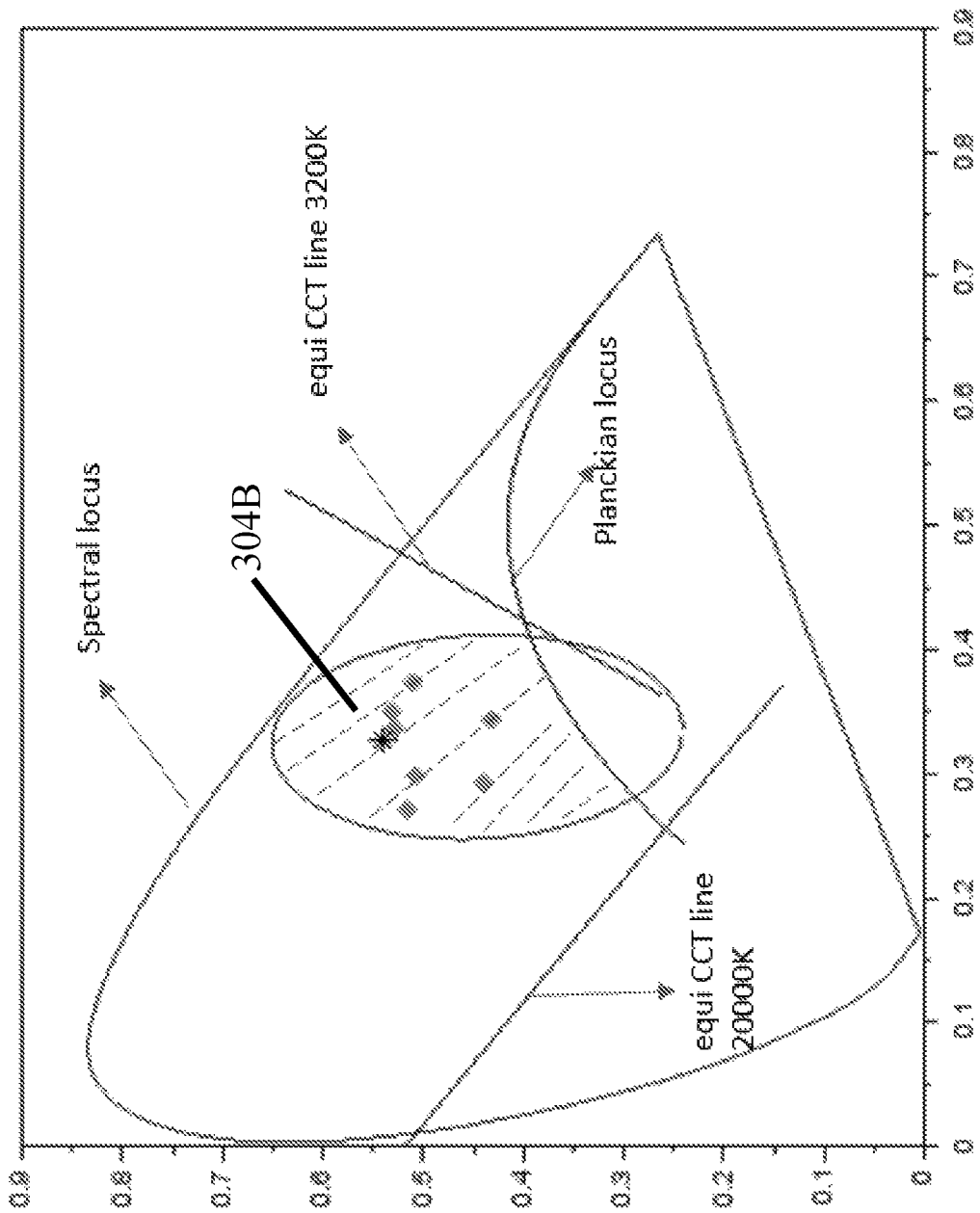
Figure 4E:
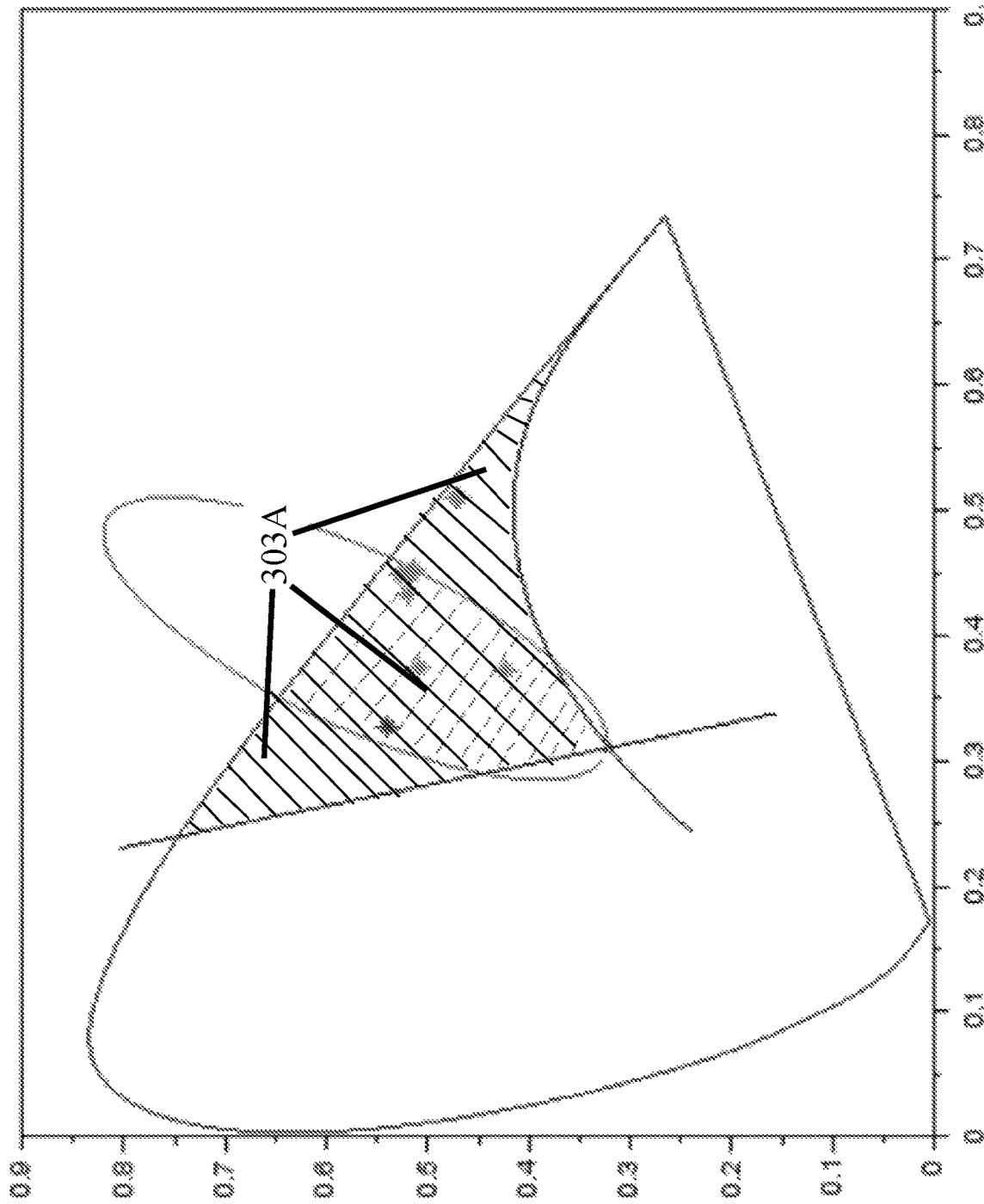
Figure 4F:
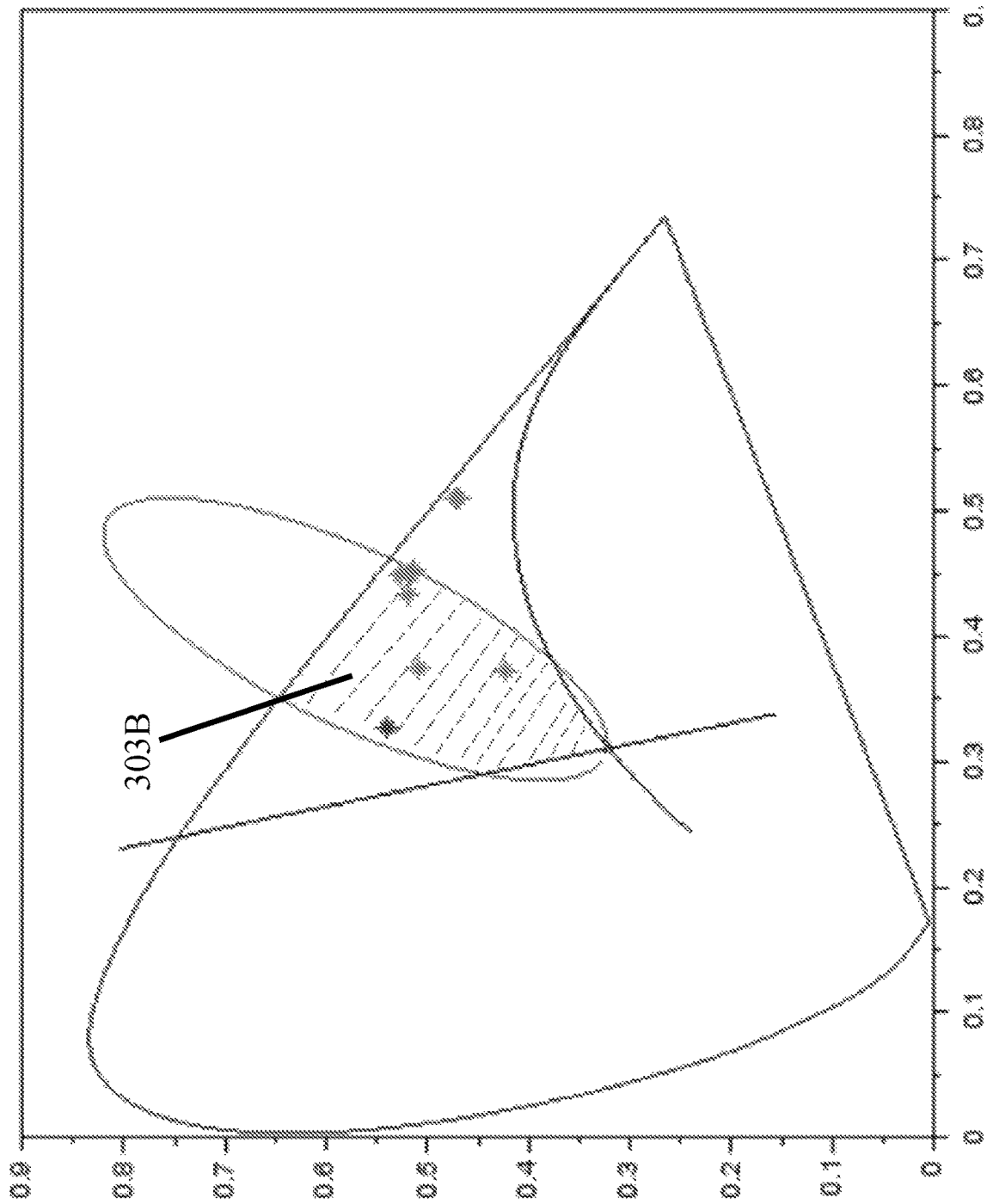

FIG. 3 illustrates a 1931 International Commission on Illumination (CIE) chromaticity diagram. The 1931 CIE Chromaticity diagram is a two-dimensional chromaticity space in which every visible color is represented by a point having x- and y-coordinates. Fully saturated (monochromatic) colors appear on the outer edge of the diagram, while less saturated colors (which represent a combination of wavelengths) appear on the interior of the diagram. The term "saturated", as used herein, means having a purity of at least 85%, the term "purity" having a well-known meaning to persons skilled in the art, and procedures for calculating purity being well-known to those of skill in the art. The Planckian locus, or black body locus (BBL), represented by line 150 on the diagram, follows the color an incandescent black body would take in the chromaticity space as the temperature of the black body changes from about 1000K to 10,000 K. The black body locus goes from deep red at low temperatures (about 1000 K) through orange, yellowish white, white, and finally bluish white at very high temperatures. The temperature of a black body radiator corresponding to a particular color in a chromaticity space is referred to as the "correlated color temperature." In general, light corresponding to a correlated color temperature (CCT) of about 2700 K to about 6500 K is considered to be "white" light. In particular, as used herein, "white light" generally refers to light having a chromaticity point that is within a 10-step MacAdam ellipse of a point on the black body locus having a CCT between 2700K and 6500K. However, it will be understood that tighter or looser definitions of white light can be used if desired. For example, white light can refer to light having a chromaticity point that is within a seven step MacAdam ellipse of a point on the black body locus having a CCT between 2700K and 6500K. The distance from the black body locus can be measured in the CIE 1960 chromaticity diagram, and is indicated by the symbol Δuv, or DUV. If the chromaticity point is above the Planckian locus the DUV is denoted by a positive number; if the chromaticity point is below the locus, DUV is indicated with a negative number. If the DUV is sufficiently positive, the light source may appear greenish or yellowish at the same CCT. If the DUV is sufficiently negative, the light source can appear to be purple or pinkish at the same CCT. Observers may prefer light above or below the Planckian locus for particular CCT values. DUV calculation methods are well known by those of ordinary skill in the art and are more fully described in ANSI C78.377, American National Standard for Electric Lamps—Specifications for the Chromaticity of Solid State Lighting (SSL) Products, which is incorporated by reference herein in its entirety for all purposes. A point representing the CIE Standard Illuminant D65 is also shown on the diagram. The D65 illuminant is intended to represent average daylight and has a CCT of approximately 6500K and the spectral power distribution is described more fully in Joint ISO/CIE Standard, ISO 10526:1999/CIE 5005/E-1998, CIE Standard Illuminants for Colorimetry, which is incorporated by reference herein in its entirety for all purposes.

The light emitted by a light source may be represented by a point on a chromaticity diagram, such as the 1931 CIE chromaticity diagram, having color coordinates denoted (ccx, ccy) on the X-Y axes of the diagram. A region on a chromaticity diagram may represent light sources having similar chromaticity coordinates.

The ability of a light source to accurately reproduce color in illuminated objects can be characterized using the color rendering index ("CRI"), also referred to as the CIE Ra value. The Ra value of a light source is a modified average of the relative measurements of how the color rendition of an illumination system compares to that of a reference black-body radiator or daylight spectrum when illuminating eight reference colors R1-R8. Thus, the Ra value is a relative measure of the shift in surface color of an object when lit by a particular lamp. The Ra value equals 100 if the color coordinates of a set of test colors being illuminated by the illumination system are the same as the coordinates of the same test colors being irradiated by a reference light source of equivalent CCT. For CCTs less than 5000K, the reference illuminants used in the CRI calculation procedure are the SPDs of blackbody radiators: for CCTs above 5000K, imaginary SPDs calculated from a mathematical model of daylight are used. These reference sources were selected to approximate incandescent lamps and daylight, respectively.

Daylight generally has an Ra value of nearly 100, incandescent bulbs have an Ra value of about 95, fluorescent lighting typically has an Ra value of about 70 to 85, while monochromatic light sources have an Ra value of essentially zero. Light sources for general illumination applications with an Ra value of less than 50 are generally considered very poor and are typically only used in applications where economic issues preclude other alternatives. The calculation of CIE Ra values is described more fully in Commission Internationale de l'Éclairage, 1995. *Technical Report: Method of Measuring and Specifying Colour Rendering Properties of Light Sources.* CIE No. 13.3-1995. Vienna, Austria: Commission Internationale de l'Éclairage, which is incorporated by reference herein in its entirety for all purposes. In addition to the Ra value, a light source can also be evaluated based on a measure of its ability to render seven additional colors R9-R15, which include realistic colors like red, yellow, green, blue, caucasian skin color (R13), tree leaf green, and asian skin color (R15), respectively. The ability to render the saturated red reference color R9 can be expressed with the R9 color rendering value ("R9 value"). Light sources can further be evaluated by calculating the gamut area index ("GAI"). Connecting the rendered color points from the determination of the CIE Ra value in two dimensional space will form a gamut area. Gamut area index is calculated by dividing the gamut area formed by the light source with the gamut area formed by a reference source using the same set of colors that are used for CRI. GAI uses an Equal Energy Spectrum as the reference source rather than a black body radiator. A gamut area index related to a black body radiator ("GAIBB") can be calculated by using the gamut area formed by the blackbody radiator at the equivalent CCT to the light source.

The ability of a light source to accurately reproduce color in illuminated objects can be characterized using the metrics described in *IES Method for Evaluating Light Source Color Rendition*, Illuminating Engineering Society. Product ID: TM-30-15 (referred to herein as the "TM-30-15 standard"), which is incorporated by reference herein in its entirety for all purposes. The TM-30-15 standard describes metrics including the Fidelity Index (Rf) and the Gamut Index (Rg) that can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. Rg values provide a measure of the color gamut that the light source provides relative to a reference illuminant. The range of Rg depends upon the Rf value of the light source being tested. The reference illuminant is selected depending on the CCT. For CCT values less than or equal to 4500K, Planckian radiation is used. For CCT values greater than or equal to 5500K, CIE Daylight illuminant is used. Between 4500K and 5500K a proportional mix of Planckian radiation and the CIE Daylight illuminant is used, according to the following equation:

$$S_{r,M}(\lambda,T_t) = \frac{5500-T_t}{1000}S_{r,P}(\lambda,T_t) + \left(1 - \frac{5500-T_t}{1000}\right)S_{r,D}(\lambda,T_t),$$

where $T_t$ is the CCT value, $S_{r,M}(\lambda, T_t)$ is the proportional mix reference illuminant, $S_{r,P}(\lambda, T_t)$ is Planckian radiation, and $S_{r,D}(\lambda, T_t)$ is the CIE Daylight illuminant.

Circadian illuminance (CLA) is a measure of circadian effective light, spectral irradiance distribution of the light incident at the cornea weighted to reflect the spectral sensitivity of the human circadian system as measured by acute melatonin suppression after a one-hour exposure, and CS, which is the effectiveness of the spectrally weighted irradiance at the cornea from threshold (CS=0.1) to saturation (CS=0.7). The values of CLA are scaled such that an incandescent source at 2856K (known as CIE Illuminant A) which produces 1000 lux (visual lux) will produce 1000 units of circadian lux (CLA). CS values are transformed CLA values and correspond to relative melotonian suppression after one hour of light exposure for a 2.3 mm diameter pupil during the mid-point of melotonian production. CS is calculated from $$CS = |0.7\left(1 - \frac{1}{1 + \left(\frac{CLA}{355.7}\right)^{1.126}}\right).$$

The calculation of CLA is more fully described in Rea et al., "Modelling the spectral sensitivity of the human circadian system," Lighting Research and Technology, 2011; 0: 1-12, and Figueiro et al., "Designing with Circadian Stimulus", October 2016, LD+A Magazine, Illuminating Engineering Society of North America, which are incorporated by reference herein in its entirety for all purposes. Figueiro et al. describe that exposure to a CS of 0.3 or greater at the eye, for at least one hour in the early part of the day, is effective for stimulating the circadian system and is associated with better sleep and improved behavior and mood.

Equivalent Melanopic Lux (EML) provides a measure of photoreceptive input to circadian and neurophysiological light responses in humans, as described in Lucas et al., "Measuring and using light in the melanopsin age." Trends in Neurosciences, January 2014, Vol. 37, No. 1, pages 1-9, which is incorporated by reference herein in its entirety, including all appendices, for all purposes. Melanopic lux is weighted to a photopigment with λmax 480 nm with pre-receptoral filtering based on a 32 year old standard observer, as described more fully in the Appendix A, Supplementary Data to Lucas et al. (2014), User Guide: Irradiance Toolbox (Oxford 18 Oct. 2013), University of Manchester, Lucas Group, which is incorporated by reference herein in its entirety for all purposes.

Blue Light Hazard (BLH) provides a measure of potential for a photochemical induced retinal injury that results from radiation exposure. Blue Light Hazard is described in IEC/EN 62471, Photobiological Safety of Lamps and Lamp Systems and Technical Report IEC/TR 62778: Application of TEC 62471 for the assessment of blue light hazard to light sources and luminaires, which are incorporated by reference herein in their entirety for all purposes. A BLH factor can be expressed in (weighted power/lux) in units of $\mu W/cm^2/lux$.

In some aspects the present disclosure relates to lighting devices and methods to provide light having particular vision energy and circadian energy performance. Many figures of merit are known in the art, some of which are described in Ji Hye Oh, Su Ji Yang and Young Rag Do, "Healthy, natural, efficient and tunable lighting: four-package white LEDs for optimizing the circadian effect, color quality and vision performance," Light: Science & Applications (2014) 3: e141-e149, which is incorporated herein in its entirety, including supplementary information, for all purposes. Luminous efficacy of radiation ("LER") can be calculated from the ratio of the luminous flux to the radiant flux (S(λ)). i.e. the spectral power distribution of the light source being evaluated, with the following equation:

$$LER\left(\frac{lm}{W}\right) = 683\left(\frac{lm}{W}\right)\frac{\int V(\lambda)S(\lambda)d\lambda}{\int S(\lambda)d\lambda}.$$

Circadian efficacy of radiation ("CER") can be calculated from the ratio of circadian luminous flux to the radiant flux, with the following equation:

$$CER\left(\frac{blm}{W}\right) = 683\left(\frac{blm}{W}\right)\frac{\int C(\lambda)S(\lambda)d\lambda}{\int S(\lambda)d\lambda}.$$

Circadian action factor ("CAF") can be defined by the ratio of CER to LER, with the following equation:

$$\left(\frac{blm}{lm}\right) = \frac{CER\left(\frac{blm}{W}\right)}{LER\left(\frac{lm}{W}\right)}.$$

The term "blm" refers to biolumens, units for measuring circadian flux, also known as circadian lumens. The term "lm" refers to visual lumens. V(λ) is the photopic spectral luminous efficiency function and C(λ) is the circadian spectral sensitivity function. The calculations herein use the circadian spectral sensitivity function, C(λ), from Gall et al., Proceedings of the CIE Symposium 2004 on Light and Health: Non-Visual Effects, 30 September-2 Oct. 2004; Vienna, Austria 2004. CIE: Wien, 2004, pp 129-132, which is incorporated herein in its entirety for all purposes. By integrating the amount of light (milliwatts) within the circadian spectral sensitivity function and dividing such value by the number of photopic lumens, a relative measure of melatonin suppression effects of a particular light source can be obtained. A scaled relative measure denoted as melatonin suppressing milliwatts per hundred lumens may be obtained by dividing the photopic lumens by 100. The term "melatonin suppressing milliwatts per hundred lumens" consistent with the foregoing calculation method is used throughout this application and the accompanying figures and tables.

The ability of a light source to provide illumination that allows for the clinical observation of cyanosis is based upon the light source's spectral power density in the red portion of the visible spectrum, particularly around 660 nm. The cyanosis observation index ("COI") is defined by AS/NZS 1680.2.5 Interior Lighting Part 2.5: Hospital and Medical Tasks, Standards Australia, 1997 which is incorporated by reference herein in its entirety, including all appendices, for all purposes. COI is applicable for CCTs from about 3300K to about 5500K, and is preferably of a value less than about 3.3. If a light source's output around 660 nm is too low a patient's skin color may appear darker and may be falsely diagnosed as cyanosed. If a light source's output at 660 nm is too high, it may mask any cyanosis, and it may not be diagnosed when it is present. COI is a dimensionless number and is calculated from the spectral power distribution of the light source. The COI value is calculated by calculating the color difference between blood viewed under the test light source and viewed under the reference lamp (a 4000 K Planckian source) for 50% and 100% oxygen saturation and averaging the results. The lower the value of COI, the smaller the shift in color appearance results under illumination by the source under consideration.

The ability of a light source to accurately reproduce color in illuminated objects can be characterized by the Television Lighting Consistency Index ("TLCI-2012" or "TLCI") value Qa, as described fully in EBU Tech 3355, Method for the Assessment of the Colorimetric Properties of Luminaires, European Broadcasting Union ("EBU"), Geneva, Switzerland (2014), and EBU Tech 3355-s1, An Introduction to Spectroradiometry, which are incorporated by reference herein in their entirety, including all appendices, for all purposes. The TLCI compares the test light source to a reference luminaire, which is specified to be one whose chromaticity falls on either the Planckian or Daylight locus and having a color temperature which is that of the CCT of the test light source. If the CCT is less than 3400 K, then a Planckian radiator is assumed. If the CCT is greater than 5000 K, then a Daylight radiator is assumed. If the CCT lies between 3400 K and 5000 K, then a mixed illuminant is assumed, being a linear interpolation between Planckian at 3400 K and Daylight at 5000 K. Therefore, it is necessary to calculate spectral power distributions for both Planckian and Daylight radiators. The mathematics for both operations is known in the art and is described more fully in CIE Technical Report 15:2004, Colorimetry $3^{rd}$ ed., International Commission on Illumination (2004), which is incorporated herein in its entirety for all purposes.

In some exemplary implementations, the present disclosure provides semiconductor light emitting devices 100 that include a plurality of LED strings, with each LED string having a recipient luminophoric medium that comprises a luminescent material. The LED(s) in each string and the luminophoric medium in each string together emit an unsaturated light having a color point within a color range in the 1931 CIE chromaticity diagram. A "color range" in the 1931 CIE chromaticity diagram refers to a bounded area defining a group of color coordinates (ccx, ccy).

In some implementations, four LED strings (101A/101B/101C/101D) are present in a device 100. One or more of the LED strings can have recipient luminophoric mediums (102A/102B/102C/102D). A first LED string 101A and a first luminophoric medium 102A together can emit a first light having a first color point within a blue color range. The combination of the first LED string 101A and the first luminophoric medium 102A are also referred to herein as a "blue channel." A second LED string 101B and a second luminophoric medium 102B together can emit a second light having a second color point within a red color range. The combination of the second LED string 101A and the second luminophoric medium 102A are also referred to herein as a "red channel." A third LED string 101C and a third luminophoric medium 102C together can emit a third light having a third color point within a green color range. The combination of the third LED string 101C and the third luminophoric medium 102C are also referred to herein as a "green channel." A fourth LED string 101D and a fourth luminophoric medium 102D together can emit a fourth light having a fourth color point within a cyan color range. The combination of the fourth LED string 101D and the fourth luminophoric medium 102D are also referred to herein as a "cyan channel."

The first, second, third, and fourth LED strings 101A/ 101B/101C/101D can be provided with independently applied on-state drive currents in order to tune the intensity of the first, second, third and fourth unsaturated light produced by each string and luminophoric medium together. By varying the drive currents in a controlled manner, the color coordinate (ccx, ccy) of the total light that is emitted from the device 100 can be tuned. In some implementations, the device 100 can provide light at substantially the same color coordinate with different spectral power distribution profiles, which can result in different light characteristics at the same CCT. In some implementations, white light can be generated in modes that produce light from two or three of the LED strings. In some implementations, white light is generated using only the first, second, and third LED strings, i.e. the blue, red, and green channels. In other implementations, white light is generated using the first, second, third, and fourth LED strings, i.e., the blue, red, green, and cyan channels. In further implementations, white light can be generated using the first, second, and fourth LED strings, i.e. the blue, red, and cyan channels. In some implementations, only two of the LED strings are producing light during the generation of white light, as the other two LED strings are not necessary to generate white light at the desired color point with the desired color rendering performance. In certain implementations, substantially the same color coordinate (ccx, ccy) of total light emitted from the device can be provided in two different operational modes (different combinations of two or more of the channels), but with different color-rendering, circadian, or other performance metrics, such that the functional characteristics of the generated light can be selected as desired by users.

Figure 5:
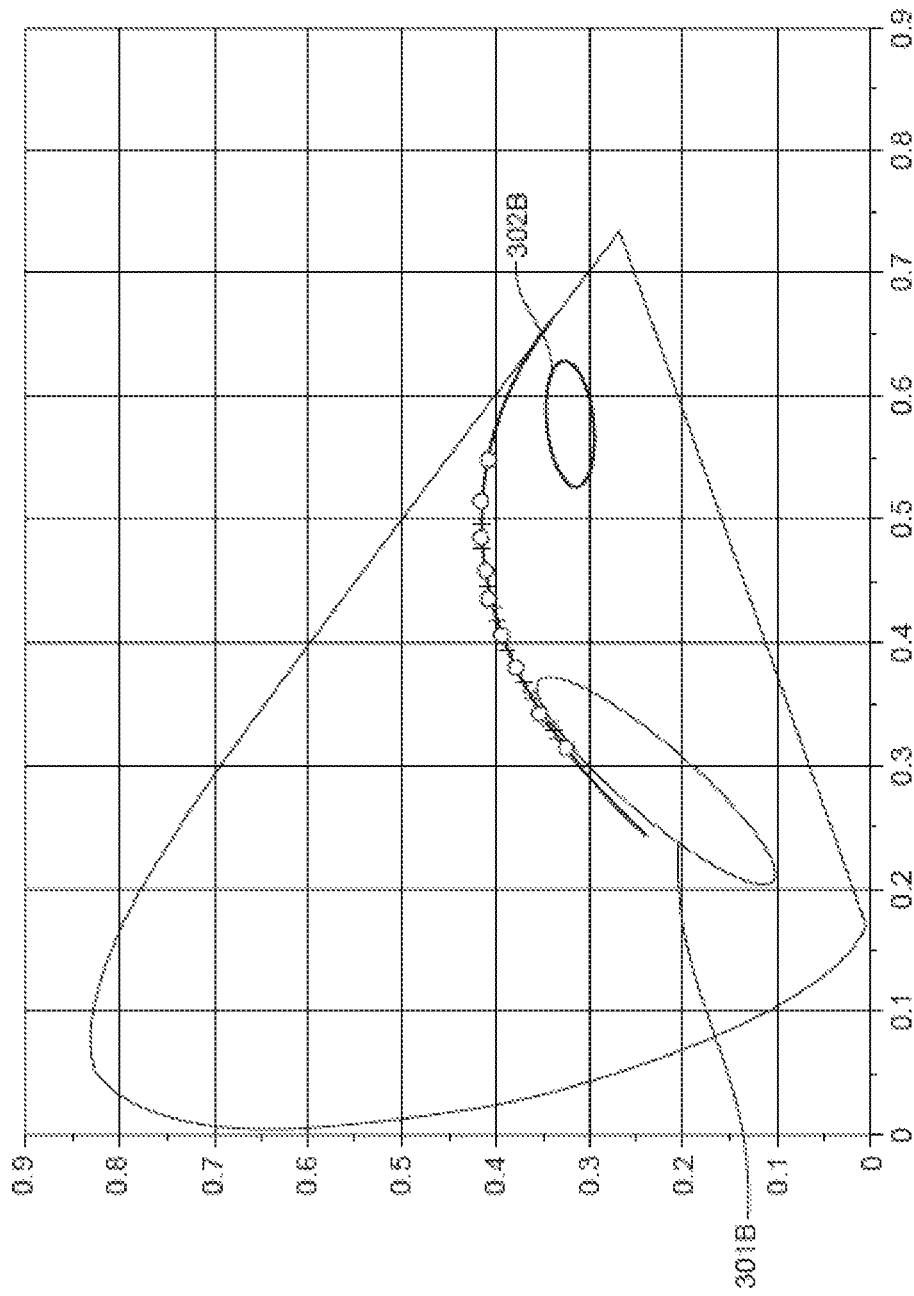
FIG. 5 illustrates some aspects of light emitting devices according to the present disclosure, including some suitable color ranges for light generated by components of the devices.
Figure 6:
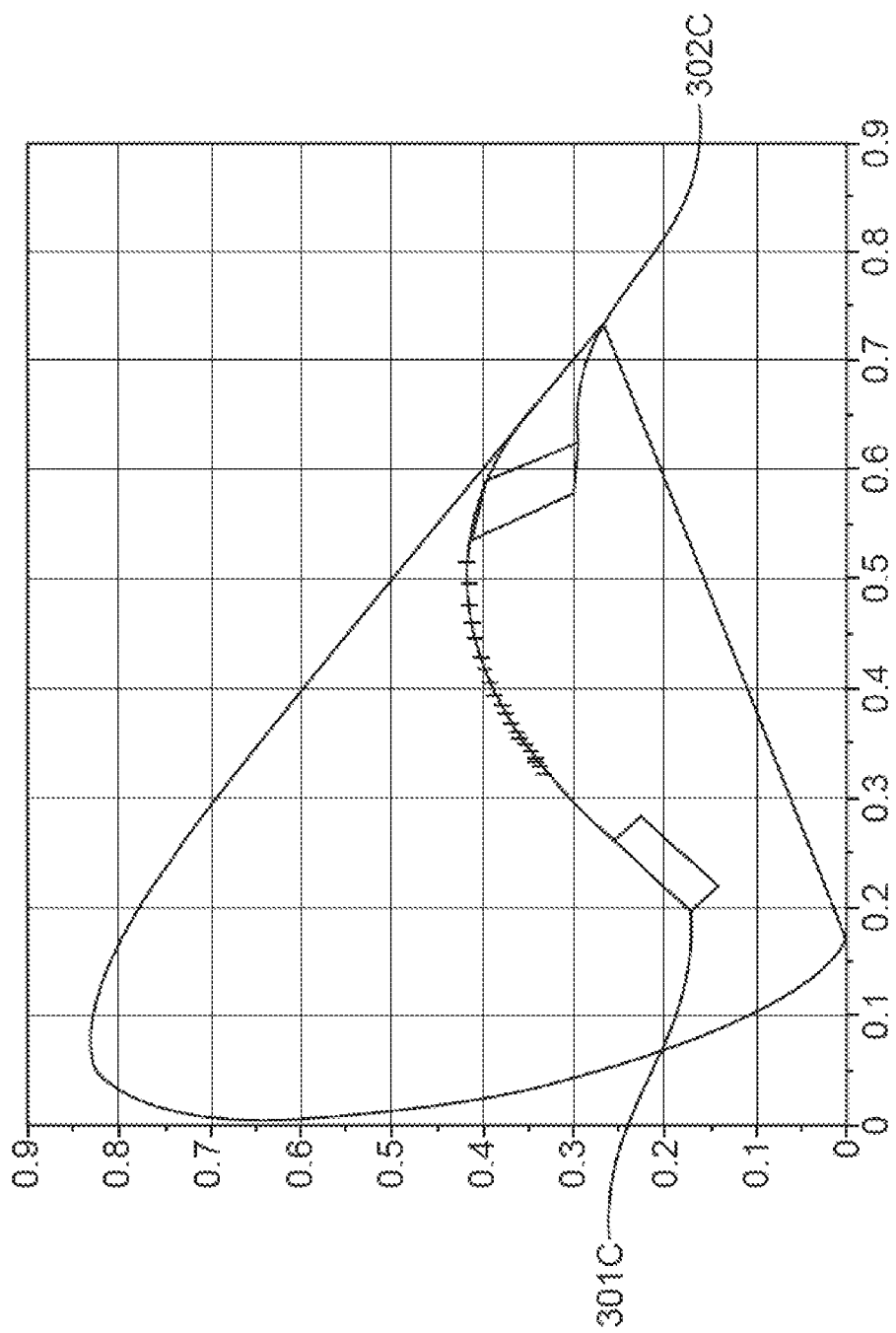
FIG. 6 illustrates some aspects of light emitting devices according to the present disclosure, including some suitable color ranges for light generated by components of the devices.

FIGS. 4-6 depict suitable color ranges for some implementations of the disclosure. FIG. 4A depicts a blue color range 301A defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus. FIG. 4B depicts a red color range 302A defined by the spectral locus between the constant CCT line of 1600K and the line of purples, the line of purples, a line connecting the ccx, ccy color coordinates (0.61, 0.21) and (0.47, 0.28), and the constant CCT line of 1600K. FIG. 4C depicts a cyan color range 304A defined by a line connecting the Planckian locus, the constant CCT line of 3200K, the spectral locus, and the constant CCT line of 20000K. FIG. 4E depicts a green color range 303A defined by the constant CCT line of 6700K, the Planckian locus, and the spectral locus. It should be understood that any gaps or openings in the described boundaries for the color ranges 301A, 302A, 303A, 304A should be closed with straight lines to connect adjacent endpoints in order to define a closed boundary for each color range.

In some implementations, suitable color ranges can be narrower than those described above. FIG. 5 depicts some suitable color ranges for some implementations of the disclosure. A blue color range 301B can be defined by a 60-step MacAdam ellipse at a CCT of 20000K, 40 points below the Planckian locus. A red color range 302B can be defined by a 20-step MacAdam ellipse at a CCT of 1200K, 20 points below the Planckian locus. A green color range 303B shown in FIG. 4F can be defined by a 60-step MacAdam ellipse centered approximately 65 points above the Planckian locus at 4500K, the Planckian locus, and the constant CCT line of 6700K. A cyan color range 304B shown in FIG. 4D can be defined by 41-step MacAdam ellipse centered approximately 46 points above the Planckian locus at a CCT of 5600K, and the Planckian locus. FIG. 6 depicts some further color ranges suitable for some implementations of the disclosure. A blue color range 301C is defined by a polygonal region on the 1931 CIE Chromaticity Diagram defined by the following ccx, ccy color coordinates: (0.22, 0.14), (0.19, 0.17), (0.26, 0.26), (0.28, 0.23). A red color range 302C is defined by a polygonal region on the 1931 CIE Chromaticity Diagram defined by the following ccx, ccy color coordinates: (0.53, 0.41), (0.59, 0.39), (0.63, 0.29), (0.58, 0.30).

In some implementations, the LEDs in the first, second, third and fourth LED strings can be LEDs with peak emission wavelengths at or below about 535 nm. In some implementations, the LEDs emit light with peak emission wavelengths between about 360 nm and about 535 nm. In some implementations, the LEDs in the first, second, third and fourth LED strings can be formed from InGaN semiconductor materials. In some preferred implementations, the first, second, and third LED strings can have LEDs having a peak wavelength between about 405 nm and about 485 nm, between about 430 nm and about 460 nm, between about 430 nm and about 455 nm, between about 430 nm and about 440 nm, between about 440 nm and about 450 nm, between about 440 nm and about 445 nm, or between about 445 nm and about 450 nm. The LEDs used in the first, second, third, and fourth LED strings may have full-width half-maximum wavelength ranges of between about 10 nm and about 30 nm. In some preferred implementations, the first, second, and third LED strings can include one or more LUXEON Z Color Line royal blue LEDs (product code LXZ1-PR01) of color bin codes 1, 2, 3, 4, 5, or 6 or one or more LUXEON Z Color Line blue LEDs (LXZ1-PB01) of color bin code 1 or 2 (Lumileds Holding B.V., Amsterdam, Netherlands). In some implementations, the LEDs used in the fourth LED string can be LEDs having peak emission wavelengths between about 360 nm and about 535 nm, between about 380 nm and about 520 nm, between about 470 nm and about 505 nm, about 480 nm, about 470 nm, about 460 nm, about 455 nm, about 450 nm, or about 445 nm. Similar LEDs from other manufacturers such as OSRAM GmbH and Cree, Inc. could also be used, provided they have peak emission and full-width half-maximum wavelengths of the appropriate values.

In implementations utilizing LEDs that emit substantially saturated light at wavelengths between about 360 nm and about 535 nm, the device 100 can include suitable recipient luminophoric mediums for each LED in order to produce light having color points within the suitable blue color ranges 301A-C, red color ranges 302A-C, green color ranges 303A-C, and cyan color ranges 304A-C described herein. The light emitted by each LED string, i.e., the light emitted from the LED(s) and associated recipient luminophoric medium together, can have a spectral power distribution ("SPD") having spectral power with ratios of power across the visible wavelength spectrum from about 380 nm to about 780 nm. While not wishing to be bound by any particular theory, it is speculated that the use of such LEDs in combination with recipient luminophoric mediums to create unsaturated light within the suitable color ranges 301A-C. 302A-C, 303A-B, and 304A-B provides for improved color rendering performance for white light across a predetermined range of CCTs from a single device 100. Further, while not wishing to be bound by any particular theory, it is speculated that the use of such LEDs in combination with recipient luminophoric mediums to create unsaturated light within the suitable color ranges 301A-C, 302A-C, 303A-B, and 304A-B provides for improved light rendering performance, providing higher EML performance along with color-rendering performance, for white light across a predetermined range of CCTs from a single device 100. Some suitable ranges for spectral power distribution ratios of the light emitted by the four LED strings (101A/101B/101C/101D) and recipient luminophoric mediums (102A/102B/102C/102D), if provided, together are shown in Tables 1 and 2. The Tables show the ratios of spectral power within wavelength ranges, with an arbitrary reference wavelength range selected for each color range and normalized to a value of 100.0. Tables 1 and 2 show suitable minimum and maximum values for the spectral intensities within various ranges relative to the normalized range with a value of 100.0, for the color points within the blue, green, red, and cyan color ranges. While not Wishing to be bound by any particular theory, it is speculated that because the spectral power distributions for generated light with color points within the blue, cyan, and yellow/green color ranges contains higher spectral intensity across visible wavelengths as compared to lighting apparatuses and methods that utilize more saturated colors, this allows for improved color rendering for test colors other than R1-R8.

spectral power in one or more of the wavelength ranges other than the reference wavelength range increased or decreased within 30% greater or less, within 20% greater or less, within 10% greater or less, or within 5% greater or less than the values shown in Table 3.

In some implementations, the cyan channel can have certain spectral power distributions. Table 3 shows ratios of spectral power within wavelength ranges, with an arbitrary reference wavelength range selected for the cyan color range and normalized to a value of 100.0, for several non-limiting embodiments of the cyan channel. The ccx, ccy color coordinates and dominant wavelengths of the exemplary cyan channels of Table 3 are provided in Table 5. In certain implementations, the cyan channel can have a spectral power distribution with spectral power in one or more of the wavelength ranges other than the reference wavelength range increased or decreased within 30% greater or less, within 20% greater or less, within 10% greater or less, or within 5% greater or less than the values shown in Table 3.

In some implementations, the red channel can have certain spectral power distributions. Tables 3 and 4 show the

TABLE 1

| | Spectral Power Distribution for Wavelength Ranges (nm) | | | | | | | | | |
|---|---|---|---|---|---|---|---|---|---|---|
| | $380 < \lambda \leq 420$ | $420 < \lambda \leq 460$ | $460 < \lambda \leq 500$ | $500 < \lambda \leq 540$ | $540 < \lambda \leq 580$ | $580 < \lambda \leq 620$ | $620 < \lambda \leq 660$ | $660 < \lambda \leq 700$ | $700 < \lambda \leq 740$ | $740 < \lambda \leq 780$ |
| Blue minimum | 0.3 | 100.0 | 20.9 | 15.2 | 25.3 | 26.3 | 15.4 | 5.9 | 2.3 | 1.0 |
| Blue maximum | 8.1 | 100.0 | 196.1 | 35.6 | 40.5 | 70.0 | 80.2 | 20.4 | 7.8 | 2.3 |
| Red minimum | 0.0 | 2.1 | 2.0 | 1.4 | 8.7 | 48.5 | 100.0 | 1.8 | 0.5 | 0.3 |
| Red maximum | 14.8 | 15. | 6.7 | 12.2 | 20.5 | 102.8 | 100.0 | 74.3 | 29.5 | 9.0 |
| Green minimum | 0.2 | 100.0 | 112.7 | 306.2 | 395.1 | 318.2 | 245.0 | 138.8 | 52.6 | 15.9 |
| Green maximum | 130.6 | 100.0 | 534.7 | 6748.6 | 10704.1 | 13855.8 | 15041.2 | 9802.9 | 3778.6 | 1127.3 |
| Cyan minimum | 0.0 | 0.0 | 100.0 | 80.5 | 47.2 | 37.2 | 20.8 | 7.9 | 2.6 | 1.1 |
| Cyan maximum | 0.7 | 5.9 | 100.0 | 180.1 | 124.7 | 107.9 | 102.9 | 63.1 | 24.4 | 7.3 |

TABLE 2

| | Spectral Power Distribution for Wavelength Ranges (nm) | | | |
|---|---|---|---|---|
| | $380 < \lambda \leq 500$ | $500 < \lambda \leq 600$ | $600 < \lambda \leq 700$ | $700 < \lambda \leq 780$ |
| Blue minimum | 100.0 | 27.0 | 24.8 | 1.1 |
| Blue maximum | 100.0 | 65.1 | 46.4 | 6.8 |
| Red minimum | 17.4 | 8.9 | 100.0 | 1.1 |
| Red maximum | 3.3 | 24.8 | 100.0 | 18.1 |
| Green minimum | 100.0 | 279.0 | 170.8 | 14.6 |
| Green maximum | 100.0 | 2313.6 | 2211.6 | 270.7 |
| Cyan minimum | 100.0 | 161.0 | 43.7 | 3.5 |
| Cyan maximum | 100.0 | 340.0 | 213.2 | 30.7 |

In some implementations, the green channel can have certain spectral power distributions. Table 3 shows the ratios of spectral power within wavelength ranges, with an arbitrary reference wavelength range selected for the green color range and normalized to a value of 100.0, for a green channel that may be used in some implementations of the disclosure. The exemplary Green Channel 1 has a ccx, ccy color coordinate of (0.3263, 0.5403) and a dominant wavelength of approximately 554 nm. The exemplary Green Channel 2 has a ccx, ccy color coordinate of (0.4482, 0.5258) and a dominant wavelength of approximately 573 nm. The exemplary Green Channel 3 has a ccx, ccy color coordinate of (0.5108, 0.4708) and a dominant wavelength of approximately 582 nm. In certain implementations, the green channel can have a spectral power distribution with ratios of spectral power within wavelength ranges, with an arbitrary reference wavelength range selected for the red color range and normalized to a value of 100.0, for a red channel that may be used in some implementations of the disclosure. The exemplary Red Channel 1 has a ccx, ccy color coordinate of (0.5735, 0.3007) and a dominant wavelength of approximately 641 nm. The exemplary Red Channel 2 has a ccx, ccy color coordinate of (0.5842, 0.3112) and a dominant wavelength of approximately 625 nm. In certain implementations, the red channel can have a spectral power distribution with spectral power in one or more of the wavelength ranges other than the reference wavelength range increased or decreased within 30% greater or less, within 20% greater or less, within 10% greater or less, or within 5% greater or less than the values shown in Tables 3 and 4.

In some implementations, the blue channel can have certain spectral power distributions. Tables 3 and 4 show the ratios of spectral power within wavelength ranges, with an arbitrary reference wavelength range selected for the blue color range and normalized to a value of 100.0, for a blue channel that may be used in some implementations of the disclosure. The exemplary Blue Channel 1 has a ccx, ccy color coordinate of (0.252, 0.223) and a dominant wavelength of approximately 470 nm. Exemplary Blue Channel 2 has a ccx, ccy color coordinate of (0.2625, 0.1763) and a dominant wavelength of approximately 381 nm. In certain implementations, the blue channel can have a spectral power distribution with spectral power in one or more of the wavelength ranges other than the reference wavelength range increased or decreased within 30% greater or less, within 20% greater or less, within 10% greater or less, or within 5% greater or less than the values shown in Tables 3 and 4.

phoric mediums having the desired saturated color points when excited by their respective LED strings (101A/101B/101C/101D) including luminescent materials such as those disclosed in co-pending application PCT/US2016/015318

TABLE 3

Spectral Power Distribution for Wavelength Ranges (nm)

| Exemplary Color Channels | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 | 560 < λ ≤ 580 | 580 < λ ≤ 600 | 600 < λ ≤ 620 |
|---|---|---|---|---|---|---|---|---|---|---|---|---|
| Blue Channel 1 | 0.3 | 0.7 | 11.4 | 100 | 70.7 | 27.9 | 23.5 | 25.1 | 24.6 | 22.3 | 21.0 | 21.2 |
| Red Channel 1 | 0.1 | 0.1 | 0.7 | 4.5 | 4.9 | 3.5 | 6.7 | 11.6 | 17.6 | 30.0 | 48.9 | 67.9 |
| Green Channel 1 | 0.6 | 0.5 | 2.4 | 14.0 | 21.6 | 63.4 | 97.1 | 99.5 | 100.0 | 89.1 | 71.9 | 57.8 |
| Green Channel 2 | 0.4 | 1.5 | 1.6 | 0.5 | 1.0 | 10.0 | 81.3 | 93.5 | 100.0 | 93.5 | 84.5 | 77.3 |
| Green Channel 3 | 0.0 | 0.0 | 0.1 | 1.2 | 2.3 | 3.3 | 23.1 | 51.6 | 64.5 | 67.5 | 73.5 | 89.3 |
| Cyan Channel 1 | 0.1 | 0.2 | 0.6 | 4.7 | 43.9 | 100.0 | 99.0 | 70.8 | 59.6 | 51.9 | 44.7 | 37.7 |
| Cyan Channel 2 | 0.2 | 0.3 | 0.7 | 2.1 | 17.1 | 92.3 | 100.0 | 48.7 | 28.9 | 22.7 | 20.4 | 20.3 |
| Cyan Channel 3 | 0.0 | 0.0 | 0.0 | 0.0 | 14.1 | 97.3 | 100.0 | 77.6 | 71.9 | 67.0 | 57.9 | 45.0 |
| Cyan Channel 4 | 0.2 | 0.3 | 0.8 | 11.0 | 100.0 | 99.4 | 83.2 | 77.5 | 75.3 | 71.7 | 69.9 | 64.6 |
| Cyan Channel 5 | 0.1 | 0.2 | 0.8 | 11.0 | 100.0 | 99.5 | 83.4 | 77.2 | 72.1 | 60.6 | 47.5 | 35.2 |
| Cyan Channel 6 | 0.1 | 0.2 | 0.6 | 3.4 | 32.6 | 100.0 | 90.2 | 67.6 | 57.4 | 47.1 | 36.9 | 27.5 |
| Cyan Channel 7 | 0.3 | 0.4 | 0.7 | 1.9 | 14.2 | 80.4 | 100.0 | 70.4 | 58.3 | 53.0 | 50.7 | 51.4 |
| Cyan Channel 8 | 0.1 | 0.2 | 0.5 | 1.8 | 15.2 | 83.3 | 100.0 | 68.2 | 55.5 | 48.8 | 42.1 | 37.9 |
| Cyan Channel 9 | 0.3 | 0.4 | 0.7 | 1.9 | 14.2 | 80.4 | 100.0 | 70.4 | 58.3 | 53.0 | 50.7 | 51.4 |

| Exemplary Color Channels | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|
| Blue Channel 1 | 20.9 | 18.1 | 13.4 | 8.7 | 5.2 | 3.1 | 1.9 | 1.3 | 0.0 |
| Red Channel 1 | 93.5 | 100.0 | 66.0 | 33.7 | 16.5 | 7.6 | 3.2 | 1.5 | 0.0 |
| Green Channel 1 | 54.1 | 48.6 | 31.0 | 16.1 | 8.1 | 3.9 | 1.8 | 1.1 | 0.0 |
| Green Channel 2 | 72.0 | 62.7 | 47.5 | 31.7 | 19.2 | 11.0 | 6.0 | 3.1 | 0.0 |
| Green Channel 3 | 100.0 | 91.3 | 70.0 | 47.1 | 28.8 | 16.6 | 9.1 | 4.8 | 0.0 |
| Cyan Channel 1 | 30.0 | 19.9 | 12.4 | 7.3 | 4.2 | 2.4 | 1.4 | 0.9 | 0.0 |
| Cyan Channel 2 | 19.6 | 16.5 | 11.8 | 7.6 | 4.5 | 2.6 | 1.4 | 0.7 | 0.0 |
| Cyan Channel 3 | 31.3 | 19.7 | 12.0 | 7.0 | 4.1 | 2.3 | 1.3 | 0.7 | 0.0 |
| Cyan Channel 4 | 53.1 | 37.5 | 23.8 | 13.8 | 7.7 | 4.2 | 2.4 | 1.6 | 0.0 |
| Cyan Channel 5 | 25.1 | 16.3 | 10.0 | 5.8 | 3.3 | 1.8 | 1.2 | 1.0 | 0.0 |
| Cyan Channel 6 | 19.7 | 12.9 | 7.9 | 4.6 | 2.6 | 1.5 | 1.0 | 0.8 | 0.0 |
| Cyan Channel 7 | 51.2 | 46.1 | 35.8 | 23.9 | 14.7 | 8.4 | 4.6 | 2.4 | 0.0 |
| Cyan Channel 8 | 31.9 | 15.6 | 7.5 | 3.6 | 1.9 | 1.1 | 0.7 | 0.4 | 0.0 |
| Cyan Channel 9 | 51.2 | 46.1 | 35.8 | 23.9 | 14.7 | 8.4 | 4.6 | 2.4 | 0.0 |

TABLE 4

Spectral Power Distribution for Wavelength Ranges (nm)

| Exemplary Color Channels | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|
| Blue Channel 2 | 0.4 | 100.0 | 20.9 | 15.2 | 25.3 | 26.3 | 25.1 | 13.9 | 5.2 | 1.6 |
| Red Channel 2 | 9.2 | 8.6 | 1.0 | 4.6 | 11.0 | 46.5 | 100.0 | 75.5 | 29.8 | 8.5 |

TABLE 5

| Exemplary Color Channels | ccx | ccy | Dominant wavelength (nm) |
|---|---|---|---|
| Cyan Channel 1 | 0.3248 | 0.5036 | 551 |
| Cyan Channel 2 | 0.2723 | 0.5127 | 534 |
| Cyan Channel 3 | 0.3515 | 0.5306 | 559 |
| Cyan Channel 4 | 0.3444 | 0.4297 | 560 |
| Cyan Channel 5 | 0.2935 | 0.4381 | 531 |
| Cyan Channel 6 | 0.3001 | 0.5055 | 545 |
| Cyan Channel 7 | 0.3740 | 0.5083 | 564 |
| Cyan Channel 8 | 0.3361 | 0.5257 | 556 |
| Cyan Channel 9 | 0.3258 | 0.5407 | 554 |

Blends of luminescent materials can be used in luminophoric mediums (102A/102B/102C/102D) to create lumino- phoric mediums having the desired saturated color points when excited by their respective LED strings (101A/101B/101C/101D) including luminescent materials such as those disclosed in co-pending application PCT/US2016/015318 filed Jan. 28, 2016, entitled "Compositions for LED Light Conversions", the entirety of which is hereby incorporated by this reference as if fully set forth herein. Traditionally, a desired combined output light can be generated along a tie line between the LED string output light color point and the saturated color point of the associated recipient luminophoric medium by utilizing different ratios of total luminescent material to the encapsulant material in which it is incorporated. Increasing the amount of luminescent material in the optical path will shift the output light color point towards the saturated color point of the luminophoric medium. In some instances, the desired saturated color point of a recipient luminophoric medium can be achieved by blending two or more luminescent materials in a ratio. The appropriate ratio to achieve the desired saturated color point can be determined via methods known in the art. Generally speaking, any blend of luminescent materials can be treated as if it were a single luminescent material, thus the ratio of luminescent materials in the blend can be adjusted to continue to meet a target CIE value for LED strings having different peak emission wavelengths. Luminescent materials can be tuned for the desired excitation in response to the selected LEDs used in the LED strings (101A/101B/101C/101D), which may have different peak emission wavelengths within the range of from about 360 nm to about 535 nm. Suitable methods for tuning the response of luminescent materials are known in the art and may include altering the concentrations of dopants within a phosphor, for example. In some implementations of the present disclosure, luminophoric mediums can be provided with combinations of two types of luminescent materials. The first type of luminescent material emits light at a peak emission between about 515 nm and about 590 nm in response to the associated LED string emission. The second type of luminescent material emits at a peak emission between about 590 nm and about 700 nm in response to the associated LED string emission. In some instances, the luminophoric mediums disclosed herein can be formed from a combination of at least one luminescent material of the first and second types described in this paragraph. In implementations, the luminescent materials of the first type can emit light at a peak emission at about 515 nm, 525 nm, 530 nm, 535 nm, 540 nm, 545 nm, 550 nm, 555 nm, 560 nm, 565 nm, 570 nm, 575 nm, 580 nm, 585 nm, or 590 nm in response to the associated LED string emission. In preferred implementations, the luminescent materials of the first type can emit light at a peak emission between about 520 nm to about 555 nm. In implementations, the luminescent materials of the second type can emit light at a peak emission at about 590 nm, about 595 nm, 600 nm, 605 nm, 610 nm, 615 nm, 620 nm, 625 nm, 630 nm, 635 nm, 640 nm, 645 nm, 650 nm, 655 nm, 670 nm, 675 nm, 680 nm, 685 nm, 690 nm, 695 nm, or 700 nm in response to the associated LED string emission. In preferred implementations, the luminescent materials of the first type can emit light at a(peak emission between about 600 nm to about 670 nm. Some exemplary luminescent materials of the first and second type are disclosed elsewhere herein and referred to as Compositions A-F. Table 6 shows aspects of some exemplar luminescent materials and properties:

TABLE 6

| Designator | Exemplary Material(s) | Density (g/mL) | Emission Peak (nm) | FWHM (nm) | Emission Peak Range (nm) | FWHM Range (nm) |
|---|---|---|---|---|---|---|
| Composition "A" | Luag: Cerium doped lutetium aluminum garnet ($Lu_3Al_5O_{12}$) | 6.73 | 535 | 95 | 530-540 | 90-100 |
| Composition "B" | Yag: Cerium doped yttrium aluminum garnet ($Y_3Al_5O_{12}$) | 4.7 | 550 | 110 | 545-555 | 105-115 |
| Composition "C" | a 650 nm-peak wavelength emission phosphor: Europium doped calcium aluminum silica nitride ($CaAlSiN_3$) | 3.1 | 650 | 90 | 645-655 | 85-95 |
| Composition "D" | a 525 nm-peak wavelength emission phosphor: GBAM: $BaMgAl_{10}O_{17}$:Eu | 3.1 | 525 | 60 | 520-530 | 55-65 |
| Composition "E" | a 630 nm-peak wavelength emission quantum dot: any semiconductor quantum dot material of appropriate size for desired emission wavelengths | 5.1 | 630 | 40 | 625-635 | 35-45 |
| Composition "F" | a 610 nm-peak wavelength emission quantum dot: any semiconductor quantum dot material of appropriate size for desired emission wavelengths | 5.1 | 610 | 40 | 605-615 | 35-45 |

Blends of Compositions A-F can be used in luminophoric mediums (102A/102B/102C/102D) to create luminophoric mediums having the desired saturated color points when excited by their respective LED strings (101A/101B/101C/101D). In some implementations, one or more blends of one or more of Compositions A-F can be used to produce luminophoric mediums (102A/102B/102C/102D). In some preferred implementations, one or more of Compositions A, B, and D and one or more of Compositions C, E, and F can be combined to produce luminophoric mediums (102A/102B/102C/102D). In some preferred implementations, the encapsulant for luminophoric mediums (102A/102B/102C/102D) comprises a matrix material having density of about 1.1 mg/mm$^3$ and refractive index of about 1.545 or from about 1.4 to about 1.6. In some implementations, Composition A can have a refractive index of about 1.82 and a particle size from about 18 micrometers to about 40 micrometers. In some implementations, Composition B can have a refractive index of about 1.84 and a particle size from about 13 micrometers to about 30 micrometers. In some implementations, Composition C can have a refractive index of about 1.8 and a particle size from about 10 micrometers to about 15 micrometers. In some implementations, Composition D can have a refractive index of about 1.8 and a particle size from about 10 micrometers to about 15 micrometers. Suitable phosphor materials for Compositions A, B, C, and D are commercially available from phosphor manufacturers such as Mitsubishi Chemical Holdings Corporation (Tokyo, Japan), Intematix Corporation (Fremont, CA), EMD Performance Materials of Merck KGaA (Darmstadt, Germany), and PhosphorTech Corporation (Kennesaw, GA).

In some aspects, the present disclosure provides semiconductor light emitting devices capable to producing tunable white light through a range of CCT values. In some implementations, devices of the present disclosure can output white light at color points along a predetermined path within a 7-step MacAdam ellipse around any point on the black body locus having a correlated color temperature between 1800K and 10000K. In some implementations, the semiconductor light emitting devices can comprise first, second, third, and fourth LED strings, with each LED string comprising one or more LEDs having an associated luminophoric medium, wherein the first, second, third, and fourth LED strings together with their associated luminophoric mediums can comprise red, blue, green, and cy an channels respectively, producing first, second, third, and fourth unsaturated color points within red, blue, green, and cyan regions on the 1931 CIE Chromaticity diagram, respectively. In some implementations the devices can further include a control circuit can be configured to adjust a fifth color point of a fifth unsaturated light that results from a combination of the first, second, third, and fourth unsaturated light, with the fifth color point falls within a 7-step MacAdam ellipse around any point on the black body locus having a correlated color temperature between 1800K and 10000K. In some implementations the devices can be configured to generate the fifth unsaturated light corresponding to a plurality of points along a predefined path with the light generated at each point having light with Rf greater than or equal to about 85, Rg greater than or equal to about 90 and less than or equal to about 110, or both. In some implementations the devices can be configured to generate the fifth unsaturated light corresponding to a plurality of points along a predefined path with the light generated at each point having light with Ra greater than or equal to about 90 along points with correlated color temperature between about 1800K and 10000K. R9 greater than or equal to 70 along points with correlated color temperature between about 2000K and about 10000K, or both. In some implementations the devices can be configured to generate the fifth unsaturated light corresponding to a plurality of points along a predefined path with the light generated at each point having light with R9 greater than or equal to 80 along greater than or equal to 90% of the points with correlated color temperature between about 2000K and about 10000K. In some implementations the devices can be configured to generate the fifth unsaturated light corresponding to a plurality of points along a predefined path with the light generated at each point having one or more of EML greater than or equal to about 0.5 along points with correlated color temperature above about 2100K, EML greater than or equal to about 0.6 along points with correlated color temperature above about 2400K, EML greater than or equal to about 0.75 along points with correlated color temperature above about 3000K EML greater than or equal to about 1.0 along points with correlated color temperature above about 4000K, and EML greater than or equal to about 1.2 along points with correlated color temperature above about 6000K. In some implementations the devices can be configured to generate the fifth unsaturated light corresponding to a plurality of points along a predefined path with the light generated at each point having light with R13 greater than or equal to about 94, R15 greater than or equal to about 88, or both. The blue color region can comprise a region on the 1931 CIE Chromaticity Diagram defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus. In some implementations the red color region can comprise a region on the 1931 CIE Chromaticity Diagram defined by the spectral locus between the constant CCT line of 1600K and the line of purples, the line of purples, a line connecting the ccx, ccy color coordinates (0.61, 0.21) and (0.47, 0.28), and the constant CCT line of 1600K. The green color region can comprise a region on the 1931 CIE Chromaticity Diagram defined by the constant CCT line of 6700K, the Planckian locus, and the spectral locus. In some implementations the green color region can comprise a region on the 1931 CIE Chromaticity Diagram defined by a 60-step MacAdam ellipse centered approximately 65 points above the Planckian locus at 4500K, the Planckian locus, and the constant CCT line of 6700K. The cyan color region can comprise a region on the 1931 CIE Chromaticity Diagram defined by a line connecting the Planckian locus, the constant CCT line of 3200K, the spectral locus, and the constant CCT line of 20000K. The cyan color region can comprise a region on the 1931 CIE Chromaticity Diagram defined by a 41-step MacAdam ellipse centered approximately 46 points above the Planckian locus at a CCT of 5600K, and the Planckian locus. In some implementations the spectral power distributions for one or more of the red channel, blue channel, green channel, and cyan channel can fall within the minimum and maximum ranges shown in Tables 1 and 2. In some implementations the red channel can have a spectral power distribution with spectral power in one or more of the wavelength ranges other than the reference wavelength range increased or decreased within 30% greater or less, within 20% greater or less, within 10% greater or less, or within 5% greater or less than the values of a red channel shown in Tables 3 and 4. In some implementations the blue channel can have a spectral power distribution with spectral power in one or more of the wavelength ranges other than the reference wavelength range increased or decreased within 30% greater or less, within 20% greater or less, within 10% greater or less, or within 5% greater or less than the values of a blue channel shown in Tables 3 and 4. In some implementations the green channel can have a spectral power distribution with spectral power in one or more of the wavelength ranges other than the reference wavelength range increased or decreased within 30% greater or less, within 20% greater or less, within 10% greater or less, or within 5% greater or less than the values of a green channel shown in Table 3. In some implementations the cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a cyan channel shown in Table 3. In some implementations one or more of the LEDs in the fourth LED string can have a peak wavelength of between about 480 nm and about 505 nm. In some implementations one or more of the LEDs in the first, second, and third LED strings can have a peak wavelength of between about 430 nm and about 460 nm. In some implementations, the devices can be configured to generate the fifth unsaturated light corresponding to a plurality of points along a predefined path with the light generated at each point having light with BLH factor less than 0.05 $\mu W/cm^2$/lux. In some implementations, the devices can be configured to generate the fifth unsaturated light corresponding to a plurality of points along a predefined path with the light generated at each point having light with one or more of BLH factor less than or equal to about 0.01 along points with correlated color temperature below about 2100K, BLH factor less than or equal to about 0.015 along points with correlated color temperature below about 2400K, BLH factor less than or equal to about 0.025 along points with correlated color temperature below about 3000K, BLH factor less than or equal to about 0.05 along points with correlated color temperature below about 4000K. and BLH factor less than or equal to about 0.060 along points with correlated color temperature below about 6500K. In some implementations, the devices can be configured to generate the fifth unsaturated light corresponding to a plurality of points along a predefined path with the light generated at each point having light with the ratio of the EML to the BLH factor being greater than or equal to about 15, greater than or equal to about 20, greater than or equal to about 21, greater than or equal to about 22, greater than or equal to about 23, greater than or equal to about 24, greater than or equal to about 25, greater than or equal to about 26, greater than or equal to about 27, greater than or equal to about 28, greater than or equal to about 29, greater than or equal to about 30, greater than or equal to about 35, or greater than or equal to about 40. Providing a higher ratio of the EML to the BLH factor can be advantageous to provide light that provides desired biological impacts but does not have as much potential for photochemical induced injuries to the retina or skin.

In some aspects, the present disclosure provides methods of generating white light, the methods comprising providing first, second, third, and fourth LED strings, with each LED string comprising one or more LEDs having an associated luminophoric medium, wherein the first, second, third, and fourth LED strings together with their associated luminophoric mediums comprise red, blue, green, and cyan channels respectively, producing first, second, third, and fourth unsaturated light with color points within red, blue, green, and cyan regions on the 1931 CIE Chromaticity diagram, respectively, the methods further comprising providing a control circuit configured to adjust a fifth color point of a fifth unsaturated light that results from a combination of the first, second, third, and fourth unsaturated light, with the fifth color point falls within a 7-step MacAdam ellipse around any point on the black body locus having a correlated color temperature between 1800K and 10000K, generating two or more of the first, second, third, and fourth unsaturated light, and combining the two or more generated unsaturated lights to create the fifth unsaturated light. In some implementations the combining generates the fifth unsaturated light corresponding to a plurality of points along a predefined path with the light generated at each point having light with Rf greater than or equal to about 85, Rg greater than or equal to about 90 and less than or equal to about 110, or both. In some implementations the combining generates the fifth unsaturated light corresponding to a plurality of points along a predefined path with the light generated at each point having light with Ra greater than or equal to about 90 along points with correlated color temperature between about 1800K and 10000K, R9 greater than or equal to 70 along points with correlated color temperature between about 2000K and about 10000K. or both. In some implementations the combining generates the fifth unsaturated light corresponding to a plurality of points along a predefined path with the light generated at each point having light with R9 greater than or equal to 80 along greater than or equal to 90% of the points with correlated color temperature between about 2000K and about 10000K. In some implementations the combining generates the fifth unsaturated light corresponding to a plurality of points along a predefined path with the light generated at each point having one or more of EML greater than or equal to about 0.5 along points with correlated color temperature above about 2100K, EML greater than or equal to about 0.6 along points with correlated color temperature above about 2400K. EML greater than or equal to about 0.75 along points with correlated color temperature above about 3000K EML greater than or equal to about 1.0 along points with correlated color temperature above about 4000K, and EML greater than or equal to about 1.2 along points with correlated color temperature above about 6000K. In some implementations the combining generates the fifth unsaturated light corresponding to a plurality of points along a predefined path with the light generated at each point having light with R13 greater than or equal to about 94, R15 greater than or equal to about 88, or both. The blue color region can comprise a region on the 1931 CIE Chromaticity Diagram defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus. In some implementations the red color region can comprise a region on the 1931 CIE Chromaticity Diagram defined by the spectral locus between the constant CCT line of 1600K and the line of purples, the line of purples, a line connecting the ccx, ccy color coordinates (0.61, 0.21) and (0.47, 0.28), and the constant CCT line of 1600K. The green color region can comprise a region on the 1931 CIE Chromaticity Diagram defined by the constant CCT line of 6700K, the Planckian locus, and the spectral locus. In some implementations the green color region can comprise a region on the 1931 CIE Chromaticity Diagram defined by a 60-step MacAdam ellipse centered approximately 65 points above the Planckian locus at 4500K, the Planckian locus, and the constant CCT line of 6700K. In some implementations the cyan color region can comprise a region on the 1931 CIE Chromaticity Diagram defined by a line connecting the Planckian locus, the constant CCT line of 3200K, the spectral locus, and the constant CCT line of 20000K. The cyan color region can comprise a region on the 1931 CIE Chromaticity Diagram defined by a 41-step MacAdam ellipse centered approximately 46 points above the Planckian locus at a CCT of 5600K. and the Planckian locus. In some implementations the spectral power distributions for one or more of the red channel, blue channel, green channel, and cyan channel can fall within the minimum and maximum ranges shown in Tables 1 and 2. In some implementations the red channel can have a spectral power distribution with spectral power in one or more of the wavelength ranges other than the reference wavelength range increased or decreased within 30% greater or less, within 20% greater or less, within 10% greater or less, or within 5% greater or less than the values of a red channel shown in Tables 3 and 4. In some implementations the blue channel can have a spectral power distribution with spectral power in one or more of the wavelength ranges other than the reference wavelength range increased or decreased within 30% greater or less, within 20% greater or less, within 10% greater or less, or within 5% greater or less than the values of a blue channel shown in Tables 3 and 4. In some implementations the green channel can have a spectral power distribution with spectral power in one or more of the wavelength ranges other than the reference wavelength range increased or decreased within 30% greater or less, within 20% greater or less, within 10% greater or less, or within 5% greater or less than the values of a green channel shown in Table 3. In some implementations the cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a cyan channel shown in Table 3. In some implementations one or more of the LEDs in the fourth LED string can have a peak wavelength of between about 480 nm and about 505 nm. In some implementations one or more of the LEDs in the first, second, and third LED strings can have a peak wavelength of between about 430 nm and about 460 nm. In some implementations, the combining generates the fifth unsaturated light corresponding to a plurality of points along a predefined path with the light generated at each point having light with BLH factor less than 0.05 $\mu W/cm^2/lux$. In some implementations, the combining generates the fifth unsaturated light corresponding to a plurality of points along a predefined path with the light generated at each point having light with one or more of BLH factor less than or equal to about 0.01 along points with correlated color temperature below about 2100K, BLH factor less than or equal to about 0.015 along points with correlated color temperature below about 2400K, BLH factor less than or equal to about 0.025 along points with correlated color temperature below about 3000K, BLH factor less than or equal to about 0.05 along points with correlated color temperature below about 4000K, and BLH factor less than or equal to about 0.060 along points with correlated color temperature below about 6500K. In some implementations, the combining generates the fifth unsaturated light corresponding to a plurality of points along a predefined path with the light generated at each point having light with the ratio of the EML to the BLH factor being greater than or equal to about 15, greater than or equal to about 20, greater than or equal to about 21, greater than or equal to about 22, greater than or equal to about 23, greater than or equal to about 24, greater than or equal to about 25, greater than or equal to about 26, greater than or equal to about 27, greater than or equal to about 28, greater than or equal to about 29, greater than or equal to about 30, greater than or equal to about 35, or greater than or equal to about 40.

In some aspects, the present disclosure provides methods of generating white light with the semiconductor light emitting devices described herein. In some implementations, different operating modes can be used to generate the white light. In certain implementations, substantially the same white light points, with similar CCT values, can be generated in different operating modes that each utilize different combinations of the blue, red, green, and cyan channels of the disclosure. In some implementations, two operating modes can be used that comprise a first operating mode that uses the blue, red, and green channels and a second operating mode that uses the blue, red, and cyan channels of a device. In certain implementations, switching between the first operating mode and the second operating mode can increase the EML by about 5%, about 10%, about 15%, about 20%, about 25%, about 30%, about 35%, about 40%, about 45%, about 50%, about 55%, or about 60% while providing a Ra value within about 1, about 2, about 3, about 4, about 5, about 6, about 7, about 8, about 9, or about 10 at substantially the same CCT value. In some implementations, the light generated with the first operating mode and the light generated in the second operating mode can be within about 1.0 standard deviations of color matching (SDCM). In some implementations, the light generated with the first operating mode and the light generated in the second operating mode can be within about 0.5 standard deviations of color matching (SDCM). The methods of providing light under two or more operating modes can be used to provide white light that can be switched in order to provide desired biological effects to humans exposed to the light, such as by providing increased alertness and attention to workers by providing light with increased EML. Alternatively, light can be switched to a lower-EML light in order to avoid biological effects that could disrupt sleep cycles.

EXAMPLES

General Simulation Method.

Devices having four LED strings with particular color points were simulated. For each device, LED strings and recipient luminophoric mediums with particular emissions were selected, and then white light rendering capabilities were calculated for a select number of representative points on or near the Planckian locus between about 1800K and 10000K. Ra, R9, R13, R15, LER, Rf, Rg, CLA, CS, EML, BLH factor, CAF, CER, COI, and circadian performance values were calculated at each representative point.

The calculations were performed with Scilab (Scilab Enterprises, Versailles. France), LightTools (Synopsis. Inc., Mountain View, CA), and custom software created using Python (Python Software Foundation, Beaverton, OR). Each LED string was simulated with an LED emission spectrum and excitation and emission spectra of luminophoric medium(s). For luminophoric mediums comprising phosphors, the simulations also included the absorption spectrum and particle size of phosphor particles. The LED strings generating combined emissions within blue, green, and red color regions were prepared using spectra of a LUXEON Z Color Line royal blue LED (product code LXZ1-PR01) of color bin codes 3, 4, 5, or 6 or a LUXEON Z Color Line blue LED (LXZ1-PB01) of color bin code 1 or 2 (Lumileds Holding B.V., Amsterdam, Netherlands). The LED strings generating combined emissions with color points within the cyan regions were prepared using spectra of a LUXEON Z Color Line blue LED (LXZ1-PB01) of color bin code 5 or LUXEON Z Color Line cyan LED (LXZ1-PE01) color bin code 1, 8, or 9 (Lumileds Holding B.V., Amsterdam, Netherlands). Similar LEDs from other manufacturers such as OSRAM GmbH and Cree, Inc. could also be used.

The emission, excitation and absorption curves are available from commercially available phosphor manufacturers such as Mitsubishi Chemical Holdings Corporation (Tokyo, Japan), Intematix Corporation (Fremont, CA), EMD Performance Materials of Merck KGaA (Darmstadt. Germany), and PhosphorTech Corporation (Kennesaw, GA). The luminophoric mediums used in the LED strings were combinations of one or more of Compositions A, B, and D and one or more of Compositions C, E, and F as described more fully elsewhere herein. Those of skill in the art appreciate that various combinations of LEDs and luminescent blends can be combined to generate combined emissions with desired color points on the 1931 CIE chromaticity diagram and the desired spectral power distributions.

Example 1

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 1 as described above and shown in Table 3. A second LED string is driven by a blue LED having peak emission wavelength of approximately 450 nm to approximately 455 nm, utilizes a recipient luminophoric medium, and generates a combined emission of a red channel having the characteristics of Red Channel 1 as described above and shown in Table 3. A third LED string is driven by a blue LED having peak emission wavelength of approximately 450 nm to approximately 455 nm, utilizes a recipient luminophoric medium, and generates a combined emission of a green color channel having the characteristics of Green Channel 1 as described above and shown in Table 3. A fourth LED string is driven by a cyan LED having peak emission wavelength of approximately 505 nm, utilizes a recipient luminophoric medium, and generates a combined emission of a cyan channel having the characteristics of Cyan Channel 2 as described above and shown in Table 3 and 5.

FIGS. 7A-7F shows light-rendering characteristics of the device for a representative selection of white light color points near the Planckian locus. FIG. 7B-7C shows data for white light color points generated using only the first, second, and third LED strings. FIG. 7A shows data for white light color points generated using all four LED strings. FIGS. 7D-7E shows data for white light color points generated using only the first, second, and fourth LED strings. FIG. 7F show performance comparison between white light color points generated at similar approximate CCT values under operating modes using three or four LED strings.

Example 2

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 1 as described above and shown in Table 3. A second LED string is driven by a blue LED having peak emission wavelength of approximately 450 nm to approximately 455 nm, utilizes a recipient luminophoric medium, and generates a combined emission of a red channel having the characteristics of Red Channel 1 as described above and shown in Table 3. A third LED string is driven by a blue LED having peak emission wavelength of approximately 450 nm to approximately 455 nm, utilizes a recipient luminophoric medium, and generates a combined emission of a green color channel having the characteristics of Green Channel 1 as described above and shown in Table 3. A fourth LED string is driven by a cyan LED having peak emission wavelength of approximately 505 nm, utilizes a recipient luminophoric medium, and generates a combined emission of a cyan channel having the characteristics of Cyan Channel 3 as described above and shown in Table 3 and 5.

FIGS. 8A-8E shows light-rendering characteristics of the device for a representative selection of white light color points near the Planckian locus. FIG. 8A-8B shows data for white light color points generated using only the first, second, and third LED strings. FIGS. 8C-8D shows data for white light color points generated using only the first, second, and fourth LED strings. FIG. 8E show performance comparison between white light color points generated at similar approximate CCT values under operating modes using different sets of three LED strings.

Example 3

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 1 as described above and shown in Table 3. A second LED string is driven by a blue LED having peak emission wavelength of approximately 450 nm to approximately 455 nm, utilizes a recipient luminophoric medium, and generates a combined emission of a red channel having the characteristics of Red Channel 1 as described above and shown in Table 3. A third LED string is driven by a blue LED having peak emission wavelength of approximately 450 nm to approximately 455 nm, utilizes a recipient luminophoric medium, and generates a combined emission of a green color channel having the characteristics of Green Channel 1 as described above and shown in Table 3. A fourth LED string is driven by a cyan LED having peak emission wavelength of approximately 480 nm, utilizes a recipient luminophoric medium, and generates a combined emission of a cyan channel having the characteristics of Cyan Channel 4 as described above and shown in Table 3 and 5.

FIGS. 9A-9E shows light-rendering characteristics of the device for a representative selection of white light color points near the Planckian locus. FIG. 9A-9B shows data for white light color points generated using only the first, second, and third LED strings. FIGS. 9C-9D shows data for white light color points generated using only the first, second, and fourth LED strings. FIG. 9E show performance comparison between white light color points generated at similar approximate CCT values under operating modes using different sets of three LED strings.

Example 4

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 1 as described above and shown in Table 3. A second LED string is driven by a blue LED having peak emission wavelength of approximately 450 nm to approximately 455 nm, utilizes a recipient luminophoric medium, and generates a combined emission of a red channel having the characteristics of Red Channel 1 as described above and shown in Table 3. A third LED string is driven by a blue LED having peak emission wavelength of approximately 450 nm to approximately 455 nm, utilizes a recipient luminophoric medium, and generates a combined emission of a green color channel having the characteristics of Green Channel 1 as described above and shown in Table 3. A fourth LED string is driven by a cyan LED having peak emission wavelength of approximately 485 nm, utilizes a recipient luminophoric medium, and generates a combined emission of a cyan channel having the characteristics of Cyan Channel 5 as described above and shown in Table 3 and 5.

FIGS. 10A-10E shows light-rendering characteristics of the device for a representative selection of white light color points near the Planckian locus. FIG. 10A-10B shows data for white light color points generated using only the first, second, and third LED strings. FIGS. 10C-10D shows data for white light color points generated using only the first, second, and fourth LED strings. FIG. 10E show performance comparison between white light color points generated at similar approximate CCT values under operating modes using different sets of three LED strings.

Example 5

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 1 as described above and shown in Table 3. A second LED string is driven by a blue LED having peak emission wavelength of approximately 450 nm to approximately 455 nm, utilizes a recipient luminophoric medium, and generates a combined emission of a red channel having the characteristics of Red Channel 1 as described above and shown in Table 3. A third LED string is driven by a blue LED having peak emission wavelength of approximately 450 nm to approximately 455 nm, utilizes a recipient luminophoric medium, and generates a combined emission of a green color channel having the characteristics of Green Channel 1 as described above and shown in Table 3. A fourth LED string is driven by a cyan LED having peak emission wavelength of approximately 495 nm, utilizes a recipient luminophoric medium, and generates a combined emission of a cyan channel having the characteristics of Cyan Channel 6 as described above and shown in Table 3 and 5.

FIGS. 11A-11E shows light-rendering characteristics of the device for a representative selection of white light color points near the Planckian locus. FIG. 11A-11B shows data for white light color points generated using only the first, second, and third LED strings. FIGS. 11C-11D shows data for white light color points generated using only the first, second, and fourth LED strings. FIG. 11E show performance comparison between white light color points generated at similar approximate CCT values under operating modes using different sets of three LED strings.

Example 6

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 1 as described above and shown in Table 3. A second LED string is driven by a blue LED having peak emission wavelength of approximately 450 nm to approximately 455 nm, utilizes a recipient luminophoric medium, and generates a combined emission of a red channel having the characteristics of Red Channel 1 as described above and shown in Table 3. A third LED string is driven by a blue LED having peak emission wavelength of approximately 450 nm to approximately 455 nm, utilizes a recipient luminophoric medium, and generates a combined emission of a green color channel having the characteristics of Green Channel 1 as described above and shown in Table 3. A fourth LED string is driven by a cyan LED having peak emission wavelength of approximately 505 nm, utilizes a recipient luminophoric medium, and generates a combined emission of a cyan channel having the characteristics of Cyan Channel 7 as described above and shown in Table 3 and 5.

FIGS. 12A-12E shows light-rendering characteristics of the device for a representative selection of white light color points near the Planckian locus. FIG. 12A-12B shows data for white light color points generated using only the first, second, and third LED strings. FIGS. 12C-12D shows data for white light color points generated using only the first, second, and fourth LED strings. FIG. 12E show performance comparison between white light color points generated at similar approximate CCT values under operating modes using different sets of three LED strings.

Example 7

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 1 as described above and shown in Table 3. A second LED string is driven by a blue LED having peak emission wavelength of approximately 450 nm to approximately 455 nm, utilizes a recipient luminophoric medium, and generates a combined emission of a red channel having the characteristics of Red Channel 1 as described above and shown in Table 3. A third LED string is driven by a blue LED having peak emission wavelength of approximately 450 nm to approximately 455 nm, utilizes a recipient luminophoric medium, and generates a combined emission of a green color channel having the characteristics of Green Channel 1 as described above and shown in Table 3. A fourth LED string is driven by a cyan LED having peak emission wavelength of approximately 505 nm, utilizes a recipient luminophoric medium, and generates a combined emission of a cyan channel having the characteristics of Cyan Channel 8 as described above and shown in Table 3 and 5.

FIGS. 13A-13E shows light-rendering characteristics of the device for a representative selection of white light color points near the Planckian locus. FIG. 13A-13B shows data for white light color points generated using only the first, second, and third LED strings. FIGS. 13C-13D shows data for white light color points generated using only the first, second, and fourth LED strings. FIG. 13E show performance comparison between white light color points generated at similar approximate CCT values under operating modes using different sets of three LED strings.

Example 8

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 2 as described above and shown in Table 4. A second LED string is driven by a blue LED having peak emission wavelength of approximately 450 nm to approximately 455 nm, utilizes a recipient luminophoric medium, and generates a combined emission of a red channel having the characteristics of Red Channel 2 as described above and shown in Table 4. A third LED string is driven by a blue LED having peak emission wavelength of approximately 450 nm to approximately 455 nm, utilizes a recipient luminophoric medium, and generates a combined emission of a green color channel having the characteristics of Green Channel 2 as described above and shown in Table 3. A fourth LED string is driven by a cyan LED having peak emission wavelength of approximately 505 nm, utilizes a recipient luminophoric medium, and generates a combined emission of a cyan channel having the characteristics of Cyan Channel 9 as described above and shown in Table 3 and 5.

FIGS. 14A-14F shows light-rendering characteristics of the device for a representative selection of white light color points near the Planckian locus. FIG. 14B-14C shows data for white light color points generated using only the first, second, and third LED strings. FIG. 14A shows data for white light color points generated using all four LED strings. FIGS. 14D-14E shows data for white light color points generated using only the first, second, and fourth LED strings. FIG. 14F show performance comparison between white light color points generated at similar approximate CCT values under operating modes using three or four LED strings.

Example 9

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue channel having the characteristics of Blue Channel 2 as described above and shown in Table 4. A second LED string is driven by a blue LED having peak emission wavelength of approximately 450 nm to approximately 455 nm, utilizes a recipient luminophoric medium, and generates a combined emission of a red channel having the characteristics of Red Channel 2 as described above and shown in Table 4. A third LED string is driven by a blue LED having peak emission wavelength of approximately 450 nm to approximately 455 nm, utilizes a recipient luminophoric medium, and generates a combined emission of a green color channel having the characteristics of Green Channel 3 as described above and shown in Table 3. A fourth LED string is driven by a cyan LED having peak emission wavelength of approximately 505 nm, utilizes a recipient luminophoric medium, and generates a combined emission of a cyan channel having the characteristics of Cyan Channel 9 as described above and shown in Table 3 and 5.

FIGS. 15A-15E shows light-rendering characteristics of the device for a representative selection of white light color points near the Planckian locus. FIG. 15B shows data for white light color points generated using only the first, second, and third LED strings. FIG. 15A shows data for white light color points generated using all four LED strings. FIGS. 15C-15D shows data for white light color points generated using only the first, second, and fourth LED strings. FIG. 15E show performance comparison between white light color points generated at similar approximate CCT values under operating modes using three or four LED strings.

Those of ordinary skill in the art will appreciate that a variety of materials can be used in the manufacturing of the components in the devices and systems disclosed herein. Any suitable structure and/or material can be used for the various features described herein, and a skilled artisan will be able to select an appropriate structures and materials based on various considerations, including the intended use of the systems disclosed herein, the intended arena within which they will be used, and the equipment and/or accessories with which they are intended to be used, among other considerations. Conventional polymeric, metal-polymer composites, ceramics, and metal materials are suitable for use in the various components. Materials hereinafter discovered and/or developed that are determined to be suitable for use in the features and elements described herein would also be considered acceptable.

When ranges are used herein for physical properties, such as molecular weight, or chemical properties, such as chemical formulae, all combinations, and subcombinations of ranges for specific exemplar therein are intended to be included.

The disclosures of each patent, patent application, and publication cited or described in this document are hereby incorporated herein by reference, in its entirety.

Those of ordinary skill in the art will appreciate that numerous changes and modifications can be made to the exemplars of the disclosure and that such changes and modifications can be made without departing from the spirit of the disclosure. It is, therefore, intended that the appended claims cover all such equivalent variations as fall within the true spirit and scope of the disclosure.

What is claimed is:

1. A semiconductor light emitting device comprising:
    first, second, third, and fourth LED strings, with each LED string comprising one or more LEDs having an associated luminophoric medium
    wherein the first, second, third, and fourth LED strings together with their associated luminophoric mediums comprise red, blue, green, and cyan channels respectively, producing first, second, third, and fourth unsaturated color points within red, blue, green, and cyan regions on the 1931 C IE Chromaticity diagram, respectively; and
    a control circuit is configured to control said first, second, third, and fourth LED strings in at least two modes, a first mode in which light from the first, second, and fourth LED strings are combined into first mode emitted light, and a second mode in which light from said first, second and fourth LED strings are combined into a second mode emitted light, wherein said second mode emitted light has a higher EML than said first mode emitted light;
    wherein each of said first and second mode emitted light falls within a 7-step MacAdam ellipse around any point on the black body locus having a correlated color temperature between 2500K and 6500K.

2. The semiconductor light emitting device of claim 1, wherein the second mode emitted light has an EML greater than or equal to about 0.5 along points with correlated color temperature above about 2100K.

3. The semiconductor light emitting device of claim 1, wherein the second mode emitted light has an EML greater than or equal to about 0.6 along points with correlated color temperature above about 2400K.

4. The semiconductor light emitting device of claim 1, wherein the second mode emitted light has an EML greater than or equal to about 0.75 along points with correlated color temperature above about 3000K.

5. The semiconductor light emitting device of claim 1, wherein the second mode emitted light has an EML greater than or equal to about 1.0 along points with correlated color temperature above about 4000K.

6. The semiconductor light emitting device of claim 1, wherein the second mode emitted light has an EML greater than or equal to about 1.2 along points with correlated color temperature above about 6000K.

7. The semiconductor light emitting device of claim 1, wherein the first mode emitted light has an R13 greater than or equal to about 94.

8. The semiconductor light emitting device of claim 1, wherein the first mode emitted light has an R15 greater than or equal to about 88.

9. The semiconductor light emitting device of claim 1, wherein the red region is defined by the spectral locus between the constant CCT line of 1600K and the line of purples, the line of purples, a line connecting the ccx, ccy color coordinates (0.61, 0.21) and (0.47, 0.28), and the constant CCT line of 1600K.

10. The semiconductor light emitting device of claim 1, wherein the blue region is defined by a line connecting the ccx, ccy color coordinates of the infinity point of the Planckian locus (0.242, 0.24) and (0.12, 0.068), the Planckian locus from 4000K and infinite CCT, the constant CCT line of 4000K the line of purples, and the spectral locus.

11. The semiconductor light emitting device of claim 1, wherein the green color region comprises a region on the 1931 CIE Chromaticity Diagram defined by the constant CCT line of 6700K, the Planckian locus, and the spectral locus.

12. The semiconductor light emitting device of claim 1, wherein the cyan region is defined by a line connecting the Planckian locus, the constant CCT line of 3200K, the spectral locus, and the constant CCT line of 20000K.

* * * * *